United States Patent
Panzica et al.

(10) Patent No.: US 11,419,931 B2
(45) Date of Patent: Aug. 23, 2022

(54) COMPOSITIONS COMPRISING BACTERIAL STRAINS

(71) Applicant: 4D Pharma Research Limited, Aberdeen (GB)

(72) Inventors: Domenico Panzica, Aberdeen (GB); Amy Beth Holt, Aberdeen (GB); Suaad Ahmed, Aberdeen (GB); Anna Ettorre, Aberdeen (GB); Imke Elisabeth Mulder, Aberdeen (GB); Philip Cowie, Aberdeen (GB); Emma Raftis, Aberdeen (GB); Emma Elizabeth Clare Hennessy, Aberdeen (GB); Delphine Louise Claudette Laute-Caly, Aberdeen (GB); Aurélie Pascale Patricia Couturier-Maillard, Aberdeen (GB); Margaret Inkster Delday, Kemnay (GB); Marsilio Adriani, Aberdeen (GB); Maria Christofi, Aberdeen (GB)

(73) Assignee: 4D Pharma Research Limited, Aberdeen (GB)

(*) Notice: Subject to any disclaimer, the term of this patent is extended or adjusted under 35 U.S.C. 154(b) by 0 days.

(21) Appl. No.: 17/024,628

(22) Filed: Sep. 17, 2020

(65) Prior Publication Data
US 2021/0169950 A1 Jun. 10, 2021

Related U.S. Application Data

(63) Continuation of application No. PCT/EP2019/056894, filed on Mar. 19, 2019.

(30) Foreign Application Priority Data

| Mar. 19, 2018 | (GB) | 1804384 |
| Jun. 18, 2018 | (EP) | 18178350 |
| Jun. 18, 2018 | (GB) | 1809953 |
| Jul. 20, 2018 | (GB) | 1811900 |
| Jul. 30, 2018 | (GB) | 1812378 |
| Aug. 17, 2018 | (GB) | 1813423 |
| Aug. 17, 2018 | (GB) | 1813444 |
| Oct. 16, 2018 | (GB) | 1816834 |
| Oct. 29, 2018 | (GB) | 1817641 |
| Jan. 29, 2019 | (GB) | 1901199 |
| Jan. 29, 2019 | (GB) | 1901218 |
| Feb. 13, 2019 | (GB) | 1901992 |
| Feb. 13, 2019 | (GB) | 1901993 |

(51) Int. Cl.
| A61K 39/02 | (2006.01) |
| A61K 39/09 | (2006.01) |
| A61K 35/744 | (2015.01) |
| A61K 39/00 | (2006.01) |
| A61P 37/04 | (2006.01) |

(52) U.S. Cl.
CPC ............ *A61K 39/09* (2013.01); *A61K 35/744* (2013.01); *A61K 2039/585* (2013.01); *A61P 37/04* (2018.01)

(58) Field of Classification Search
None
See application file for complete search history.

(56) References Cited

U.S. PATENT DOCUMENTS

| 9,839,655 | B2 * | 12/2017 | Mulder | C12N 1/20 |
| 10,610,550 | B2 * | 4/2020 | Mulder | A61K 9/19 |
| 10,987,387 | B2 * | 4/2021 | Mulder | C12N 1/205 |
| 11,058,732 | B2 * | 7/2021 | Mulder | C12N 1/205 |
| 2004/0009937 | A1 | 1/2004 | Chen et al. | |
| 2016/0067188 | A1 | 3/2016 | Cade et al. | |
| 2021/0138058 | A1 | 5/2021 | Mulder et al. | |

FOREIGN PATENT DOCUMENTS

| EP | 0904784 A1 | 3/1999 |
| EP | 1958647 A1 | 8/2008 |
| EP | 2133092 A1 | 12/2009 |
| JP | 2017506212 A | 3/2017 |
| WO | WO-03046580 A1 | 6/2003 |
| WO | WO-2006110603 A1 | 10/2006 |
| WO | WO-2008144889 A1 | 12/2008 |
| WO | WO-2009130618 A2 | 10/2009 |
| WO | WO-2012097012 A1 | 7/2012 |
| WO | WO-2013008038 A2 | 1/2013 |
| WO | WO-2013008039 A2 | 1/2013 |
| WO | WO-2013050792 A1 | 4/2013 |
| WO | WO-2014043593 A2 | 3/2014 |
| WO | WO-2014167338 A1 | 10/2014 |
| WO | WO-2015121863 A1 | 8/2015 |
| WO | WO2017/085520 * | 5/2017 |
| WO | WO-2017085520 A1 | 5/2017 |
| WO | WO-2019010255 A1 | 1/2019 |

(Continued)

OTHER PUBLICATIONS

Aiello, Anna et al., Immunosenescence and Its Hallmarks: How to Oppose Aging Strategically? A Review of Potential Options for Therapeutic Intervention, Frontiers in Immunology, Sep. 2019, vol. 10, Article 2247, pp. 1-19, doi:10.3389/fimmu.2019.02247.

"Disease or Condition" ("Immunosenescence") Search List retrieved from Home—Clinical Trials.gov (https://clinicaltrials.gov/) on May 7, 2021.

"Immunosenescence" Search List retrieved from PubMed (https://pubmed.ncbi.nlm.nih.gov/) on May 6, 2021.

(Continued)

*Primary Examiner* — Jennifer E Graser

(74) *Attorney, Agent, or Firm* — Wilson Sonsini Goodrich & Rosati

(57) ABSTRACT

The invention provides compositions comprising bacterial strains for stimulating the immune system and treating and preventing diseases.

20 Claims, 36 Drawing Sheets

Specification includes a Sequence Listing.

(56) References Cited

FOREIGN PATENT DOCUMENTS

| | | |
|---|---|---|
| WO | WO-2019180000 A1 | 9/2019 |
| WO | WO-2019180051 A1 | 9/2019 |

OTHER PUBLICATIONS

May 28, 2021 Restriction Requirement U.S. Appl. No. 17/025,706.
Oct. 1, 2021 Non-Final Office Action U.S. Appl. No. 17/025,706.
Arenberg, et al., Interferon-γ-inducible Protein10 (IP-10) Is an Angiostatic Factor That Inhibits Human Non-small Cell Lung Cancer (NSCLC) Tumorigenesis and Spontaneous Metastases. 1996. J. Exp.Med.184:981-92. Sep. 1, 1996.
Atarashi et al. Induction of colonic regulatory T cells by indigenous *Clostridium* species. Science 331 (6015):337-341 (2011).Epub Dec. 23, 2010.
Attmannspacher Ursula et al., FliL is essential for swarming: motor rotation in absence of FliL fractures theflagellar rod in swarmer cells of *Salmonella enterica* (2008), Mol Microbiol 68,328-341.
Aw, Danielle et al."Immunosenescence: emerging challenges for an ageing population." Immunology vol. 120,4 (2007): 435-46. doi:10.1111/j.1365-2567.2007.02555.x.
Beatson SA, et al., "Variation in bacterial flagellins: from sequence to structure" Trends in Microbiology. Apr. 2006;14(4):151-155. DOI: 10.1016/j.tim.2006.02.008.
Bohnhorst, J., Rasmussen, T., Moen, S. et al. Toll-like receptors mediate proliferation and survival of multiple myeloma cells. Leukemia 20, 1138-1144 (2006). https://doi.org/10.1038/sj.leu.2404225.
Bork, P., "Powers and Pitfalls in Sequence Analysis: The 70% Hurdle", Genome Res., 2000, vol. 10, pp. 398-400.
Bowie, J. et al., "Deciphering the Message in Protein Sequences: Tolerance to Amino Acid Substitutions", Science, Mar. 16, 1990, vol. 247, pp. 1306-1310.
Brackett et al., "Toll-like receptor-5 agonist, entolimod, suppresses metastasis and induces immunity by stimulating an NK-dendritic-CD8+T-cell axis", (2016) PNAS, E874—E883.
Cai, Zhenyu et al., Activation of Toll-like Receptor 5 on Breast Cancer Cells by Flagellin Suppresses Cell Proliferation and Tumor Growth (2011) Cancer Res. 71(7): 2466-2475, DOI:10.1158/0008-5472.CAN-10-1993 Published Apr. 2011.
Chung et al. 'Microbiota-stimulated immune mechanisms to maintain gut homeostasis.' Current Opinion in Immunology. 2010, vol. 22, No. 4, pp. 455-460. Epub Jul. 23, 2010.
Colman, P.M., "Effects of amino acid sequence changes on antibody-antigen interactions", Res. Immunology, Jan. 1994, vol. 145, pp. 33-36.
Daillere, Romain et al., *Enterococcus hirae* and *Barnesiella intestinihominis* Facilitate Cyclophosphamide-Induced Therapeutic Immunomodulatory Effects, Immunity, 2016, vol. 45, pp. 931-943.
Darnton, Nicholas C, and Howard C Berg. "Bacterial flagella are firmly anchored." Journal of bacteriology vol. 190,24 (2008): 8223-4. doi:10.1128/JB.00908-08.
Database UniProt [Online] Jan. 25, 2012(Jan. 25, 2012), "Rec Name:Full=Flagellin {ECO:0000256IRuleBase:RU362073};", XP002791697, retrieved from EBI accession No. UNIPROT:G5IWG8, Database accession No. G5IWG8.
Filipe M de Melo et al. "Anti-metastatic immunotherapy based on mucosal administration of flagellin and immunomodulatory P10", (2015)Immunology and Cell Biology 93, 86-98.
Gaboriau-Routhiau et al. 'The key role of segmented filamentous bacteria in the coordinated maturation of gut helper T cell responses.' Immunity. 2009, vol. 31, No. 4, pp. 677-689.
Geuking et al. 'Intestinal bacterial colonization induces mutualistic regulatory T cell responses.' Immunity. 2011, vol. 34, No. 5, pp. 794-806. Epub May 19, 2011.
Gewirtz et al. (2001) Cutting edge: bacterial flagellin activates basolaterally expressed TLR5 to induce epithelial proinflammatory gene expression. The Journal of Immunology. 167:(4)1882-1885.

Greenspan, N. et al., "Defining epitopes: It's not as easy as it seems", Nature Biotechnology, Oct. 1999, vol. 17, pp. 936-937.
Haabeth et al. A model for cancer-suppressive inflammation. (2012) Oncolmmunology 1(1):1146-1152.
Hajam,I., Dar, P., Shahnawaz, I. et al. Bacterial flagellin—a potent immunomodulatory agent. Exp Mol Med 49, e373(2017). https://doi.org/10.1038/emm.2017.172.
International Preliminary Report on Patentability dated Sep. 11, 2020 for International Application Serial No. PCT/EP2019/056809, (16 pages).
Ivanov et al. 'Induction of intestinal Th17cells by segmented filamentous bacteria.' Cell. 2009, vol. 139, No. 3, pp. 485-498, available in PMC Apr. 30, 2010.
Jacchieri, Saul G, Structural Study of Binding of Flagellin by Toll-Like Receptor 5, Aug. 2003, Journal of Bacteriology 185(14):4243-7, DOI: 10.1128/JB.185.14.4243-4247.2003.
Kang, S. et al. (2010) "Dysbiosis of fecal microbiota in Crohn's disease patients as revealed by a custom phylogenetic microarray", Inflammatory Bowel Diseases. Dec. 2010;16(12):2034-2042.doi: 10.1002/ibd.21319.
Kelley, L., Mezulis, S., Yates, C. et al. The Phyre2 web portal for protein modeling, prediction and analysis. NatProtoc 10, 845-858 (2015). https://doi.org/10.1038/nprot.2015.053.
Kinnebrew, Melissa A et al. "Bacterial flagellin stimulates Toll-like receptor 5-dependent defense against vancomycin-resistant Enterococcus infection." The Journal of infectious diseases vol. 201,4 (2010): 534-43. doi:10.1086/650203.
Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.
Leigh, Nicholas D et al. "A flagellin-derived toll-like receptor 5 agonist stimulates cytotoxic lymphocyte-mediated tumor immunity." PloS one vol. 9,1 e85587. Jan. 14, 2014, doi:10.1371/journal.pone.0085587.
Lejeune et al. Efficiency of Recombinant Human TNF in Human Cancer Therapy. Cancer Immun. 6:6 (2006).
Lu, Yuan, and James R Swartz. "Functional properties of flagellin as a stimulator of innate immunity." Scientific reports vol. 6 18379. Jan. 12, 2016, doi:10.1038/srep18379.
MacPherson, AJ., et al., The functions of mucosal T cells in containing the indigenous commensal flora of the intestine, Cell Mol Life Sci. Dec. 2002;59(12):2088-96.
MacPherson et al. 'IgA adaptation to the presence of commensal bacteria in the intestine.' Gut-Associated Lymphoid Tissues. Springer Berlin Heidelberg, 2006. 117-136.
Nami, Yousef et al., The Prophylactic Effect of Probiotic Enterococcus lactis IW5 against Different Human Cancer Cells, Frontiers in Microbiology, 2015, vol. 6, Article 1317, pp. 1-11.
Nutsch et al., T cell tolerance and immunity to commensal bacteria. Current Opinion in Immunology. Aug. 2012; 24 (4):385-391. Epub May 19, 2012.
Official Journal of the European Union, Directive 2010/63/EU of the European Parliament and of the Council of Sep. 22, 2010 on the protection of animals used for scientific purposes, Oct. 10, 2010, i. 276/33, pp. 1-47.
Okamoto et al, "Toll-like Receptors (TLRs) are expressed by myeloid leukaemia cell lines, but fail to trigger differentiation in response to the respective TLR ligands" (2009) British Journal of Haematology, 147, 582-590.
Okino, H et al. Release of flagellar filament-hook-rod complex by a *Salmonella typhimurium* mutant defective in the M ring of the basal body (1989) Journal of Bacteriology 171(4):2075-82, DOI:10.1128/jb.171.4.2075-2082.1989.
Pace et al. Macrophage activation: Priming activity from a T-cell hybridoma is attributable to interferon. (1983) PNAS. 80:3782-6.
Palmer, Kelli L.et al, "Comparative Genomics of Enterococci: Variation in Enterococcus faecalis, Clade Structure in E. faecium, and Defining Characteristics of E. gallinarum and E. casseliflavus",. mBio, (2012) vol. 3 Issue 1 e00318-11.
Pettersen EF et al., UCSF Chimera—A Visualization System for Exploratory Research and Analysis (2004), Journal of Computational Chemistry 25(13):1605-12.

(56) References Cited

OTHER PUBLICATIONS

Porte, Rémi et al. "A Toll-Like Receptor 5 Agonist Improves the Efficacy of Antibiotics in Treatment of Primary and Influenza Virus-Associated Pneumococcal Mouse Infections." Antimicrobial agents and chemotherapy vol. 59,10 (2015): 6064-72. doi:10.1128/AAC.01210-15.
Prakash, et al., Complete genome sequences of rat and mouse segmented filamentous bacteria, a potent inducer of th17 cell differentiation. Cell Host & Microbe. Sep. 2011;10(3):273-284.
Rakoff-Nahoum S, Medzhitov R. Toll-like receptors and cancer. Nat Rev Cancer. Jan. 2009;9(1):57-63. doi:10.1038/nrc2541. Epub Dec. 4, 2008. PMID: 19052556.
Rhee et al., Toll-Like Receptor 5 Engagement Modulates Tumor Development and Growth in a Mouse Xenograft Model of Human Colon Cancer. Gastroenterology. Aug. 2008;135(2):518-528, Epub Apr. 23, 2008.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Sczesnak, et al., The genome of th17 cell-inducing segmented filamentous bacteria reveals extensive auxotrophy and adaptations to the intestinal environment. Cell Host Microbe. Sep. 2011;10(3):260-272.
Sfondrini, Lucia et al., Antitumor Activity of the TLR-5 Ligand Flagellin in Mouse Models of Cancer (2006),J Immunol Jun. 1, 2006, 176 (11)6624-6630; DOI: https://doi.org/10.4049/jimmunol.176.11.6624.
Sgadari, C. et al., Interferon-inducible protein-10 identified as a mediator of tumor necrosis in vivo. (1996) PNAS. 93:13791-6.
Sgadari et al. Mig, the Monokine Induced By Interferon-g, Promotes Tumor Necrosis In Vivo. (1997) Blood. 89:2635-43. Nov. 26, 1996.
She et al., Investigation of the Utility of Complementary Electrochemical Detection Techniques to Examine the in Vitro Affinity of Bacterial Flagellins for a Toll-Like Receptor 5 Biosensor (2015)Anal. Chem., 87 (8), pp. 4218-4224.
Shepard et al., B. D. & Gilmore, M. S. In Electroporation and efficient transformation of Enterococcus faecalis grown in high concentrations of glycinein Methods in molecular biology: vol. 47: Electroporation protocols for microorganisms vol. 47 (ed J. A. Nickoloff) 217-226 (Humana Press Inc., 1995).
Smith KD, et al. Toll-like receptor 5 recognizes a conserved site on flagellin required for protofilament formation and bacterial motility. Nat Immunol. Dec. 2003;4(12):1247-53. doi: 10.1038/ni1011. Epub Nov. 16, 2003. Erratum in: Nat Immunol. Apr. 2004;5(4):451. PMID: 14625549.
Song,W., Jeon, Y., Namgung, B. et al. A conserved TLR5 binding and activation hotspot on flagellin. Sci Rep 7, 40878 (2017). https://doi.org/10.1038/srep40878.
Sorroza, Lita et al., A Probiotic Potential of *Enterococcus gallinarum* against *Vibrio anguillarum* Infection, Fish Pathology,2013, vol. 48, No. 1, pp. 9-12.
Steiner, Theodore S., How Flagellin and Toll-Like Receptor 5 Contribute to Enteric Infection (2007). Infection and Immunity 75, 545-552, DOI: 10.1128/IAI.01506-06.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Sun et al., Posttranslational Modification of Flagellin FlaB in Shewanella oneidensis (2013)J Bacteriol. 195(11):2550-61.
Theppangna, Watthana et al., Inhibitory Effects of Enterococcus Strains Obtained from a Probiotic Product on In Vitro Growth of *Salmonella enterica* Serovar Enteritidis Strain IFO3313, Journal of Food Protections, 2006, vol. 69, No. 9, pp. 2258-2262.
Toshkov, Ilia A et al. "Mitigation of Radiation-Induced Epithelial Damage by the TLR5 Agonist Entolimod in a Mouse Model of Fractionated Head and Neck Irradiation." Radiation research vol. 187,5 (2017): 570-580. doi:10.1667/RR14514.1.

Turner, Linda et al. "Visualizing Flagella while Tracking Bacteria." Biophysical journal vol. 111,3 (2016): 630-639. doi:10.1016/j.bpj.2016.05.053.
Uematsu, S., Jang, M., Chevrier, N. et al. Detection of pathogenic intestinal bacteria by Toll-like receptor 5 on intestinal CD11c+ lamina propria cells. Nat Immunol 7, 868-874 (2006).https://doi.org/10.1038/ni1362.
Vijay-Kumar et al., Flagellin Treatment Protects against Chemicals, Bacteria, Viruses, and Radiation. The Journal of Immunology. 2008;180(12):8280-8285.
Yonekura K, et al., "Complete atomic model of the bacterial flagellar filament by electron cryomicroscopy", Nature. Aug. 7, 2003;424(6949):643-50. doi:10.1038/nature01830. PMID: 12904785.
Yoon et al. Structural Basis ofTLR5-Flagellin Recognition and Signaling, (2013). NIH Public Access 335,859-864.
Zheng, Jin Hai, "Two-step enhanced cancer immunotherapy with engineered *Salmonella typhimurium* secreting heterologous flagellin", Science Translational Medicine Feb. 8, 2017:vol. 9, Issue 376,eaak9537, DOI: 10.1126/scitranslmed.aak9537.
Azad, M.B. et al., Probiotic supplementation during pregnancy or infancy for the prevention of asthma and wheeze: systematic review and meta-analysis BMJ 2013; 347 :f6471, Dec. 4, 2013.
Bektas, Arsun et al., Human T cell immunosenescence and inflammation in aging, Journal of leukocyte biology vol. 102,4 (2017): 977-988. doi:10.1189/jlb.3RI0716-335R.
Berthoud et al., MIG (CXCL9) is a more sensitive measure than IFN-γ of vaccine induced T-cell responses in volunteers receiving investigated malaria vaccines (2009) J Immunol Methods 340(1)33-41.
Bertram, J. et al., Establishment of a cloned line of Lewis lung carcinoma cells adapted to cell culture. (1980) Cancer let. 11:63-73.
Bettelli E, Carrier Y, Gao W, Korn T, Strom TB, Oukka M, Weiner HL, Kuchroo VK., Reciprocal developmental pathways for the generation of pathogenic effector TH17 and regulatory T cells. Nature, May 11, 2006;441(7090):235-8. doi: 10.1038/nature04753. Epub Apr. 30, 2006. PMID: 16648838.
Bloch F, et al., Production of TNF-alpha ex vivo is predictive of an immune response to flu vaccination in a frail elderly population, Eur Cytokine Netw. Sep. 1, 2016;27(3):63-67. English. doi: 10.1684/ecn.2016.0378. PMID: 27910810.
Chan, Jason R et al., IL-23 stimulates epidermal hyperplasia via TNF and IL-20R2-dependent mechanisms with implications for psoriasis pathogenesis, The Journal of experimental medicine vol. 203, 12 (2006): 2577-87. doi:10.1084/jem.20060244.
Chen D.K. et al., Evaluation of D-xylose and 1% methyl-alpha-D-glucopyranoside Fermentation Tests for Distinguishing Enterococcus Gallinarum From Enterococcus Faecium, .J. Clin. Microbiol. 2000, 38(10): 3652-3655; PMID: 11015378.
Coffman, Robert L et al., Vaccine adjuvants: putting innate immunity to work, Immunity vol. 33,4 (2010): 492-503. doi:10.1016/j.immuni.2010.10.002.
Collins, M.D., et al., Enterococcus avium nom.rev., comb. nov.; E. casseliflavus nom. rev., comb. nov.; E. durans nom. rev.,comb. nov.; E. gallinarum comb. nov.; and *E. malodoratus* sp. nov. (1984) Int J Syst Evol Microbiol. 34: 220-223. First Published: Apr. 1, 1984.irst Published: Apr. 1, 1984.
Darlington, G.J., Liver Cell Lines. (1987) Meth Enzymol. 151:19-38.
Didierlaurent AM, et al., Enhancement of adaptive immunity by the human vaccine adjuvant AS01 depends on activated dendritic cells. J Immunol. Aug. 15, 2014;193(4):1920-30. doi: 10.4049/jimmunol.1400948. Epub Jul. 14, 2014. PMID: 25024381.
Eckburg, PB. et al., Diversity of the human intestinal microbial flora, Science. Jun. 10, 2005;308(5728):1635-8. Epub Apr. 14, 2005.
Eurasian Search Report dated May 23, 2020 for Application Serial No. 202090107 (8 pages).
Fernández-Ruiz M, et al., Baseline serum interleukin-6 to interleukin-2 ratio is associated with the response to seasonal trivalent influenza vaccine in solid organ transplant recipients, Vaccine.Dec. 16, 2015;33(51):7176-7182. doi: 10.1016/j.vaccine.2015.10.134. Epub Nov. 10, 2015. PMID: 26555352.

(56) References Cited

OTHER PUBLICATIONS

Fülöp T, Dupuis G, Witkowski JM, Larbi A., The Role of Immunosenescence in the Development of Age-Related Diseases. Rev Invest Clin. Mar.-Apr. 2016;68(2):84-91. PMID: 27103044.

Fraietta, Joseph et al. Jan. (2018). Determinants of response and resistance to CD19 chimeric antigen receptor (CAR) T cell therapy of chronic lymphocytic leukemia. Nature Medicine. 24. 10.1038/s41591-018-0010-1.

Frank, D. et al., Molecular-phylogenetic characterization of microbial community imbalances in human inflammatory bowel diseases. 2007. PNAS. 104(34):13780-5.online Aug. 15, 2007.

Fulop, Tamas et al., Immunosenescence and Cancer (2013) Critical Reviews in Oncogenesis 2013;18(6):489-513.

Fulop, Tamas et al., Immunosenescence and Inflamm-Aging As Two Sides of the Same Coin: Friends or Foes?., Frontiers in immunology vol. 8 1960. Jan. 10, 2018, doi:10.3389/fimmu.2017.01960.

Gaurand Aggarwal, Regulation of proliferation, survival and apoptosis by members of the TNF superfamily* (2003).Biochem Pharmacol. ;66(8):1403-8.

GenBank Accession No. KC456574.1 (May 3, 2013) Enterococcus casseliflavus strain ALK061 16S ribosomal RNA gene, partial sequence [Enterococcus casseliflavus], May 23, 2020:https://www.ncbi.nlm.nih.govinuccore/KC456574.1.

Glenn, Justin D, and Katharine A Whartenby, Mesenchymal stem cells: Emerging mechanisms of immunomodulation and therapy. World journal of stem cells vol. 6,5 (2014): 526-39. doi:10.4252/wjsc.v6.i5.526.

Goldin, B.R. et al., Clinical indications for probiotics: an overview. Clin Infect Dis. Feb. 1, 2008;46 Suppl 2:S96-100; discussion S144-51. doi: 10.1086/523333.

Heng, Boon Chin et al., Strategies for directing the differentiation of stem cells intothe cardiomyogenic lineage in vitro (2004) Cardiovasc Res. Apr. 1, 2004;62(1):34-42.

Kailasapathy, K., Microencapsulation of Probiotic Bacteria: Technology and Potential Applications. Curr. Issues Intest. Microbiol. (2002) 3: 39-48.

Kawai and Akira, "Signaling to NF-kB by Toll-like receptors" (2007) Trends in Molecular Medicine 13, 11, 460-469.

Klein, G., Taxonomy, Ecology and Antibiotic Resistance of Enterococci From Food and the Gastro-Intestinal Tract, Int. J. Food Microbiol. 2003, 88(2-3): 123-131; PMID: 14596985.

Knudsen, Niels Peter H et al., Different human vaccine adjuvants promote distinct antigen-independent immunological signatures tailored to different pathogens., Scientific reports vol. 6 19570. Jan. 21, 2016, doi:10.1038/srep19570.

Laukova A. et al., Characteristics of Enterococci and Staphylococci Isolated From the Crop and Caecum of Japanese Quails Exposed to Microgravity Conditions, Vet. Med. (Praha).1995, 40(10): 317-321, PMID: 8659081.

Laukova A., The Effect of Culture Media on Bacteriocin Production in Various Strains of Bacteria, Vet. Med. (Praha). 1992, 37(12): 661-666; PMID: 1297243.

Leal, I S et al., Interleukin-6 regulates the phenotype of the immune response to a tuberculosis subunit vaccine, Immunology vol. 103,3 (2001): 375-81. doi:10.1046/j.1365-2567.2001.01244.x.

Leslie, et al., Trehalose and sucrose protect both membranes and proteins in intact bacteria during drying. (1995) Appl. Environ. Microbiol. 61, 3592-3597.

Li et al, Aluminum Hydroxide Adjuvants Activate Caspase-1 and Induce IL-1β andIL-18 Release (2007) J Immunol, 178(8),5271-5276.

Lim, Jae Sung et al., Flagellin-dependent TLR5/caveolin-1 as a promising immune activator in immunosenescence, Aging cell vol. 14,5 (2015): 907-15. doi:10.1111/acel.12383.

Machiels, K., A decrease of the butyrate-producing species Roseburia hominis and Faecalibacterium prausnitzii defines dysbiosis in patients with ulcerative colitis, Gut. Aug. 2014;63(8):1275-83. doi: 10.1136/gutjnl-2013-304833. Epub Sep. 10, 2013.

MacPherson, AJ. et al., IgA responses in the intestinal mucosa against pathogenic and non-pathogenic microorganisms, Oct. 2001. 3(12). 1021-1035.

Martinon, Fabio et al., The Inflammasome: A Molecular Platform Triggering Activation of Inflammatory Caspases and Processing of proIL-β, (2002) Mol Cell .;10(2):417-26.

Masco, L., et al., Identification of Bifidobacterium Species Using rep-PCR Fingerprinting. Systematic and Applied Microbiology 26(4):557-63 Nov. 2003.

Mazmanian, SK., An immunomodulatory molecule of symbiotic bacteria directs maturation of the host immune system, Cell. Jul. 15, 2005;122(1):107-18.

Mitropoulou, G. et al., Immobilization Technologies in Probiotic Food Production. (2013) Journal Nutr Metab. (2013) 716861.

Miyamoto-Shinohara et al., Survival of freeze-dried bacteria. J Gen Appl Microbiol 54(1):9-24 (2008).

Mohanty, Subhasis et al., Prolonged proinflammatory cytokine production in monocytes modulated by interleukin 10 after influenza vaccination in older adults, The Journal of infectious diseases vol. 211,7 (2015): 1174-84. doi: 10.1093/infdis/jiu573.

Morel S, et al., Adjuvant System AS03 containing α-tocopherol modulates innate immune response and leads to improved adaptive immunity, Vaccine. Mar. 16, 2011;29(13):2461-73. doi: 10.1016/j.vaccine.2011.01.011. Epub Jan. 20, 2011. PMID:21256188.

Mori, Andres et al., The vaccine adjuvant alum inhibits IL-12 by promoting PI3 kinase signaling while chitosan does not inhibit IL-12 and enhances Th1 and Th17 responses (2012), Eur J Immunol42, 2709-2719.

Murphy, Craig A et al., Divergent pro-and anti inflammatory roles for IL-23 and IL-12 in joint autoimmune inflammation, The Journal of experimental medicine vol. 198,12 (2003): 1951-7. doi:10.1084/jem.20030896.

Olafsdottir, Thorunn et al., Molecular signatures of vaccine adjuvants, Vaccine 33(40)5302-5307.

Park, Matthew K et al., The CXC Chemokine Murine Monokine Induced by IFN-γ (CXC Chemokine Ligand 9) Is Made by APCs, Targets Lymphocytes Including Activated B Cells, and Supports Antibody Responses to a Bacterial Pathogen In Vivo, J Immunol Aug. 1, 2002, 169 (3)1433-1443; DOI: https://doi.org/10.4049/jimmunol.169.3.1433.

Rashidi, Armin et al., Pretransplant Gut Colonization with Intrinsically Vancomycin-Resistant Enterococci (E. gallinarum and E. casseliflavus) and Outcomes of Allogeneic Hematopoietic Cell Transplantation, Biology of blood and marrow transplantation : journal of the American Society for Blood and Marrow Transplantation vol. 24,6 (2018): 1260-1263. doi:10.1016/j.bbmt.2018.01.025.

Ren, Ke, and Richard Torres, Role of interleukin-1beta during pain and inflammation, Brain research reviews vol. 60,1 (2009): 57-64. doi:10.1016/j.brainsrev.2008.12.020.

Rockwell, S.C. et al., Characteristics of a Serially Transplanted Mouse Mammary Tumor and Its Tissue-Culture-Adapted Derivative. (1972) J Natl Cancer Inst. 49:735-49.

Simpson-Herren, L. et al., Kinetic parameters and growth curves for experimental tumor systems. Cancer Chemother Rep. Jun. 1970;54(3):143-74.

Smith and Waterman, Comparison of biosequences, Advances in Applied Mathematics, vol. 2, Issue 4, Dec. 1981, pp. 482-489.

Spor, A. et al., Unravelling the effects of the environment and host genotype on the gut microbiome. Nat Rev Microbiol. Apr. 2011;9(4):279-90. doi: 10.1038/nrmicro2540.

Srutkova, D. et al., Efficiency of PCR-based methods in discriminating Bifidobacterium longum ssp. *longum* and Bifidobacterium longum ssp. *infantis* strains of human origin. J Microbiol Methods. Oct. 2011;87(1):10-6. doi: 10.1016/j.mimet.2011.06.014. Epub Jul. 2, 2011.

Strobel, H.J. Basic laboratory culture methods for anaerobic bacteria. Methods Mol Biol. 2009;581:247-61. doi: 10.1007/978-1-60761-214-8_16.

Su, Baowei et al., The effects of IL-6 and TNF-alpha as molecular adjuvants on immune responses to FMDV and maturation of dendritic cells by DNA vaccination. (2008)Vaccine. 26. 5111-22. 10.1016/j.vaccine.2008.03.089.

(56) References Cited

OTHER PUBLICATIONS

Tanaka, Toshio et al. "IL-6 in inflammation, immunity, and disease." Cold Spring Harbor perspectives in biology vol. 6,10 a016295. Sep. 4, 2014, doi:10.1101/cshperspect.a016295.

Van De Bogert, et al., Immunomodulatory properties of *Streptococcus* and veillonella isolates from the human small intestine microbiota, PLOS One, Dec. 2014: 1-20, DOI:10.1371/journal.pone.0114277.

Wang, Xia, and Yong Lin, Tumor necrosis factor and cancer, buddies or foes?., Acta pharmacologica Sinica vol. 29,11 (2008): 1275-88. doi: 10.1111/j.1745-7254.2008.00889.x.

Weinberger B., Adjuvant strategies to improve vaccination of the elderly population. Curr Opin Pharmacol. Aug. 2018;41:34-41. doi: 10.1016/j.coph.2018.03.014. Epub Apr. 17, 2018. PMID: 29677646.

Workman et al., Guidelines for the welfare and use of animals in cancer research (2010) Br. J. Cancer. 102:1555-77.

Zhou, Qing et al., Program death-1 signaling and regulatory T cells collaborate to resist the function of adoptively transferred cytotoxic T lymphocytes in advanced acute myeloid leukemia, Blood vol. 116,14 (2010): 2484-93. doi:10.1182/blood-2010-03-275446.

Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.

Patel., R. et al., Determination of 16S rRNA sequences of enterococci and application to species identification of nonmotile enterococcus gallinarum isolates. Journal of clinical microbiology, 1998; 36(11):3399-3407.

Sivieri, K. et al., Probiotic enterococcus faecium CRL 183 inhibit chemically induced colon cancer in male wistar rats. Eur Food Res Technol. 2008; 228:231-237.

Vetrovsky, T. and Baldrian, P., The variability of the 16S rRNA gene in bacterial genomes and its consequences for bacterial community analyses. Plos One. Feb. 2013; 8(2): e57923.

International Search Report dated Jun. 18, 2019 for International Application Serial No. PCT/EP2019/056894, 5 pages.

Roman, Lorena et al: "The effect of probiotic Enterococcus gallinarum L-1 on the innate immune parameters of outstanding species to marine aquaculture", Journal of Applied Animal Research, vol. 43, No. 2, Jul. 18, 2014(Jul. 18, 2014), pp. 177-183, XP055525525,IN, ISSN: 0971-2119, DOI:10.1080/09712119.2014. 928635.

* cited by examiner

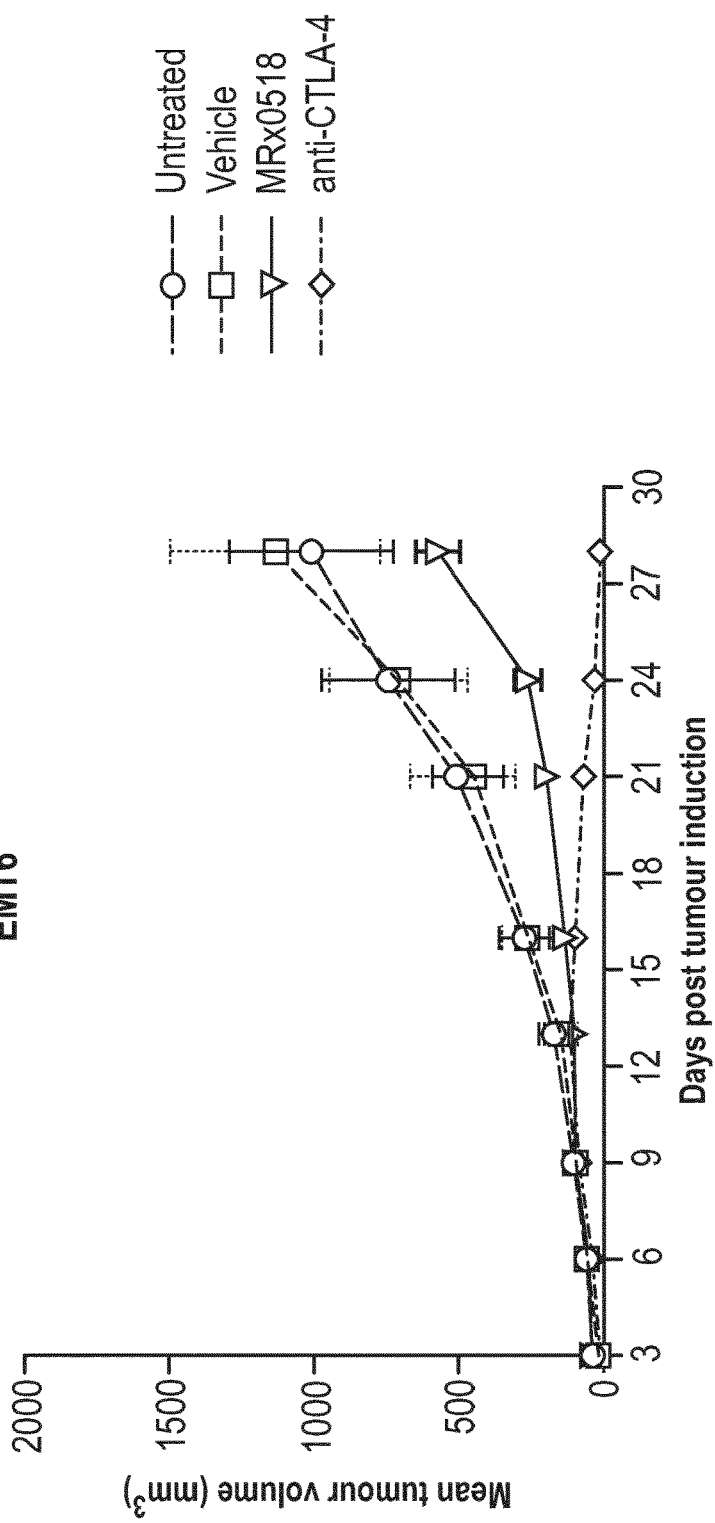

FIG. 1B
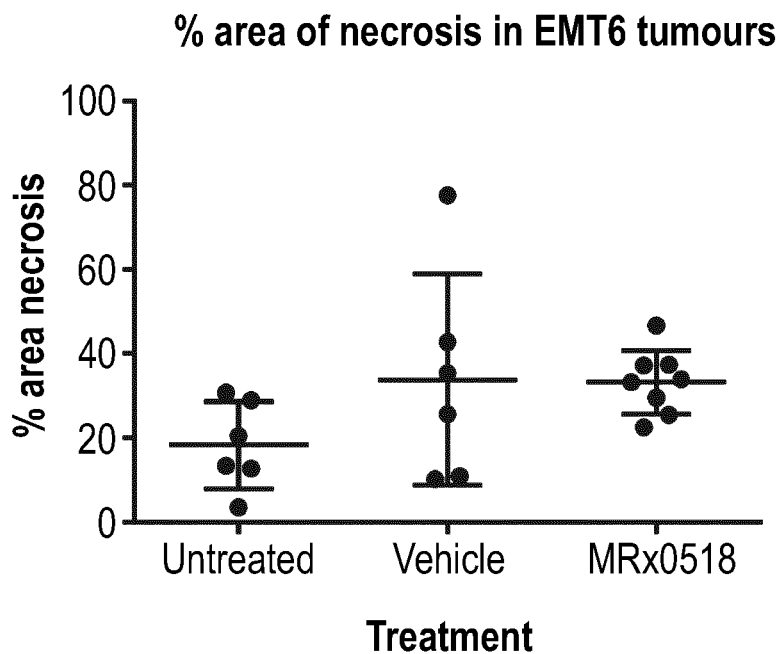
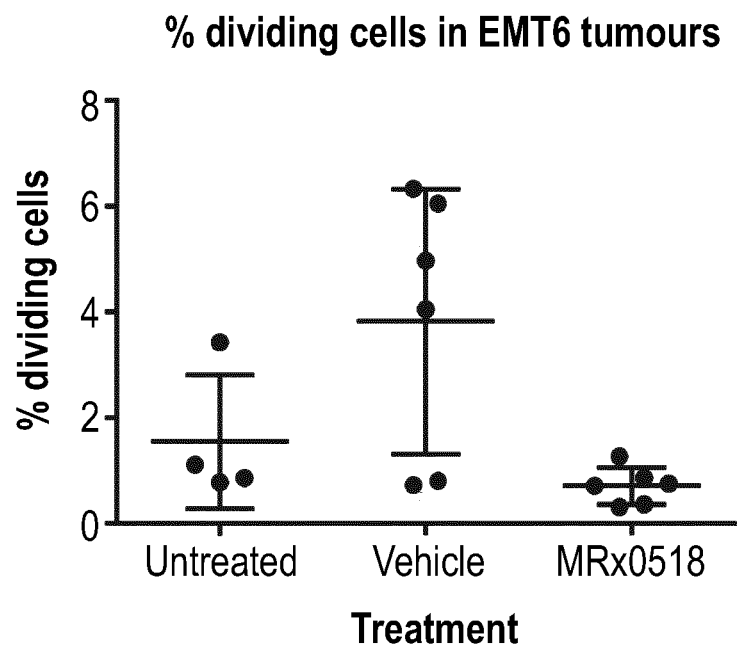

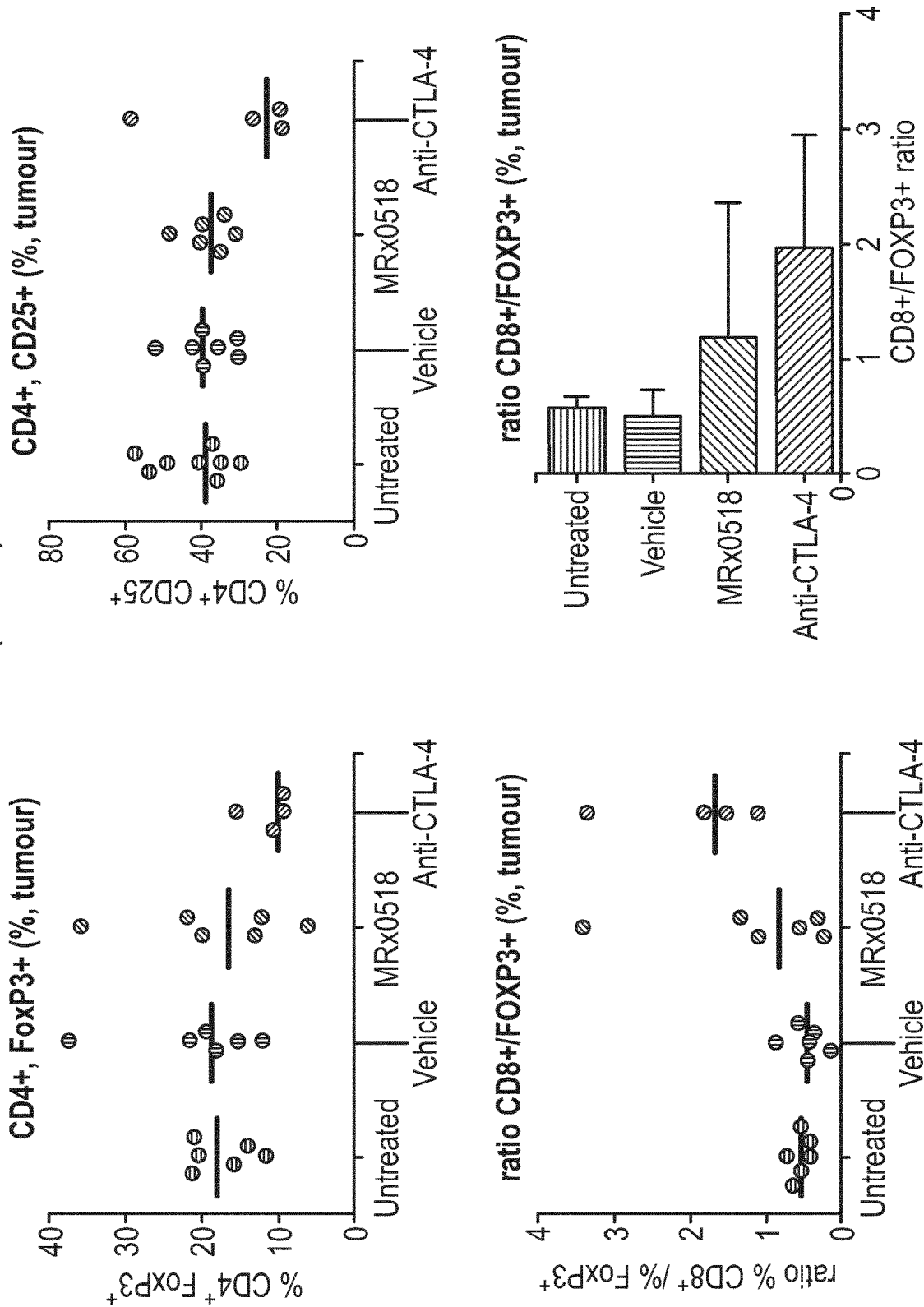

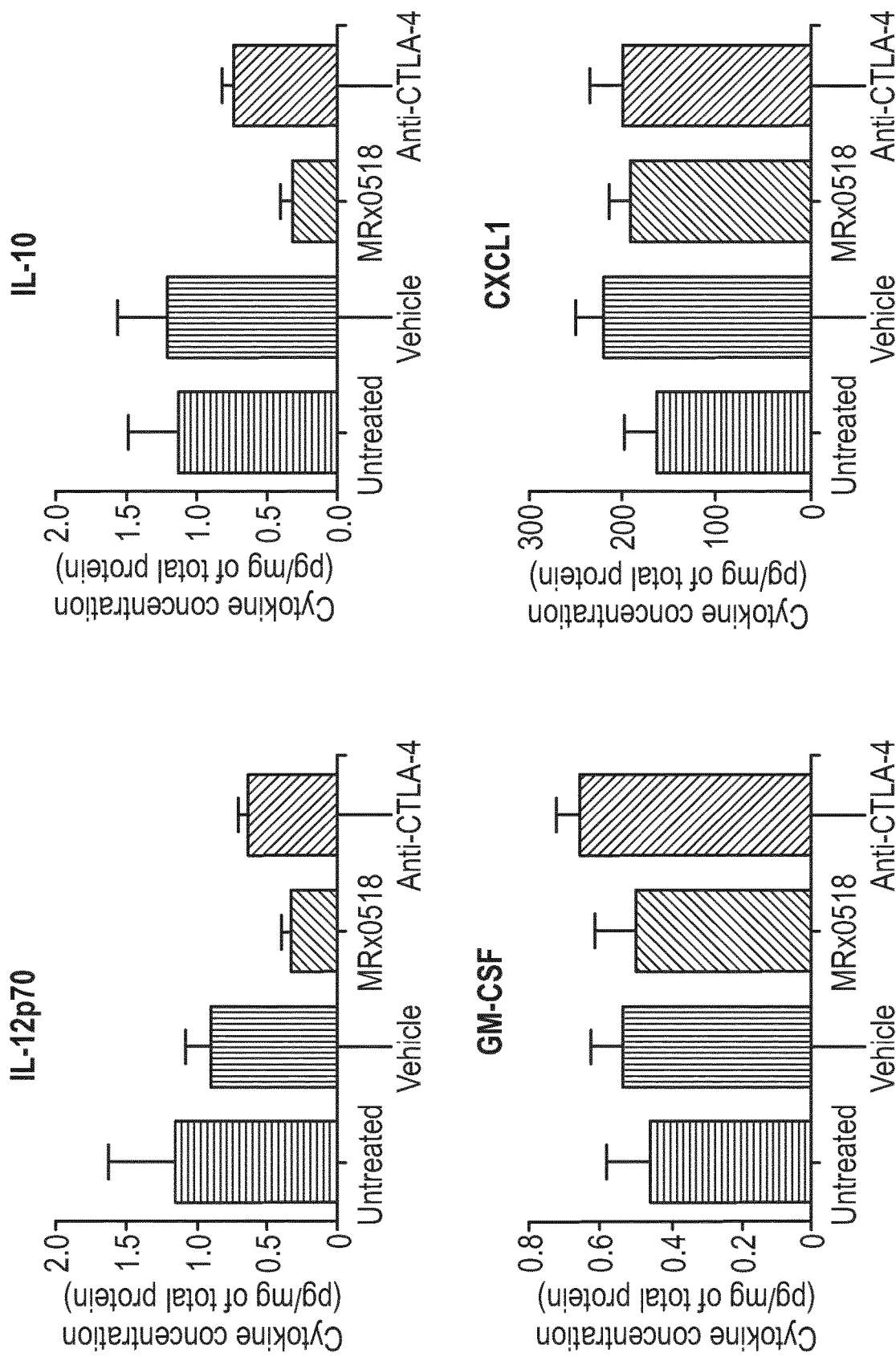
FIG. 1D(contd.)

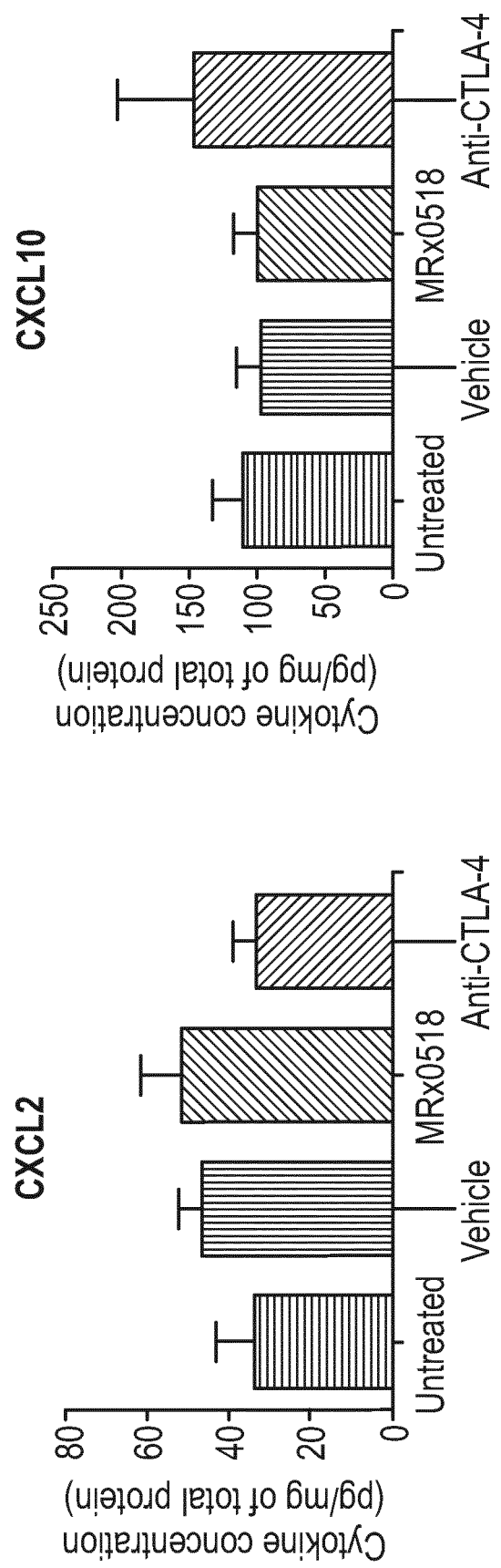
FIG. 1D(contd.)

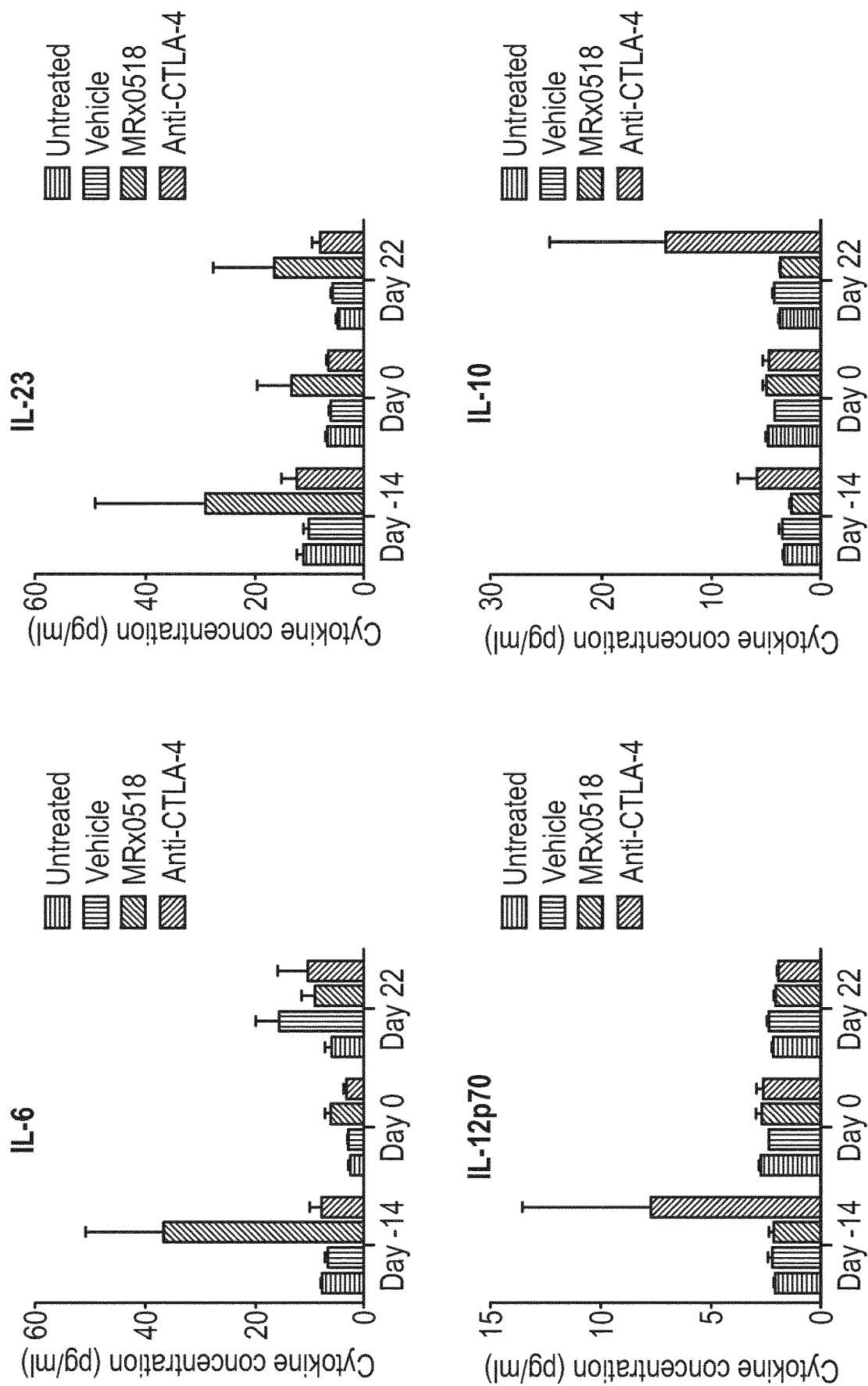
FIG. 1E (contd.)

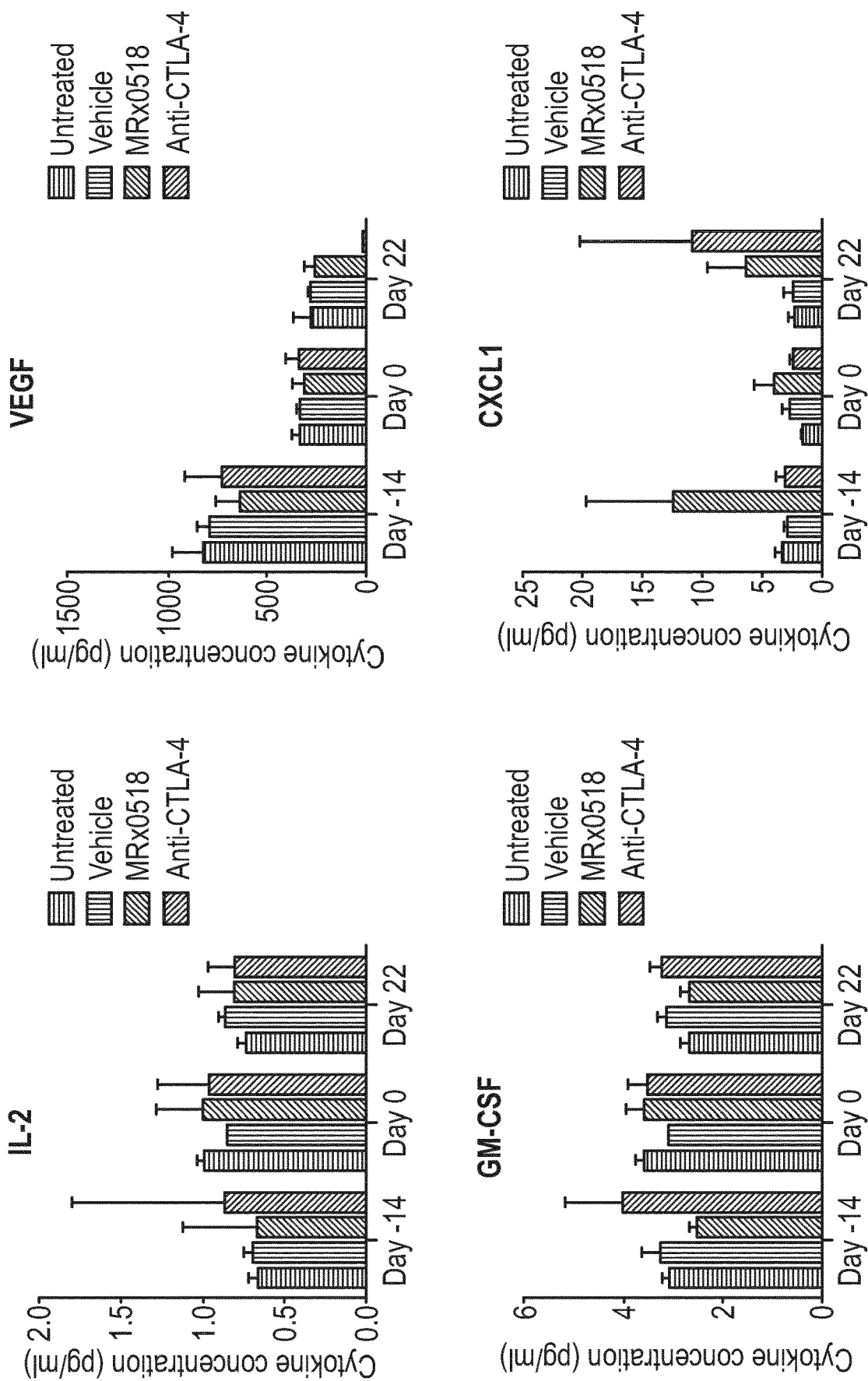
FIG. 1E(contd.)

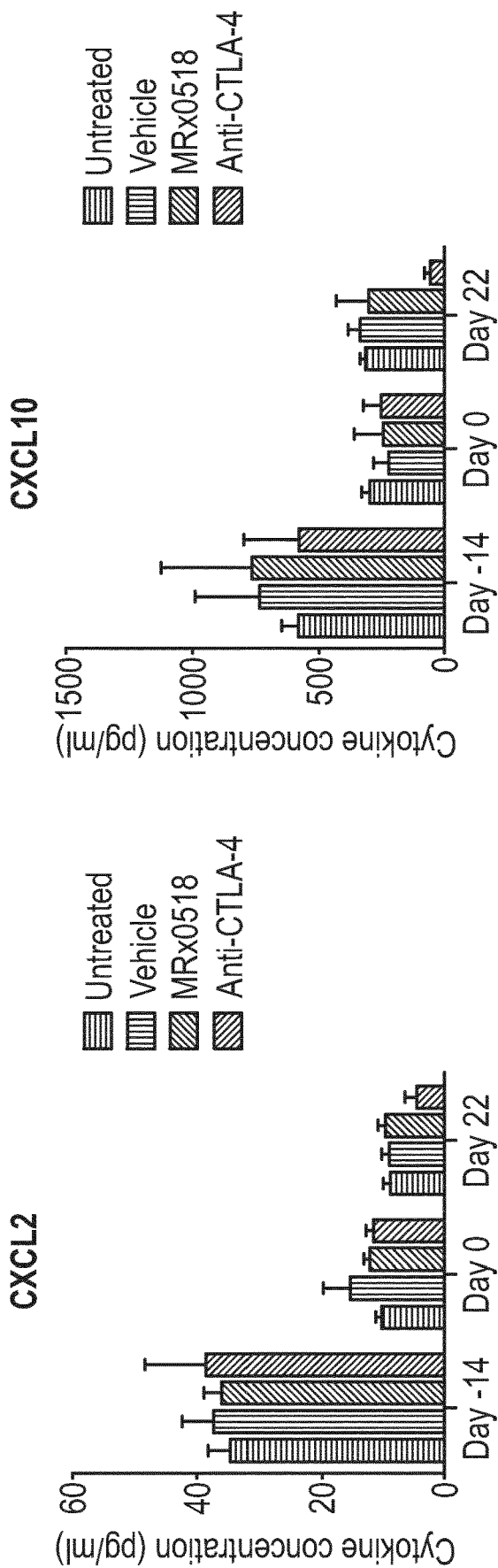
FIG. 1E(contd.)

Percentage of fields view showing more than 3 CD8α+ cells in crypt region

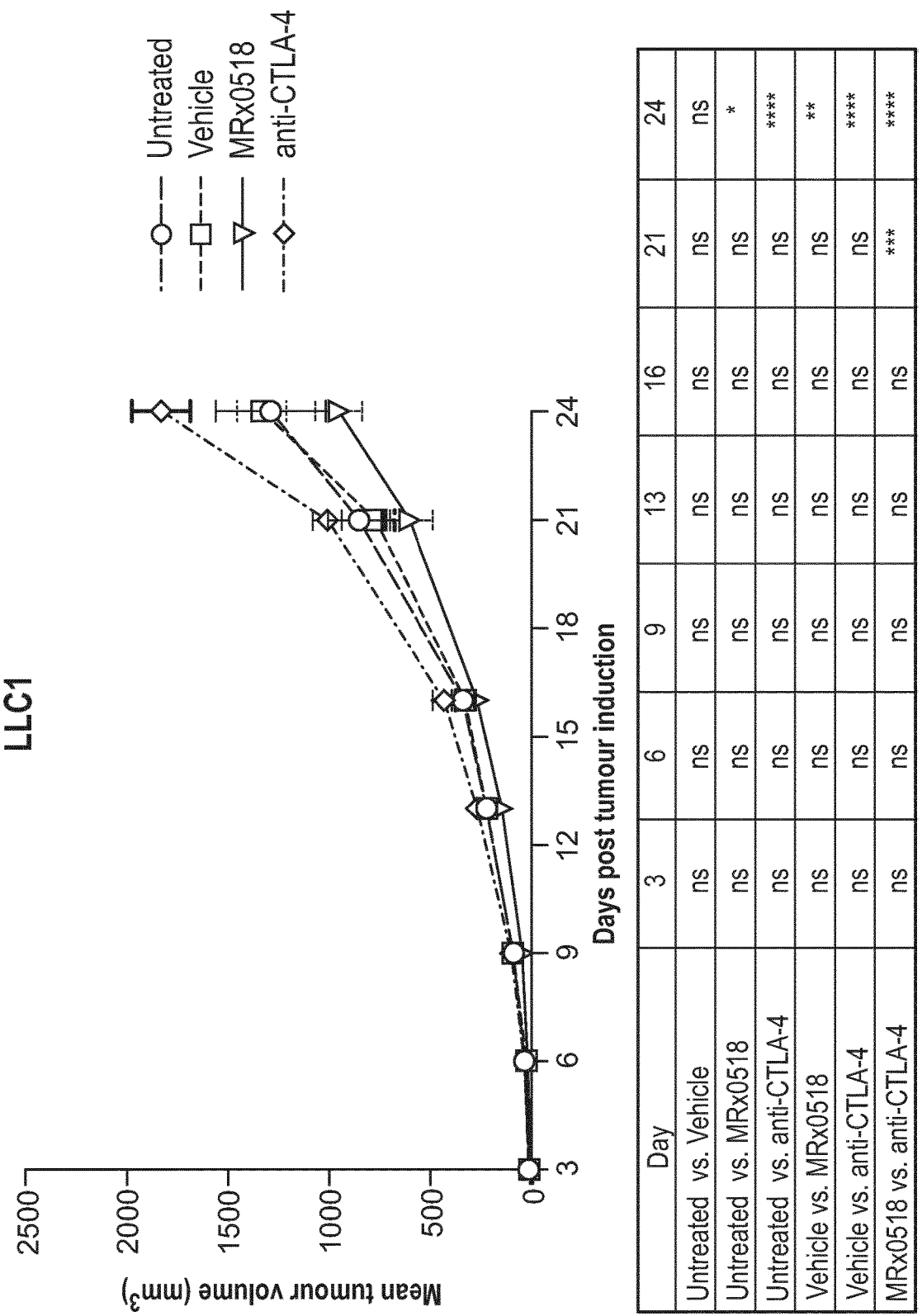

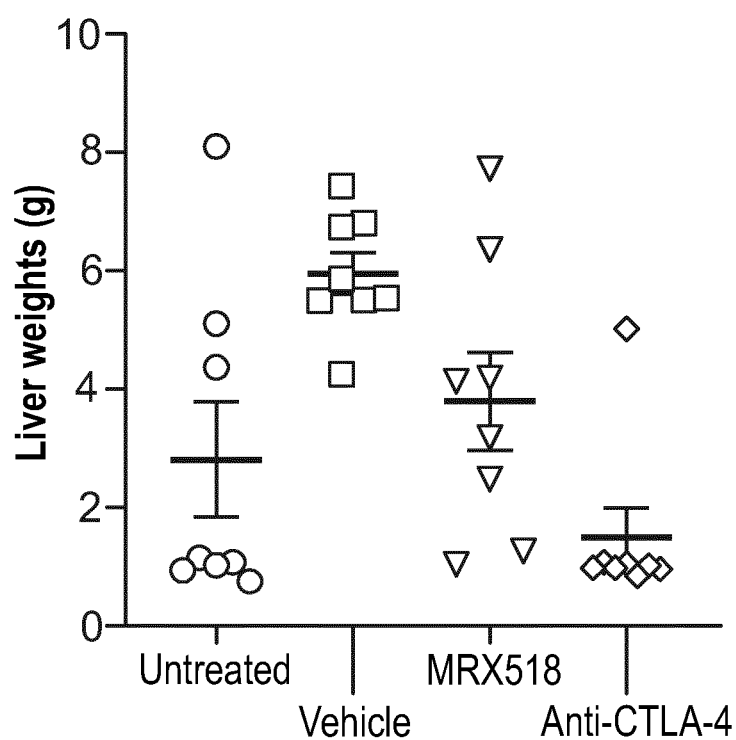

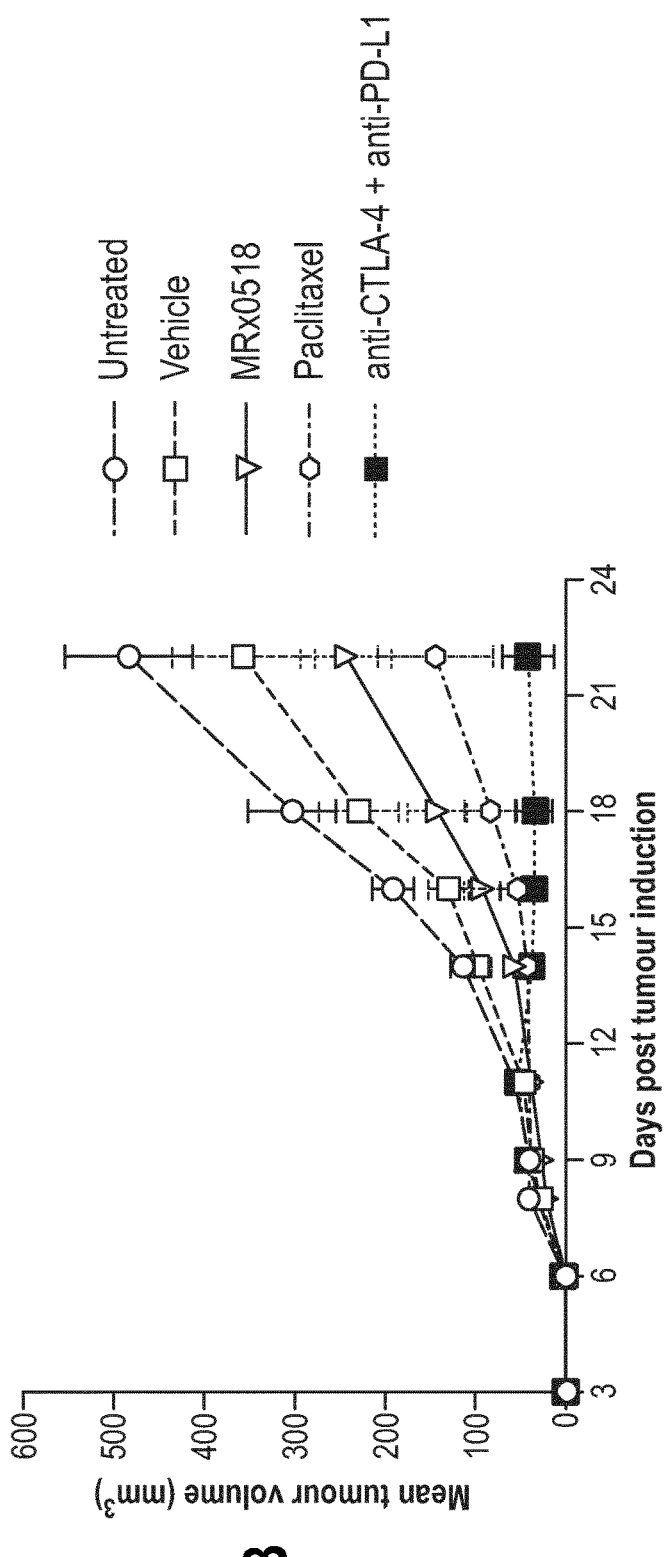
FIG. 3B RENCA

Negative control

Positive control

Addition of MRX518

Addition of MRX518 and LPS

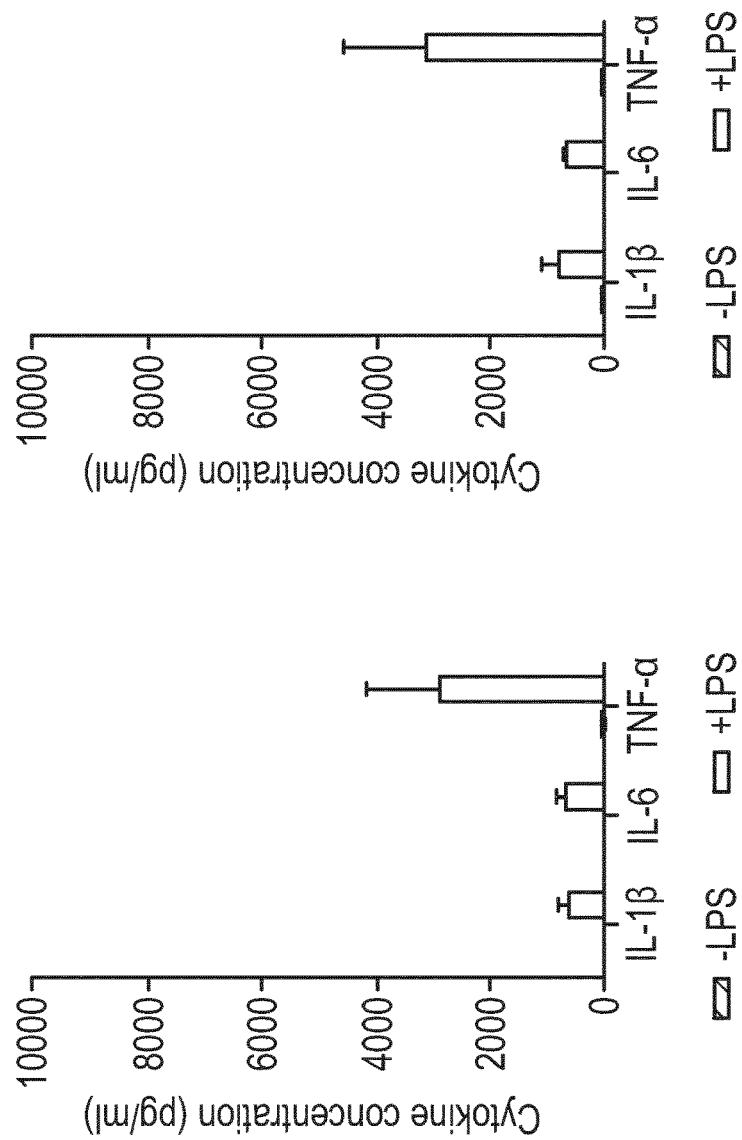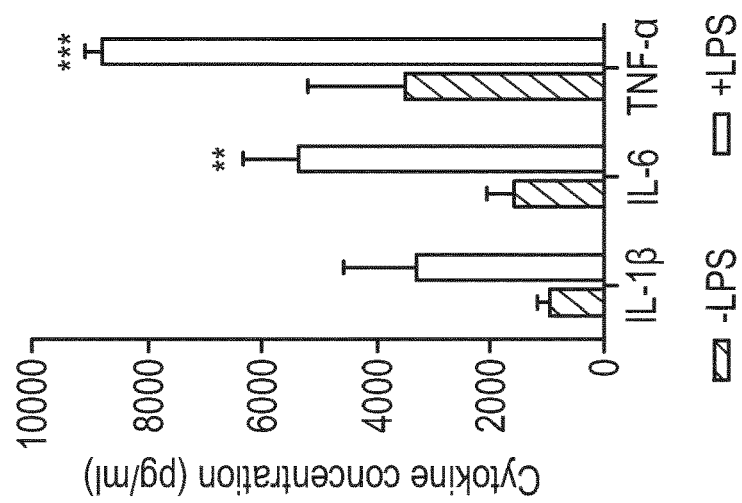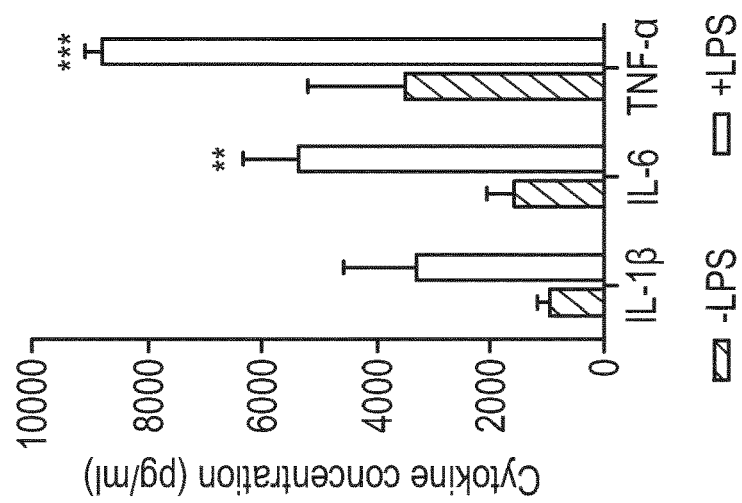

FIG. 6
Macrophages
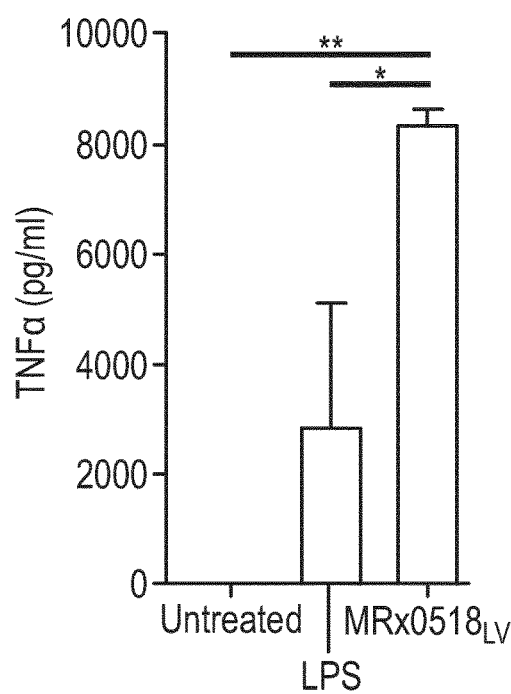
FIG. 7
DCs
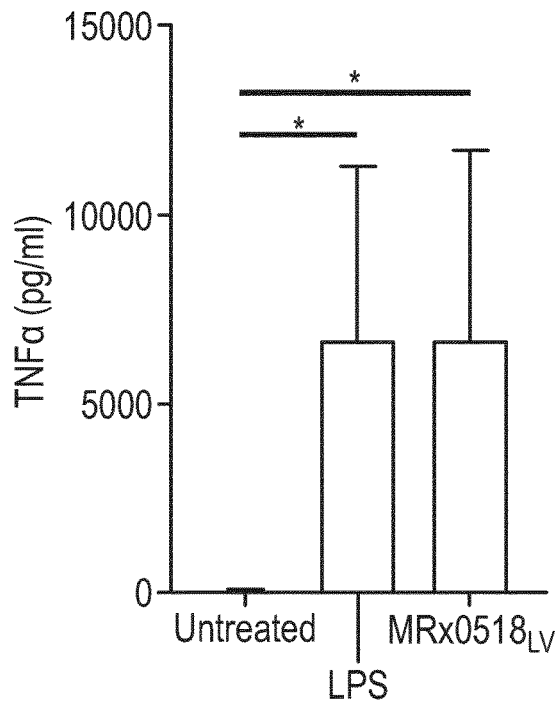
FIG. 8
IL-12p70
Macrophages
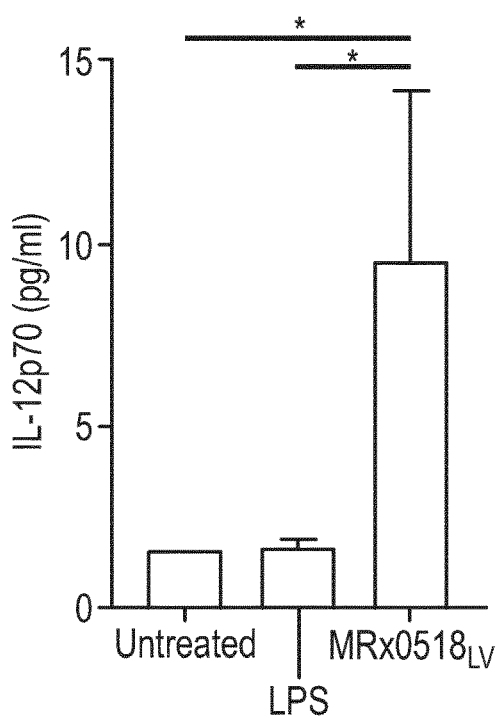
DCs
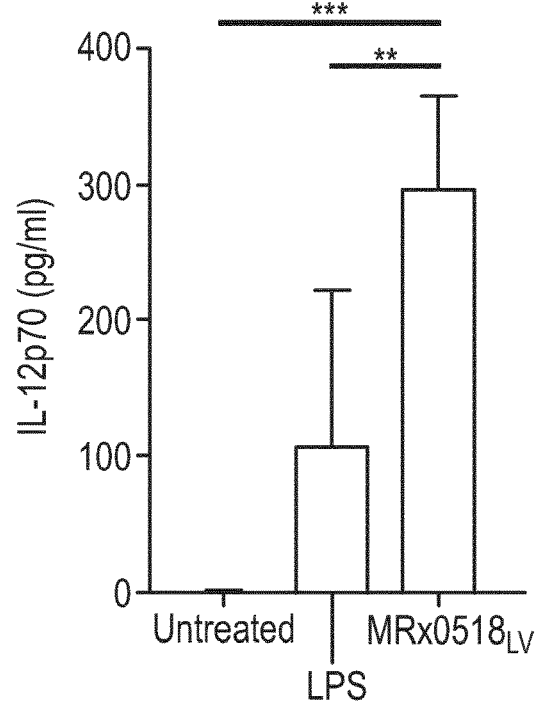

NF-kB

FIG. 15
TLR5
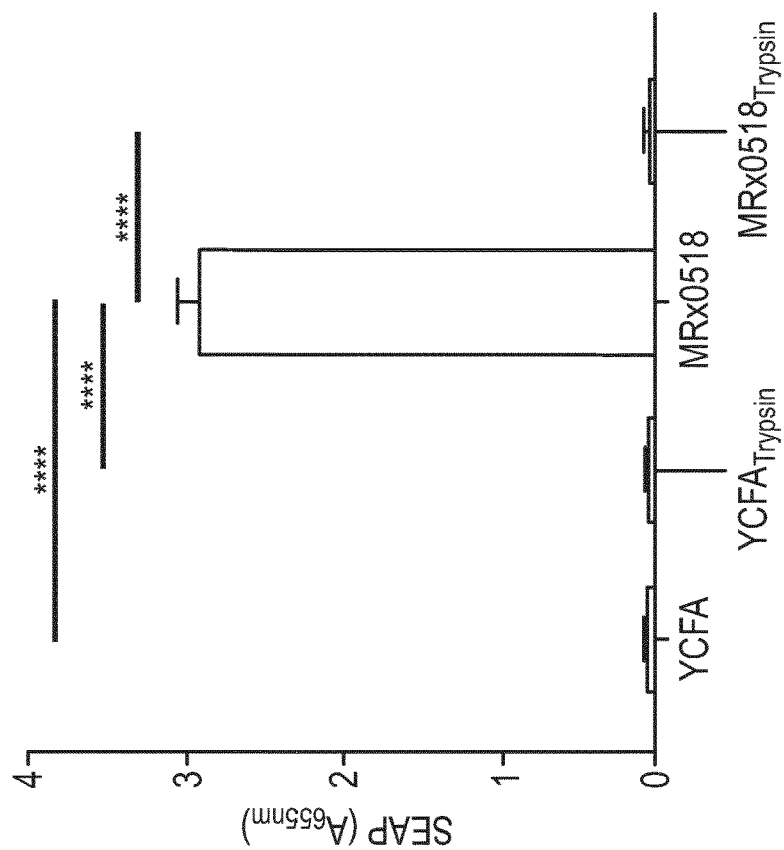
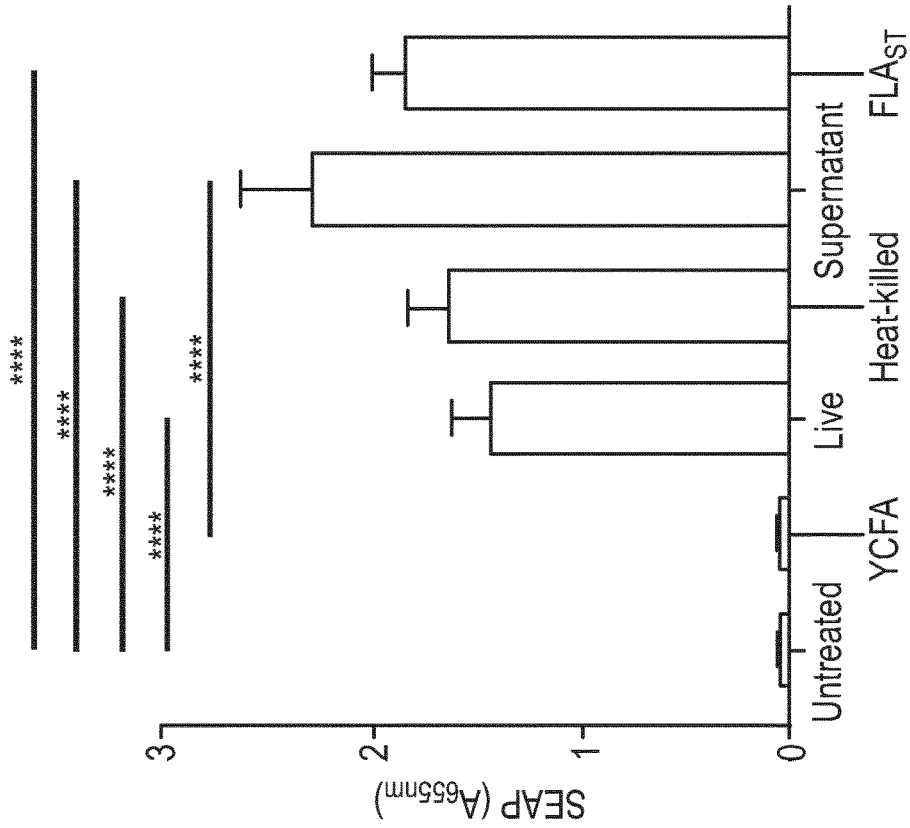

EMT6

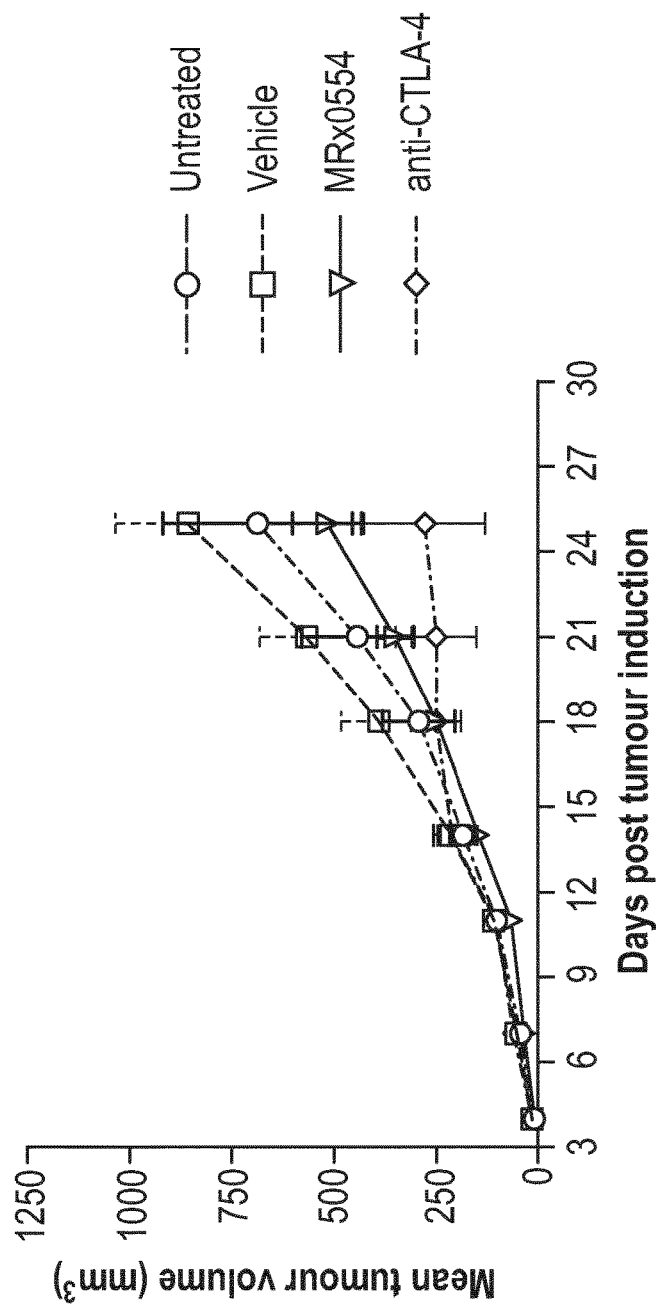

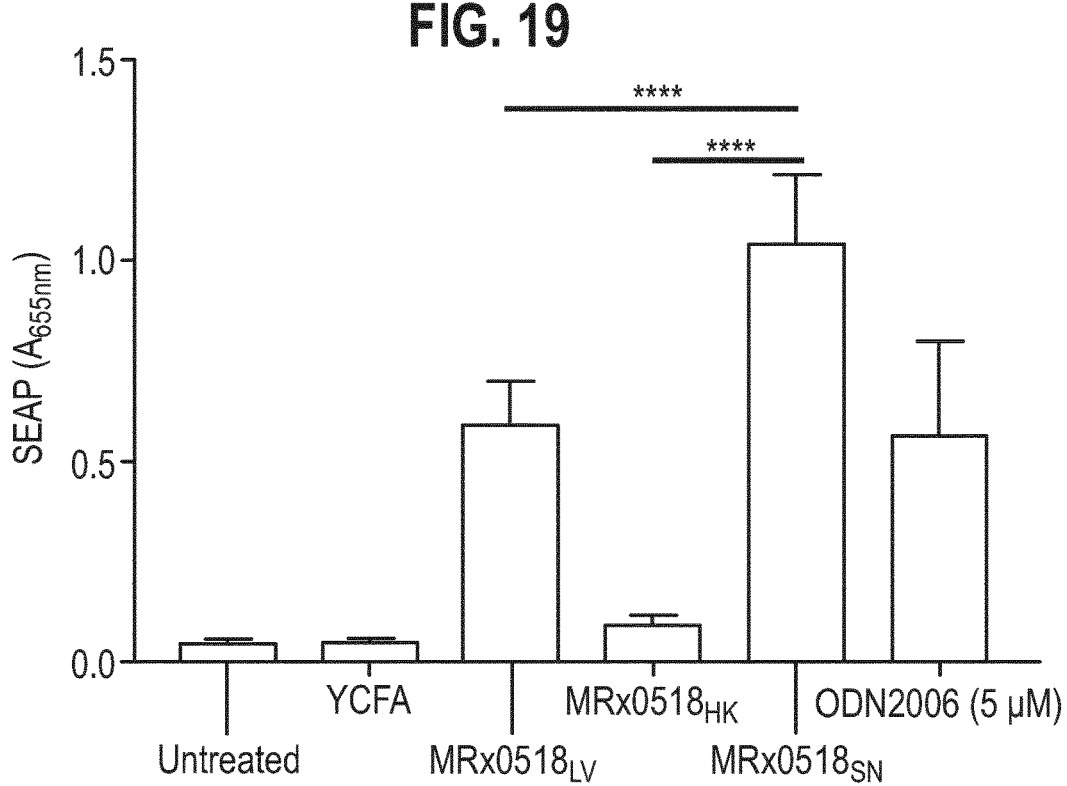
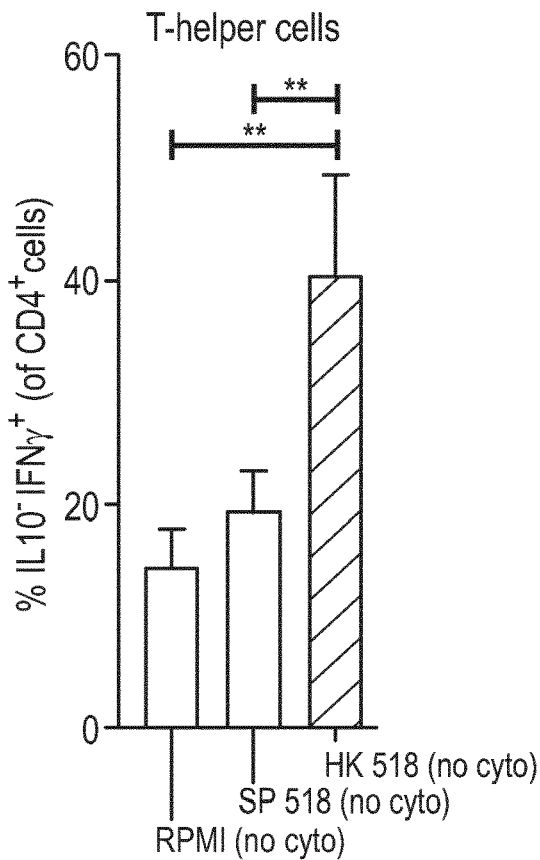
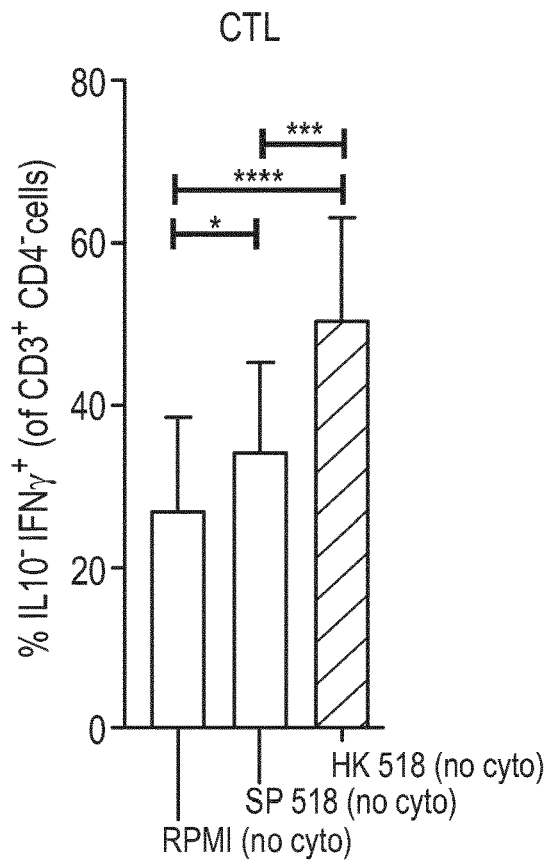

PBMC cytokine production

Splenocyte cytokine production

THP-1 cytokine production

Caco-2 cytokine expression

Cytokines secretion from mouse splenocytes (N=3)

MTT assay Mouse spleoncytes N=4

Activation of NFkB-AP1 promoter in HEKhNOD2 (N=3)

Activation of NF-κβ-AP1 promoter in HEKTLR4 N=3

Activation of NF-κβ-AP1 promoter in HEKTLR9 N=3

Activation of NF-κβ-AP1 promoter in HEKTLR5 N=3

FIG. 23 Cell types modulated by MRx0518
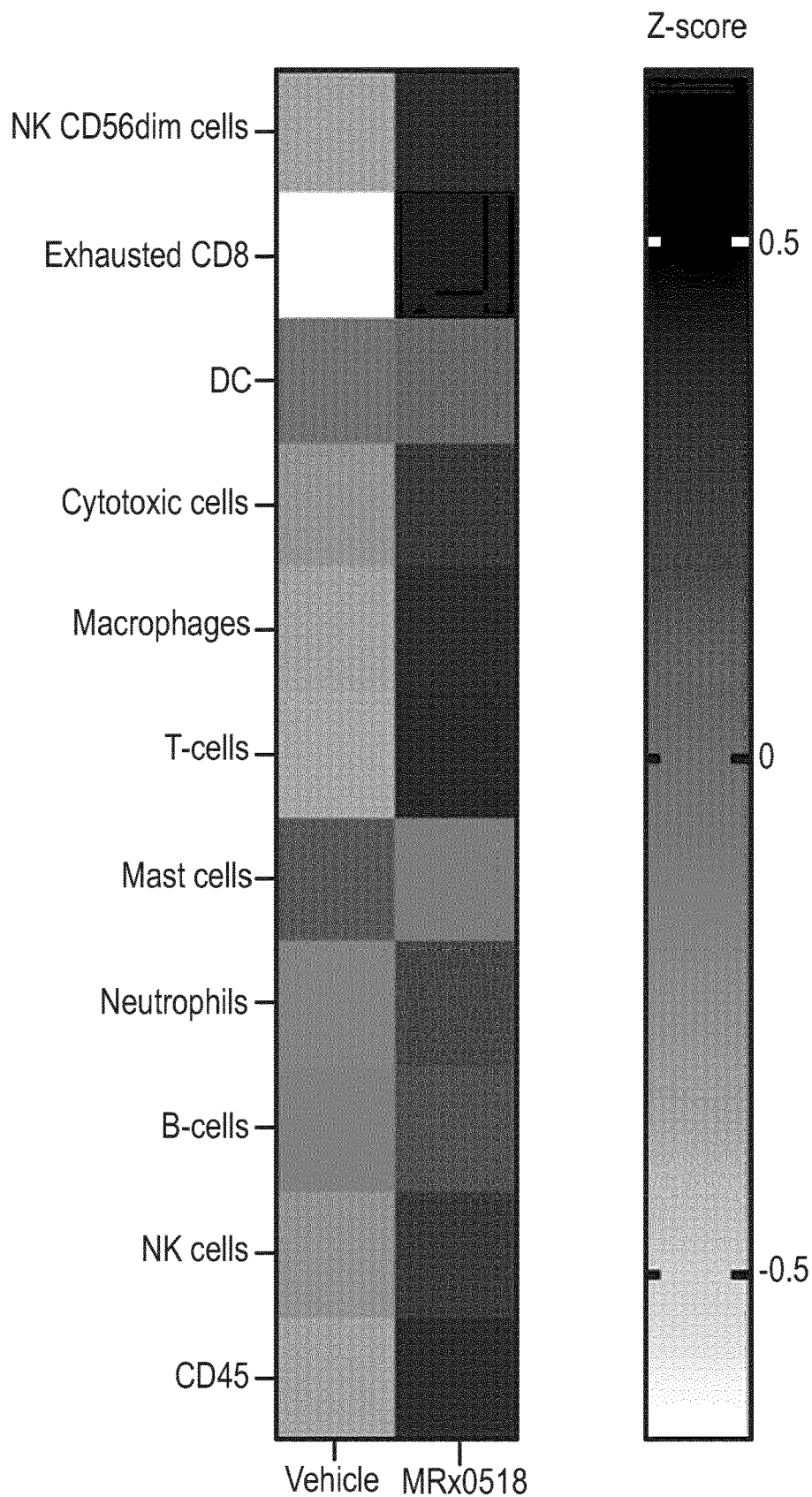

SEQUENCE LISTING

```
<160> NUMBER OF SEQ ID NOS: 4

<210> SEQ ID NO 1
<211> LENGTH: 1506
<212> TYPE: DNA
<213> ORGANISM: Enterococcus gallinarum

<400> SEQUENCE: 1
taatacatgc aagtcgaacg cttttctttt caccggagct tgctccaccg aaagaaaaag      60
agtggcgaac gggtgagtaa cacgtgggta acctgcccat cagaagggga taacacttgg     120
aaacaggtgc taataccgta taacactatt ttccgcatgg aagaaagttg aaaggcgctt     180
ttgcgtcact gatggatgga cccgcggtgc attagctagt tggtgaggta acggctcacc     240
aaggccacga tgcatagccg acctgagagg gtgatcggcc acactgggac tgagacacgg     300
cccagactcc tacgggaggc agcagtaggg aatcttcggc aatggacgaa agtctgaccg     360
agcaacgccg cgtgagtgaa gaaggttttc ggatcgtaaa actctgttgt tagagaagaa     420
caaggatgag agtagaacgt tcatcccttg acggtatcta accagaaagc cacggctaac     480
tacgtgccag cagccgcggt aatacgtagg tggcaagcgt tgtccggatt tattgggcgt     540
aaagcgagcg caggcggttt cttaagtctg atgtgaaagc ccccggctca accggggagg     600
gtcattggaa actgggagac ttgagtgcag aagaggagag tggaattcca tgtgtagcgg     660
tgaaatgcgt agatatatgg aggaacacca gtggcgaagg cggctctctg gtctgtaact     720
gacgctgagg ctcgaaagcg tggggagcga acaggattag ataccctggt agtccacgcc     780
gtaaacgatg agtgctaagt gttggagggt ttccgccctt cagtgctgca gcaaacgcat     840
taagcactcc gcctgggag tacgaccgca aggttgaaac tcaaaggaat tgacggggc      900 ccgcacaagc ggtggagcat gtggtttaat tcgaagcaac gcgaagaacc ttaccaggtc     960
ttgacatcct ttgaccactc tagagataga gcttcccctt cggggggcaaa gtgacaggtg    1020
```

```
gtgcatggtt gtcgtcagct cgtgtcgtga gatgttgggt taagtcccgc aacgagcgca   1080
acccttattg ttagttgcca tcatttagtt gggcactcta gcgagactgc cggtgacaaa   1140
ccggaggaag gtggggatga cgtcaaatca tcatgcccct tatgacctgg gctacacacg   1200
tgctacaatg gaagtacaa cgagttgcga agtcgcgagg ctaagctaat ctcttaaagc    1260
ttctctcagt tcggattgta ggctgcaact cgcctacatg aagccggaat cgctagtaat   1320
cgcggatcag cacgccgcgg tgaatacgtt cccgggcctt gtacacaccg cccgtcacac   1380
cacgagagtt tgtaacaccc gaagtcggtg aggtaacctt tttggagcca gccgcctaag   1440
gtgggataga tgattggggt gaagtcgtaa caaggtagcc gtatcggaag gtgcggctgg   1500
atcacc                                                              1506

<210> SEQ ID NO 2
<211> LENGTH: 1444
<212> TYPE: DNA
<213> ORGANISM: Enterococcus gallinarum
<220> FEATURE:
<223> OTHER INFORMATION: Enterococcus gallinarum strain MRx0518

<400> SEQUENCE: 2
tgctatacat gcagtcgaac gcttttctct tcaccggagc ttgctccacc gaaagaaaaa     60
gagtggcgaa cgggtgagta acacgtgggt aacctgccca tcagaagggg ataacacttg    120
gaaacaggtg ctaataccgt ataacactat tttccgcatg gaagaaagtt gaaaggcgct    180
tttgcgtcac tgatggatgg acccgcggtg cattagctag ttggtgaggt aacggctcac    240
caaggccacg atgcatagcc gacctgagag ggtgatcggc cacactggga ctgagacacg    300
gcccagactc ctacgggagg cagcagtagg gaatcttcgg caatggacga aagtctgacc    360
gagcaacgcc gcgtgagtga agaaggtttt cggatcgtaa aactctgttg ttagagaaga    420
acaaggatga gagtagaacg ttcatcccct tgacggtatct aaccagaaag ccacggctaa    480
ctacgtgcca gcagccgcgg taatacgtag gtggcaagcg ttgtccggat ttattgggcg    540
taaagcgagc gcaggcggtt tcttaagtct gatgtgaaag ccccggctc aaccggggag    600 ggtcattgga aactgggaga cttgagtgca gaagaggaga gtggaattcc atgtgtagcg    660
gtgaaatgcg tagatatatg gaggaacacc agtggcgaag gcggctctct ggtctgtaac    720
tgacgctgag gctcgaaagc gtggggagcg aacaggatta gataccctgg tagtccacgc    780
cgtaaacgat gagtgctaag tgttggaggg tttccgccct cagtgctgc agcaaacgca    840 ttaagcactc cgcctgggga gtacgaccgc aaggttgaaa ctcaaaggaa ttgacggggg    900
cccgcacaag cggtggagca tgtggtttaa ttcgaagcaa cgcgaagaac cttaccaggt    960
cttgacatcc tttgaccact ctagagatag agcttcccct tcggggggaa agtgacaggt   1020
ggtgcatggt tgtcgtcagc tcgtgtcgtg agatgttggg ttaagtcccg caacgagcgc   1080
aacccttatt gttagttgcc atcatttagt tgggcactct agcgagactg ccggtgacaa   1140
accggaggaa ggtggggatg acgtcaaatc atcatgcccc ttatgacctg gctacacac   1200 gtgctacaat gggaagtaca acgagttgcg aagtcgcgag gctaagctaa tctcttaaag   1260
cttctctcag ttcggattgt aggctgcaac tcgcctacat gaagccggaa tcgctagtaa   1320
tcgcggatca gcacgccgcg gtgaatacgt tcccgggcct tgtacacacc gcccgtcaca   1380
ccacgagagt ttgtaacacc cgaagtcggt gaggtaacct ttttggagcc agccgcctaa   1440
ggtg                                                                1444
```

```
<210> SEQ ID NO 3
<211> LENGTH: 1506
<212> TYPE: DNA
<213> ORGANISM: Enterococcus gallinarum
<220> FEATURE:
<223> OTHER INFORMATION: Enterococcus gallinarum strain MRx0554

<400> SEQUENCE: 3
```

| | | | | | |
|---|---|---|---|---|---|
| taatacatgc | aagtcgaacg | cttttctttt | caccggagct | tgctccaccg | aaagaaaaag | 60 |
| agtggcgaac | gggtgagtaa | cacgtgggta | acctgcccat | cagaagggga | taacacttgg | 120 |
| aaacaggtgc | taataccgta | taacactatt | ttccgcatgg | aagaaagttg | aaaggcgctt | 180 |
| ttgcgtcact | gatggatgga | cccgcggtgc | attagctagt | tggtgaggta | acggctcacc | 240 |
| aaggccacga | tgcatagccg | acctgagagg | gtgatcggcc | acactgggac | tgagacacgg | 300 |
| cccagactcc | tacgggaggc | agcagtaggg | aatcttcggc | aatggacgaa | agtctgaccg | 360 |
| agcaacgccg | cgtgagtgaa | gaaggttttc | ggatcgtaaa | actctgttgt | tagagaagaa | 420 |
| caaggatgag | agtagaacgt | tcatcccttg | acggtatcta | accagaaagc | cacggctaac | 480 |
| tacgtgccag | cagccgcggt | aatacgtagg | tggcaagcgt | tgtccggatt | tattgggcgt | 540 |
| aaagcgagcg | caggcggttt | cttaagtctg | atgtgaaagc | cccggctca | accggggagg | 600 |
| gtcattggaa | actgggagac | ttgagtgcag | aagaggagag | tggaattcca | tgtgtagcgg | 660 |
| tgaaatgcgt | agatatatgg | aggaacacca | gtggcgaagg | cggctctctg | gtctgtaact | 720 |
| gacgctgagg | ctcgaaagcg | tggggagcga | acaggattag | ataccctggt | agtccacgcc | 780 |
| gtaaacgatg | agtgctaagt | gttggagggt | ttccgccctt | cagtgctgca | gcaaacgcat | 840 |
| taagcactcc | gcctggggag | tacgaccgca | aggttgaaac | tcaaaggaat | tgacggggc | 900 |
| ccgcacaagc | ggtggagcat | gtggtttaat | tcgaagcaac | gcgaagaacc | ttaccaggtc | 960 |
| ttgacatcct | ttgaccactc | tagagataga | gcttcccctt | cggggcaaa | gtgacaggtg | 1020 |
| gtgcatggtt | gtcgtcagct | cgtgtcgtga | gatgttgggt | taagtcccgc | aacgagcgca | 1080 |
| acccttattg | ttagttgcca | tcatttagtt | gggcactcta | gcgagactgc | cggtgacaaa | 1140 |
| ccggaggaag | gtggggatga | cgtcaaatca | tcatgcccct | tatgacctgg | gctacacacg | 1200 |
| tgctacaatg | gaagtacaa | cgagttgcga | agtcgcgagg | ctaagctaat | ctcttaaagc | 1260 |
| ttctctcagt | tcggattgta | ggctgcaact | cgcctacatg | aagccggaat | cgctagtaat | 1320 |
| cgcggatcag | cacgccgcgg | tgaatacgtt | cccgggcctt | gtacacaccg | cccgtcacac | 1380 |
| cacgagagtt | tgtaacaccc | gaagtcggtg | aggtaacctt | tttggagcca | gccgcctaag | 1440 |
| gtgggataga | tgattggggt | gaagtcgtaa | caaggtagcc | gtatcggaag | gtgcggctgg | 1500 |
| atcacc | | | | | | 1506 |

```
<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      biotype identifying repetitive sequence

<400> SEQUENCE: 4
```

| | |
|---|---|
| gtggtggtgg tggtg | 15 |

COMPOSITIONS COMPRISING BACTERIAL STRAINS

CROSS-REFERENCE

This application is a continuation of International Application No. PCT/EP2019/056894, filed Mar. 19, 2019, which claims the benefit of Great Britain Application No. 1804384.4, filed Mar. 19, 2018, Great Britain Application No. 1809953.1, filed Jun. 18, 2018; Great Britain Application No. 1811900.8, filed Jul. 20, 2018; Great Britain Application No. 1812378.6, filed Jul. 30, 2018; Great Britain Application No. 1813423.9, filed Aug. 17, 2018; Great Britain Application No. 1813444.5, filed Aug. 17, 2018; Great Britain Application No. 1816834.4, filed Oct. 16, 2018; Great Britain Application No. 1817641.2, filed Oct. 29, 2018; European Application No. 18178350.7, filed Jun. 18, 2018; Great Britain Application No. 1901199.8, filed Jan. 29, 2019; Great Britain Application No. 1901218.6, filed Jan. 29, 2019; Great Britain Application No. 1901992.6, filed Feb. 13, 2019; Great Britain Application No. 1901993.4, filed Feb. 13, 2019, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 6, 2020, is named 56708-740_301_SL and is 7,414 bytes in size.

TECHNICAL FIELD

This invention is in the field of compositions comprising bacterial strains isolated from the mammalian digestive tract and the use of such compositions in the treatment of disease, in particular in stimulating the immune system in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Finnicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germfree animals which have an impaired immune system that is functionally reconstituted following the introduction of commensal bacteria [3-4].

Dramatic changes in microbiota composition have been documented in gastrointestinal disorders such as inflammatory bowel disease (IBD). For example, the levels of Clostridium cluster XIVa bacteria are reduced in IBD patients whilst numbers of E. coli are increased, suggesting a shift in the balance of symbionts and pathobionts within the gut [5-6]. Interestingly, this microbial dysbiosis is also associated with imbalances in T effector cell populations.

In recognition of the potential positive effect that certain bacterial strains may have on the animal gut, various strains have been proposed for use in the treatment of various diseases (see, for example, [7-8]). Also, certain strains, including mostly Lactobacillus and Bifidobacterium strains, have been proposed for use in treating various inflammatory and autoimmune diseases that are not directly linked to the intestines (see [9] and [10] for reviews). Certain Streptococcus and Veillonella strains, and to a lesser extent, Enterococcus and Lactobaccillus strains have been suggested to have immunomodulatory effects, with varying effects on different cytokines in vitro, suggesting that data obtained in vitro with individual strains are unlikely to adequately represent immune responses to mixtures of gut microbiota communities in vivo [88]. However, the relationship between different diseases and different bacterial strains, and the precise effects of particular bacterial strains on the gut and at a systemic level and on any particular types of diseases, are poorly characterised.

There is a requirement in the art for new methods of treating diseases. There is also a requirement for the potential effects of gut bacteria to be characterised so that new therapies using gut bacteria can be developed.

SUMMARY OF THE INVENTION

The inventors have developed new compositions comprising a bacterial strain of the species Enterococcus gallinarum that can be used in stimulating the immune system and treating and preventing disease. The inventors have identified that strains of the species Enterococcus gallinarum can potently activate the immune system and can treat cancer, which indicates that they may able to also treat other diseases where activation of the immune system may be useful.

The invention therefore provides a composition comprising a bacterial strain of the species Enterococcus gallinarum, for use in stimulating the immune system in subject.

In further aspects, the invention provides a composition comprising a bacterial strain of the species Enterococcus gallinarum, for use in treating, preventing or delaying immunosenescence.

In further aspects, the invention provides a composition comprising a bacterial strain of the species Enterococcus gallinarum, for use as a vaccine adjuvant.

In further aspects, the invention provides a composition comprising a bacterial strain of the species Enterococcus gallinarum, for use in enhancing a cell therapy, such as CAR-T.

Preferably, the bacteria used in the invention is the strain deposited under accession number 42488 at NCIMB.

In further preferred embodiments, the bacteria used in the invention is the strain deposited under accession number 42761 at NCIMB.

BRIEF DESCRIPTION OF DRAWINGS

FIG. 1A: Mouse model of breast cancer—changes in tumour volume post tumour induction and a table indicating the statistical significance between each two treatments at each time point.

FIG. 1B: Upper panel: Area of necrosis in EMT6 tumours (Untreated n=6, Vehicle n=6, MRx0518 n=8). Lower panel: Percentage of dividing cells in EMT6 tumours. P=0.019 (Untreated n=4, total number cells counted=37201, Vehicle n=6, total number of cells counted=64297, MRx0518 n=6, total number cells counted=33539).

FIG. 2: Mouse model of lung cancer—changes in tumour volume post tumour induction and a table indicating the statistical significance between each two treatments at each time point.

FIG. 3A: Mouse model of liver cancer—liver weight.

FIG. 3B: Mouse model of kidney cancer—changes in tumour volume post tumour induction and a table indicating the statistical significance between each two treatments at each time point.

FIG. 5A: Cytokine levels in THP-1 cells (No bacteria).

FIG. 5B: Cytokine levels in THP-1 cells after addition of bacterial sediment.

FIG. 5C: Cytokine levels in THP-1 cells after the addition of MRx0518MRx0518 alone or in combination with LPS.

FIG. 6: Immunostimulatory response—TNFα

FIG. 7: Immunostimulatory response—TNFα

FIG. 8: Immunostimulatory response—IL-12p70

FIG. 15: Mechanism of action—activation of TLR5

FIG. 17: Mouse model of breast cancer—tumour volume.

FIG. 19: Mechanism of action—TLR9 activation by MRx0518 (MRx0518$_{LV}$), heat-killed MRx0518 (MRx0518$_{HK}$) and MRx0518 culture supernatant (MRx0518$_{SN}$) in HEK-Blue™ hTLR9 reporter cell lines. ODN2006 was used as a positive control and YCFA medium was included as a negative control for MRx0518$_{SN}$. The bar graph represents an average of at least three biological replicates. Statistical analysis was performed using Graph-Pad Prism (ordinary one-way ANOVA analysis followed by Tukey's Multiple comparison test). Statistically significant differences with the relevant control are shown on the graphs as ****($p<0.0001$).

FIGS. 20A-20B: Induction of T-cell differentiation in a population of (FIG. 20A) T-helper cells and (FIG. 20B) Cytotoxic T Lymphocytes (CTL), using heat-killed MRx0518 (HK 518), Supernatant from MRx0518 culture or RPMI medium, without addition of cytokines (no cyto). *=$p\leq0.05$; =$p\leq0.01$; *=$p\leq0.001$; ****=$p\leq0.0001$.

(FIG. 21B) Splenocytes; or (FIG. 21C) THP-1 cells; which were treated with YCFA+medium ("Vehicle") or cell-free bacterial supernatant of MRx0518 ("MRx0518"). FIG. 21D shows fold change in cytokine expression following treatment of CaCo-2 cells with live bacteria ("MRx0518") relative to untreated cells.

(FIG. 22B) HEK-Blue™-hTLR4 cells; (FIG. 22C) HEK-Blue™-hTLR9 cells or (FIG. 22D) HEK-Blue™-hTLR5 cells. Cells were either untreated, treated with YCFA medium ("YCFA"), treated with MRx0518 ("MRx0518") or treated with positive controls.

FIG. 23: Heat map representing NanoString analysis of EMT6 tumour microenvironment following treatment with YCFA vehicle ("Vehicle") or MRx0518 ("MRx0518").

DISCLOSURE OF THE INVENTION

Bacterial Strains

Figure 1C:
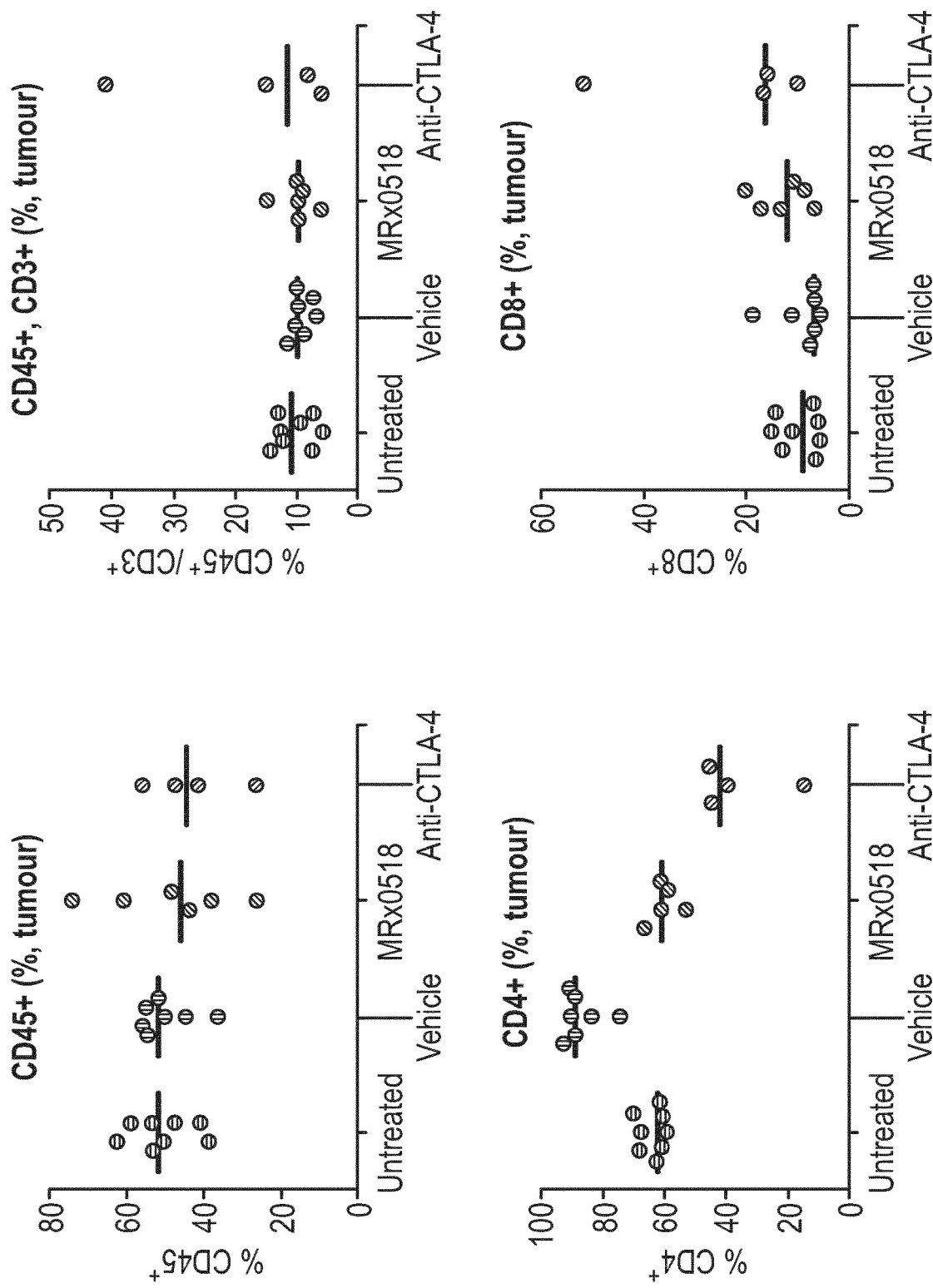
FIG. 1C: Mouse model of breast cancer—infiltrating immune cells. Scatter plots represent cell counts of different immune markers from individual animals from each treatment group.

The compositions of the invention comprise a bacterial strain of the species *Enterococcus gallinarum*. The examples demonstrate that bacteria of this genus are useful for stimulating the immune system and for treating disease.

*Enterococcus gallinarum* forms coccoid cells, mostly in pairs or short chains. It is motile and colonies on blood agar or nutrient agar are circular and smooth. *Enterococcus gallinarum* reacts with Lancefield group D antisera. The type strain of *Enterococcus gallinarum* is F87/276=PB21=ATCC 49573=CCUG 18658=CIP 103013=JCM 8728=LMG 13129=NBRC 100675=NCIMB 702313 (formerly NCDO 2313)=NCTC 12359 [11]. The GenBank accession number for a 16S rRNA gene sequence of *Entero-*

*coccus gallinarum* is AF039900 (disclosed herein as SEQ ID NO:1). An exemplary *Enterococcus gallinarum* strain is described in [11].

All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

The *Enterococcus gallinarum* bacterium deposited under accession number NCIMB 42488 was tested in the Examples and is also referred to herein as strain MRx0518. References to MRx0518 and MRx0518 are used interchangeably. A 16S rRNA sequence for the MRx0518 strain that was tested is provided in SEQ ID NO:2. Strain MRx0518 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 16 Nov. 2015 as "*Enterococcus sp*" and was assigned accession number NCIMB 42488.

The genome of strain MRx0518 comprises a chromosome and plasmid. A chromosome sequence for strain MRx0518 is provided in SEQ ID NO:3 OF WO2017/085520. A plasmid sequence for strain MRx0518 is provided in SEQ ID NO:4 OF WO2017/085520. These sequences were generated using the PacBio RS II platform.

The *Enterococcus gallinarum* bacterium deposited under accession number NCIMB 42761 was also tested in the Examples and is also referred to herein as strain MRx0554. References to MRx0554 and MRx0554 are used interchangeably. Strain MRx0554 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 22 May 2017 as "*Enterococcus gallinarum* MRx0554" and was assigned accession number NCIMB 42761. The genome sequence of this bacterium is disclosed herein as SEQ ID NO:2 OF WO2018/215782. The genome sequence was assembled from multiple contigs. Ns in the sequence represent gaps between the contigs. "N" may represent an A, G, C or T nucleotide. A 16S rRNA gene sequence for the MRx0554 strain is provided in SEQ ID NO:3. SEQ ID NO:3 represents the full length sequence present in the assembly, rather than a consensus of the five 16S genes present in MRx0554.

Bacterial strains closely related to the strains tested in the examples are also expected to be effective for simulating the immune system. In certain embodiments, the bacterial strain for use in the invention has a 16s rRNA gene sequence that is at least 95%, 96%, 97%, 98%, 99%, 99.5% or 99.9% identical to SEQ ID NO:1 or 2. Preferably, the sequence identity is to SEQ ID NO:2. Preferably, the bacterial strain for use in the invention has the 16s rRNA gene sequence represented by SEQ ID NO:2. In certain embodiments, the bacterial strain for use in the invention has a 16s rRNA gene sequence that is at least 95%, 96%, 97%, 98%, 99%, 99.5% or 99.9% identical to SEQ ID NO:3.

Bacterial strains that are biotypes of the bacterium deposited under accession number 42488 are also expected to be effective for stimulating the immune system. A biotype is a closely related strain that has the same or very similar physiological and biochemical characteristics.

Strains that are biotypes of the bacterium deposited under accession number NCIMB 42488 and that are suitable for use in the invention may be identified by sequencing other nucleotide sequences for the bacterium deposited under accession number NCIMB 42488. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, $(GTG)_5$ (SEQ ID NO: 4), or REP or [12]. Biotype strains may have sequences with at least 95%, 96%, 97%, 98%, 99%, 99.5% or 99.9% sequence identity to the corresponding sequence of the bacterium deposited under accession number NCIMB 42488. In some embodiments, a biotype strain has a sequence with at least 95%, 96%, 97%, 98%, 99%, 99.5% or 99.9% sequence identity to the corresponding sequence of strain MRx0518 deposited as NCIMB 42488 and comprises a 16S rRNA gene sequence that is at least 99% identical (e.g. at least 99.5% or at least 99.9% identical) to SEQ ID NO:2. In some embodiments, a biotype strain has a sequence with at least 95%, 96%, 97%, 98%, 99%, 99.5% or 99.9% sequence identity to the corresponding sequence of strain MRx0518 deposited as NCIMB 42488 and has the 16S rRNA sequence of SEQ ID NO:2.

In certain embodiments, the bacterial strain for use in the invention has a chromosome with sequence identity to SEQ ID NO:3 OF WO2017/085520. In preferred embodiments, the bacterial strain for use in the invention has a chromosome with at least 90% sequence identity (e.g. at least 92%, 94%, 95%, 96%, 97%, 98%, 99% or 100% sequence identity) to SEQ ID NO:3 OF WO2017/085520 across at least 60% (e.g. at least 65%, 70%, 75%, 80%, 85%, 95%, 96%, 97%, 98%, 99% or 100%) of SEQ ID NO:3 OF WO2017/085520. For example, the bacterial strain for use in the invention may have a chromosome with at least 90% sequence identity to SEQ ID NO:3 OF WO2017/085520 across 70% of SEQ ID NO:3 OF WO2017/085520, or at least 90% sequence identity to SEQ ID NO:3 OF WO2017/085520 across 80% of SEQ ID NO:3 OF WO2017/085520, or at least 90% sequence identity to SEQ ID NO:3 OF WO2017/085520 across 90% of SEQ ID NO:3 OF WO2017/085520, or at least 90% sequence identity to SEQ ID NO:3 OF WO2017/085520 across 100% of SEQ ID NO:3 OF WO2017/085520, or at least 95% sequence identity to SEQ ID NO:3 OF WO2017/085520 across 70% of SEQ ID NO:3 OF WO2017/085520, or at least 95% sequence identity to SEQ ID NO:3 OF WO2017/085520 across 80% of SEQ ID NO:3 OF WO2017/085520, or at least 95% sequence identity to SEQ ID NO:3 OF WO2017/085520 across 90% of SEQ ID NO:3 OF WO2017/085520, or at least 95% sequence identity to SEQ ID NO:3 OF WO2017/085520 across 100% of SEQ ID NO:3 OF WO2017/085520, or at least 98% sequence identity to SEQ ID NO:3 OF WO2017/085520 across 70% of SEQ ID NO:3 OF WO2017/085520, or at least 98% sequence identity to SEQ ID NO:3 OF WO2017/085520 across 80% of SEQ ID NO:3 OF WO2017/085520, or at least 98% sequence identity to SEQ ID NO:3 OF WO2017/085520 across 90% of SEQ ID NO:3 OF WO2017/085520, or at least 98% identity to SEQ ID NO:3 OF WO2017/085520 across 95% of SEQ ID NO:3 OF WO2017/085520, or at least 98% sequence identity to SEQ ID NO:3 OF WO2017/085520 across 100% of SEQ ID NO:3 OF WO2017/085520, or at least 99.5% sequence identity to SEQ ID NO:3 OF WO2017/085520 across 90% of SEQ ID NO:3 OF WO2017/085520, or at least 99.5% identity to SEQ ID NO:3 OF WO2017/085520 across 95% of SEQ ID NO:3 OF WO2017/085520, or at least 99.5% identity to SEQ ID NO:3 OF WO2017/085520 across 98% of SEQ ID NO:3 OF WO2017/085520, or at least 99.5% sequence identity to SEQ ID NO:3 OF WO2017/085520 across 100% of SEQ ID NO:3 OF WO2017/085520.

In certain embodiments, the bacterial strain for use in the invention has a plasmid with sequence identity to SEQ ID NO:4 OF WO2017/085520. In preferred embodiments, the bacterial strain for use in the invention has a plasmid with at least 90% sequence identity (e.g. at least 92%, 94%, 95%, 96%, 97%, 98%, 99% or 100% sequence identity) to SEQ ID NO:4 OF WO2017/085520 across at least 60% (e.g. at least 65%, 70%, 75%, 80%, 85%, 95%, 96%, 97%, 98%, 99% or 100%) of SEQ ID NO:4 OF WO2017/085520. For example, the bacterial strain for use in the invention may have a plasmid with at least 90% sequence identity to SEQ ID NO:4 OF WO2017/085520 across 70% of SEQ ID NO:4 OF WO2017/085520, or at least 90% sequence identity to SEQ ID NO:4 OF WO2017/085520 across 80% of SEQ ID NO:4 OF WO2017/085520, or at least 90% sequence identity to SEQ ID NO:4 OF WO2017/085520 across 90% of SEQ ID NO:4 OF WO2017/085520, or at least 90% sequence identity to SEQ ID NO:4 OF WO2017/085520 across 100% of SEQ ID NO:4 OF WO2017/085520, or at least 95% sequence identity to SEQ ID NO:4 OF WO2017/085520 across 70% of SEQ ID NO:4 OF WO2017/085520, or at least 95% sequence identity to SEQ ID NO:4 OF WO2017/085520 across 80% of SEQ ID NO:4 OF WO2017/085520, or at least 95% sequence identity to SEQ ID NO:4 OF WO2017/085520 across 90% of SEQ ID NO:4 OF WO2017/085520, or at least 95% sequence identity to SEQ ID NO:4 OF WO2017/085520 across 100% of SEQ ID NO:4 OF WO2017/085520, or at least 98% sequence identity to SEQ ID NO:4 OF WO2017/085520 across 70% of SEQ ID NO:4 OF WO2017/085520, or at least 98% sequence identity to SEQ ID NO:4 OF WO2017/085520 across 80% of SEQ ID NO:4 OF WO2017/085520, or at least 98% sequence identity to SEQ ID NO:4 OF WO2017/085520 across 90% of SEQ ID NO:4 OF WO2017/085520, or at least 98% sequence identity to SEQ ID NO:4 OF WO2017/085520 across 100% of SEQ ID NO:4 OF WO2017/085520.

In certain embodiments, the bacterial strain for use in the invention has a chromosome with sequence identity to SEQ ID NO:3 OF WO2017/085520 and a plasmid with sequence identity to SEQ ID NO:4 OF WO2017/085520.

In certain embodiments, the bacterial strain for use in the invention has a chromosome with sequence identity to SEQ ID NO:3 OF WO2017/085520, for example as described above, and a 16S rRNA sequence with sequence identity to any of SEQ ID NO:1 or 2, for example as described above, preferably with a 16s rRNA sequence that is at least 99% identical to SEQ ID NO: 2, more preferably which comprises the 16S rRNA sequence of SEQ ID NO:2, and optionally comprises a plasmid with sequence identity to SEQ ID NO:4 OF WO2017/085520, as described above.

In certain embodiments, the bacterial strain for use in invention has a chromosome with sequence identity to SEQ ID NO:3 OF WO2017/085520, for example as described above, and optionally comprises a plasmid with sequence identity to SEQ ID NO:4 OF WO2017/085520, as described above, and is effective for stimulating the immune system.

In certain embodiments, the bacterial strain for use in the invention has a chromosome with sequence identity to SEQ ID NO:3 OF WO2017/085520, for example as described above, and a 16S rRNA sequence with sequence identity to any of SEQ ID NOs: 1 or 2, for example as described above, and optionally comprises a plasmid with sequence identity to SEQ ID NO:4 OF WO2017/085520, as described above, and is effective for stimulating the immune system.

In certain embodiments, the bacterial strain for use in the invention has a 16s rRNA sequence that is at least 99%, 99.5% or 99.9% identical to the 16s rRNA sequence represented by SEQ ID NO: 2 (for example, which comprises the 16S rRNA sequence of SEQ ID NO:2) and a chromosome with at least 95% sequence identity to SEQ ID NO:3 OF WO2017/085520 across at least 90% of SEQ ID NO:3 OF WO2017/085520, and optionally comprises a plasmid with sequence identity to SEQ ID NO:4 OF WO2017/085520, as described above, and which is effective for stimulating the immune system.

In certain embodiments, the bacterial strain for use in the invention has a 16s rRNA sequence that is at least 99%, 99.5% or 99.9% identical to the 16s rRNA gene sequence represented by SEQ ID NO: 2 (for example, which comprises the 16S rRNA sequence of SEQ ID NO:2) and a chromosome with at least 98% sequence identity (e.g. at least 99% or at least 99.5% sequence identity) to SEQ ID NO:3 OF WO2017/085520 across at least 98% (e.g. across at least 99% or at least 99.5%) of SEQ ID NO:3 OF WO2017/085520, and optionally comprises a plasmid with sequence identity to SEQ ID NO:4 OF WO2017/085520, as described above, and which is effective for stimulating the immune system.

In certain embodiments, the bacterial strain for use in the invention is a *Enterococcus gallinarum* and has a 16s rRNA sequence that is at least 99%, 99.5% or 99.9% identical to the 16s rRNA sequence represented by SEQ ID NO: 2 (for example, which comprises the 16S rRNA sequence of SEQ ID NO:2) and a chromosome with at least 98% sequence identity (e.g. at least 99% or at least 99.5% sequence identity) to SEQ ID NO:3 OF WO2017/085520 across at least 98% (e.g. across at least 99% or at least 99.5%) of SEQ ID NO:3 OF WO2017/085520, and optionally comprises a plasmid with sequence identity to SEQ ID NO:4 OF WO2017/085520, as described above, and which is effective for stimulating the immune system.

Alternatively, strains that are biotypes of the bacterium deposited under accession number NCIMB 42488 and that are suitable for use in the invention may be identified by using the accession number NCIMB 42488 deposit and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other *Enterococcus gallinarum* strains.

In certain embodiments, strains that are biotypes of the bacterium deposited under accession number NCIMB 42488 and that are suitable for use in the invention are strains that provide the same pattern as the bacterium deposited under accession number NCIMB 42488 when analysed by amplified ribosomal DNA restriction analysis (ARDRA), for example when using Sau3AI restriction enzyme (for exemplary methods and guidance see, for example, [13]). Alternatively, biotype strains are identified as strains that have the same carbohydrate fermentation patterns as the bacterium deposited under accession number NCIMB 42488. In some embodiments, the carbohydrate fermentation pattern is determined using the API 50 CHL panel (bioMérieux). In some embodiments, the bacterial strain used in the invention is:
- (i) positive for fermentation of at least one of (e.g. at least 2, 3, 4, 5, 6, 7, 8, 9, 10, 11, 12, 13, 14, 15, 16, 17 or all of): L-arabinose, D-ribose, D-xylose, D-galactose, D-glucose, D-fructose, D-mannose, N-acetylglucosamine, amygdalin, arbutin, salicin, D-cellobiose, D-maltose, sucrose, D-trehalose, gentiobiose, D-tagatose and potassium gluconate; and/or
- (ii) intermediate for fermentation of at least one of (e.g. at least 2, 3, 4 or all of): D-mannitol, Methyl-αD-glycopyranoside, D-lactose, starch, and L-fucose; preferably as determined by API 50 CHL analysis (preferably using the API 50 CHL panel from bioMérieux).

Other *Enterococcus gallinarum* strains that are useful in the compositions and methods of the invention, such as biotypes of the bacterium deposited under accession number NCIMB 42488, may be identified using any appropriate method or strategy, including the assays described in the examples. For instance, strains for use in the invention may be identified by assessing their effects on cytokine levels, as performed in the examples. In particular, bacterial strains that have similar growth patterns, metabolic type and/or surface antigens to the bacterium deposited under accession number NCIMB 42488 may be useful in the invention. A useful strain will have comparable immune modulatory activity to the NCIMB 42488 strain. In particular, a biotype strain will elicit comparable effects on the cancer disease models to the effects shown in the Examples, which may be identified by using the culturing and administration protocols described in the Examples. According to some embodiments, a biotype strain that may be used in the invention is a strain which is able to elicit comparable effects on the cancer disease models shown in the Examples when administered in the method of the invention.

In some embodiments, the bacterial strain used in the invention is:
- (i) Positive for at least one of (e.g. at least 2, 3, 4, 5, 6, 7 or all of): mannose fermentation, glutamic acid decarboxylase, arginine arylamidase, phenylalanine arylamidase, pyroglutamic acid arylamidase, tyrosine arylamidase, histidine arylamidase and serine arylamidase; and/or
- (ii) Intermediate for at least one of (e.g. at least 2 or all of): β-galactosidase-6-phosphate, glucosidase and N-acetyl-β-glucosaminidase; and/or
- (iii) Negative for at least one of (e.g. at least 2, 3, 4, 5, 6 or all of): Raffinose fermentation, Proline arylamidase, Leucyl glycine arylamidase, Leucine arylamidase, Alanine arylamidase, Glycine arylamidase and Glutamyl glutamic acid arylamidase, preferably as determined by an assay of carbohydrate, amino acid and nitrate metabolism, and optionally an assay of alkaline phosphatase activity, more preferably as determined by Rapid ID 32A analysis (preferably using the Rapid ID 32A system from bioMérieux).

In some embodiments, the bacterial strain used in the invention is:
- (i) Negative for at least one of (e.g. at least 2, 3, or all 4 of) glycine arylamidase, raffinose fermentation, proline arylamidase, and leucine arylamidase, for example, as determined by an assay of carbohydrate, amino acid and nitrate metabolism, preferably as determined by Rapid ID 32A analysis (preferably using the Rapid ID 32A system from bioMérieux); and/or
- (ii) Intermediate positive for fermentation of L-fucose, preferably as determined by API 50 CHL analysis (preferably using the API 50 CHL panel from bioMérieux).

In some embodiments, the bacterial strain used in the invention is an extracellular ATP producer, for example one which produces 6-6.7 ng/µl (for example, 6.1-6.6 ng/µl or 6.2-6.5 ng/µl or 6.33±0.10 ng/µl) of ATP as measured using the ATP Assay Kit (Sigma-Aldrich, MAK190). Bacterial extracellular ATP can have pleiotropic effects including activation of T cell-receptor mediated signalling (Schenk et al., 2011), promotion of intestinal Th17 cell differentiation (Atarashi et al., 2008) and induction of secretion of the pro-inflammatory mediator IL-1(3 by activating the NLRP3 inflammasome (Karmarkar et al., 2016). Accordingly, a bacterial strain which is an extracellular ATP producer is useful for stimulating the immune system in the context of the method of the invention.

In some embodiments, the bacterial strain for use in the invention comprises one or more of the following three genes: Mobile element protein; Xylose ABC transporter, permease component; and FIG00632333: hypothetical protein. For example, in certain embodiments, the bacterial strain for use in the invention comprises genes encoding Mobile element protein and Xylose ABC transporter, permease component; Mobile element protein and FIG00632333: hypothetical protein; Xylose ABC transporter, permease component and FIG00632333: hypothetical protein; or Mobile element protein, Xylose ABC transporter, permease component, and FIG00632333: hypothetical protein.

A particularly preferred strain of the invention is the *Enterococcus gallinarum* strain deposited under accession number NCIMB 42488. This is the exemplary MRx0518 strain tested in the examples and shown to be effective for treating disease. The invention provides, according to some embodiments, a bacterial composition as part of the invention, comprising a cell of the *Enterococcus gallinarum* strain deposited under accession number NCIMB 42488, or a derivative thereof. A derivative of the strain deposited under accession number NCIMB 42488 may be a daughter strain (progeny) or a strain cultured (subcloned) from the original.

A derivative of a strain of the composition comprised in the invention may be modified, for example at the genetic level, without ablating the biological activity. In particular, a derivative strain of the invention is therapeutically active. A derivative strain will have comparable immune modulatory activity to the original NCIMB 42488 strain. In particular, a derivative strain will elicit comparable effects on the cancer disease models when which may be identified by using the culturing and administration protocols described in the Examples. A derivative of the NCIMB 42488 strain will generally be a biotype of the NCIMB 42488 strain.

References to cells of the *Enterococcus gallinarum* strain deposited under accession number NCIMB 42488 encompass any cells that have the same safety and therapeutic efficacy characteristics as the strains deposited under accession number NCIMB 42488, and such cells are encompassed by the the invention. Thus, in some embodiments, reference to cells of the *Enterococcus gallinarum* strain deposited under accession number NCIMB 42488 refers only to the MRx0518 strain deposited under NCIMB 42488 and does not refer to a bacterial strain that was not deposited under NCIMB 42488. In some embodiments, reference to cells of the *Enterococcus gallinarum* strain deposited under accession number NCIMB 42488 refers to cells that have the same safety and therapeutic efficacy characteristics as the strains deposited under accession number NCIMB 42488, but which are not the strain deposited under NCIMB 42488.

Bacterial strains that are biotypes of the bacterium deposited under accession number 42761 are also expected to be effective for stimulating the immune system. A biotype is a closely related strain that has the same or very similar physiological and biochemical characteristics.

Strains that are biotypes of the bacterium deposited under accession number NCIMB 42761 and that are suitable for use in the invention may be identified by sequencing other nucleotide sequences for the bacterium deposited under accession number NCIMB 42761. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, $(GTG)_5$ (SEQ ID NO: 4), or REP or [14]. Biotype strains may have sequences with at least 95%, 96%, 97%, 98%, 99%, 99.5% or 99.9% sequence identity to the corresponding sequence of the bacterium deposited under accession number NCIMB 42761. In some embodiments, a biotype strain has a sequence with at least 95%, 96%, 97%, 98%, 99%, 99.5% or 99.9% sequence identity to the corresponding sequence of strain MRx0554 deposited as NCIMB 42761. In some embodiments, a biotype strain has a sequence with at least 95%, 96%, 97%, 98%, 99%, 99.5% or 99.9% sequence identity to the corresponding sequence of strain MRx0554 deposited as NCIMB 42761 and has a 16S rRNA gene sequence that is at least 99% identical (e.g. at least 99.5% or at least 99.9% identical) to SEQ ID NO:3. In some embodiments, a biotype strain has a sequence with at least 95%, 96%, 97%, 98%, 99%, 99.5% or 99.9% sequence identity to the corresponding sequence of strain MRx0554 deposited as NCIMB 42761 and has the 16S rRNA gene sequence of SEQ ID NO:3.

Alternatively, strains that are biotypes of the bacterium deposited under accession number NCIMB 42761 and that are suitable for use in the invention may be identified by using the accession number NCIMB 42761 deposit and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing.

In certain embodiments, strains that are biotypes of the bacterium deposited under accession number NCIMB 42761 and that are suitable for use in the invention are strains that provide the same pattern as the bacterium deposited under accession number NCIMB 42761 when analysed by amplified ribosomal DNA restriction analysis (ARDRA), for example when using Sau3AI restriction enzyme (for exemplary methods and guidance see, for example, [15]). Alternatively, biotype strains are identified as strains that have the same carbohydrate fermentation patterns as the bacterium deposited under accession number NCIMB 42761. In some embodiments, the carbohydrate fermentation pattern is determined using the API 50 CHL panel (bioMérieux). In some embodiments, the bacterial strain used in the invention is:

(iii) positive for fermentation of at least one of (e.g. at least 2, 3, 4, 5, 6, 7, 8, 9, 10, 11, 12, 13, 14, 15, 16, 17 or all of): L-arabinose, D-ribose, D-xylose, D-galactose, D-glucose, D-fructose, D-mannose, N-acetylglucosamine, amygdalin, arbutin, salicin, D-cellobiose, D-maltose, sucrose, D-trehalose, gentiobiose, D-tagatose and potassium gluconate; and/or (iv) intermediate for fermentation of at least one of (e.g. at least 2, 3, 4 or all of): D-mannitol, Methyl-αD-glycopyranoside, D-lactose, starch, and L-fucose;

preferably as determined by API 50 CHL analysis (preferably using the API 50 CHL panel from bio-Mérieux).

In some embodiments, the bacterial strain used in the invention is:

(i) positive for fermentation of at least one of (e.g. at least 2, 3, 4, 5, 6, 7, 8, 9, 10, 11, 12, 13, 14, 15, 16, 17, 18 or all of): L-arabinose, D-ribose, D-xylose, D-galactose, D-glucose, D-fructose, D-mannose, N-acetylglucosamine, amygdalin, arbutin, esculin, salicin, D-cellobiose, D-maltose, D-saccharose (sucrose), D-trehalose, gentiobiose, D-tagatose and potassium gluconate;

(ii) intermediate for fermentation of at least one of (e.g. at least 2, 3, 4, 5 or all of): D-mannitol, Methyl-αD-glycopyranoside, D-lactose, D-raffinose, amidon (starch), and D-turanose; and/or (iii) negative for fermentation of at least one of (e.g. at least 2, 3, 4, 5, 6, 7, 8, 9, 10, 11, 12, 13, 14, 15, 16, 17, 18, 19, 20, 21, 22, 23 or all of): glycerol, erythritol, D-arabinose, L-xylose, D-adonitol, methyl-βD-xylopyranoside, L-sorbose, L-rhamnose, dulcitol, inositol, D-sorbitol, Methyl-αD-mannopyranoside, D-melibiose, inulin, D-melezitose, glycogen, xylitol, D-lyxose, D-fucose, L-fucose, D-arabitol, L-arabitol, potassium 2-ketogluconate and potassium 5-ketogluconate;

preferably as determined by API 50 CHL analysis (preferably using the API 50 CHL panel from bio-Mérieux, and preferably using the conditions described in Example 10).

Other *Enterococcus gallinarum* strains that are useful in the compositions and methods of the invention, such as biotypes of the bacterium deposited under accession number NCIMB 42761, may be identified using any appropriate method or strategy, including the assays described in the examples. For instance, strain for use in the invention may be identified by culturing in anaerobic YCFA and/or administering the bacteria to the type II collagen-induced arthritis mouse model and then assessing cytokine levels. In particular, bacterial strains that have similar growth patterns, metabolic type and/or surface antigens to the bacterium deposited under accession number NCIMB 42761 may be useful in the invention. A useful strain will have comparable immune modulatory activity to the NCIMB 42761 strain. In particular, a biotype strain will elicit comparable effects on the cancer disease models to the effects shown in the Examples, which may be identified by using the culturing and administration protocols described in the Examples.

A derivative of a strain of the invention may be modified, for example at the genetic level, without ablating the biological activity. In particular, a derivative strain of the invention is therapeutically active. A derivative strain will have comparable immune modulatory activity to the original NCIMB 42761 strain. In particular, a derivative strain will elicit comparable effects on the cancer disease models to the effects shown in the Examples, which may be identified by using the culturing and administration protocols described in the Examples. A derivative of the NCIMB 42761 strain will generally be a biotype of the NCIMB 42761 strain.

References to cells of the *Enterococcus gallinarum* strain deposited under accession number NCIMB 42761 encompass any cells that have the same safety and therapeutic efficacy characteristics as the strain deposited under accession number NCIMB 42761, and such cells are encompassed by the invention. Thus, in some embodiments, reference to cells of the *Enterococcus gallinarum* strain deposited under accession number NCIMB 42761 refers only to the MRx0554 strain deposited under NCIMB 42761 and does not refer to a bacterial strain that was not deposited under NCIMB 42761.

In certain embodiments, the bacterial strain for use in the invention has a genome with sequence identity to SEQ ID NO:2 OF WO2018/215782. In some embodiments, the bacterial strain for use in the invention has a genome with at least 90% sequence identity (e.g. at least 92%, 94%, 95%, 96%, 97%, 98%, 99% or 100% sequence identity) to SEQ ID NO:2 OF WO2018/215782 across at least 60% (e.g. across at least 65%, 70%, 75%, 80%, 85%, 95%, 96%, 97%, 98%, 99% or 100%) of SEQ ID NO:2 OF WO2018/215782. For example, the bacterial strain for use in the invention may have a genome with at least 90% sequence identity to SEQ ID NO:2 OF WO2018/215782 across 70% of SEQ ID NO:2 OF WO2018/215782, or at least 90% sequence identity to SEQ ID NO:2 OF WO2018/215782 across 80% of SEQ ID NO:2 OF WO2018/215782, or at least 90% sequence identity to SEQ ID NO:2 OF WO2018/215782 across 90% of SEQ ID NO:2 OF WO2018/215782, or at least 90% sequence identity to SEQ ID NO:2 OF WO2018/215782 across 100% of SEQ ID NO:2 OF WO2018/215782, or at least 95% sequence identity to SEQ ID NO:2 OF WO2018/215782 across 70% of SEQ ID NO:2 OF WO2018/215782, or at least 95% sequence identity to SEQ ID NO:2 OF WO2018/215782 across 80% of SEQ ID NO:2 OF WO2018/215782, or at least 95% sequence identity to SEQ ID NO:2 OF WO2018/215782 across 90% of SEQ ID NO:2 OF WO2018/215782, or at least 95% sequence identity to SEQ ID NO:2 OF WO2018/215782 across 100% of SEQ ID NO:2 OF WO2018/215782, or at least 98% sequence identity to SEQ ID NO:2 OF WO2018/215782 across 70% of SEQ ID NO:2 OF WO2018/215782, or at least 98% sequence identity to SEQ ID NO:2 OF WO2018/215782 across 80% of SEQ ID NO:2 OF WO2018/215782, or at least 98% sequence identity to SEQ ID NO:2 OF WO2018/215782 across 90% of SEQ ID NO:2 OF WO2018/215782, or at least 98% identity across 95% of SEQ ID NO:2 OF WO2018/215782, or at least 98% sequence identity to SEQ ID NO:2 OF WO2018/215782 across 100% of SEQ ID NO:2 OF WO2018/215782, or at least 99.5% sequence identity to SEQ ID NO:2 OF WO2018/215782 across 90% of SEQ ID NO:2 OF WO2018/215782, or at least 99.5% identity across 95% of SEQ ID NO:2 OF WO2018/215782, or at least 99.5% identity across 98% of SEQ ID NO:2 OF WO2018/215782, or at least 99.5% sequence identity to SEQ ID NO:2 OF WO2018/215782 across 100% of SEQ ID NO:2 OF WO2018/215782.

In certain embodiments, the bacterial strain for use in the invention has a genome with sequence identity to SEQ ID NO:2 OF WO2018/215782, for example as described above, and a 16S rRNA gene sequence with sequence identity to SEQ ID NO:1 or 3, for example as described above, preferably with a 16S rRNA gene sequence that is at least 99% identical to SEQ ID NO:3, more preferably which comprises the 16S rRNA gene sequence of SEQ ID NO:3.

In certain embodiments, the bacterial strain for use in the invention has a genome with sequence identity to SEQ ID NO:2 OF WO2018/215782, for example as described above, and is effective for stimulating the immune system.

In certain embodiments, the bacterial strain for use in the invention has a genome with sequence identity to SEQ ID NO:2 OF WO2018/215782, for example as described above, and a 16S rRNA gene sequence with sequence identity to SEQ ID NO: 1 or 3, for example as described above, and is effective for stimulating the immune system.

In certain embodiments, the bacterial strain for use in the invention has a 16S rRNA gene sequence that is at least 99%, 99.5% or 99.9% identical to the 16S rRNA gene sequence represented by SEQ ID NO: 3 (for example, which comprises the 16S gene rRNA sequence of SEQ ID NO:3) and a genome with at least 95% sequence identity to SEQ ID NO:2 OF WO2018/215782 across at least 90% of SEQ ID NO:2 OF WO2018/215782, and which is effective for stimulating the immune system.

In certain embodiments, the bacterial strain for use in the invention is a *Enterococcus gallinarum* and has a 16S rRNA gene sequence that is at least 99%, 99.5% or 99.9% identical to the 16S rRNA gene sequence represented by SEQ ID NO:3 (for example, which comprises the 16S rRNA gene sequence of SEQ ID NO:3) and a genome with at least 98% sequence identity (e.g. at least 99% or at least 99.5% sequence identity) to SEQ ID NO:2 OF WO2018/215782 across at least 98% (e.g. across at least 99% or at least 99.5%) of SEQ ID NO:2 OF WO2018/215782, and which is effective for stimulating the immune system.

In preferred embodiments, the bacterial strains in the compositions of the invention are viable and capable of partially or totally colonising the intestine.

In alternative aspects of every embodiment of the invention, the bacterial strain in the composition of the invention is of the species *Enterococcus caselliflavus*. *Enterococcus caselliflavus* is highly similar to *Enterococcus gallinarum* and is also flagellated.

Therapeutic Uses

Stimulating the Immune System

The examples show that administration of the compositions of the invention can lead to immune stimulation. Since administration of the compositions of the invention were shown to have an immunostimulatory effect, compositions of the invention may be useful in the treatment of disease, in particular diseases characterised by reduced immune activation and diseases treatable by an increased immune response. In certain embodiments, the compositions of the invention are for use in stimulating the immune system. In certain embodiments, the compositions of the invention are for use in treating disease by stimulating the immune system. In certain embodiments, the compositions of the invention are for use in promoting an immune response.

Compositions of the invention may be useful in the treatment of diseases characterised by an increase in the percentage of Tregs in a cell population. In one embodiment, the compositions of the invention may be useful for treating or preventing diseases characterised by an increase in the percentage of Tregs in a cell population. In one embodiment, the compositions of the invention may be useful for treating or preventing diseases characterised by an increase in the percentage of CD4+CD25+CD127− cells in a cell population. In one embodiment, the compositions of the invention are for use in treating or preventing diseases by decreasing the percentage of Tregs in cell populations. In one embodiment, compositions of the invention are for use in reducing suppression of the immune response by Tregs. In one embodiment, compositions of the invention are for use in stimulating the immune response by the selective reduction of Tregs. In one embodiment, compositions of the invention are for use in immunostimulation, wherein the compositions of the invention reduce the number or percentage of Tregs.

Compositions of the invention may be useful in the treatment of diseases characterised by a decrease in the ratio of CD8/Treg and/or activated CD8/Treg cells. In one embodiment, the compositions of the invention are for use in treating or preventing diseases characterised by decrease in the ratio of CD8/Treg cells. In one embodiment, the compositions of the invention are for use in treating or preventing diseases characterised by decrease in the ratio of activated CD8/Treg cells. In one embodiment, compositions of the invention are for use in stimulating the immune response by increasing the ratio of CD8/Treg cells. In one embodiment, compositions of the invention are for use in stimulating the immune response by increasing the ratio of activated CD8/Treg cells.

Compositions of the invention may be useful in the treatment of diseases characterised by a decrease in the number or percentage of B cells. In one embodiment, the compositions of the invention are for use in treating or preventing diseases characterised by decrease in the number or percentage of B cells. In one embodiment, the compositions of the invention are for use in treating or preventing diseases characterised by decrease in the number or percentage of CD19$^+$CD3− cells. In one embodiment, the compositions of the invention are for use in treating or preventing diseases by increasing the number or percentage of B cells in cell populations, wherein the increase in number or percentage of B cells results in immune stimulation. In one embodiment, compositions of the invention are for use in stimulating the immune response by increasing the number or percentage of B cells.

Compositions of the invention may be useful in the treatment of diseases characterised by a decrease in the number or percentage of CD8 T-cytotoxic cells. In one embodiment, the compositions of the invention are for use in treating or preventing diseases characterised by decrease in the number or percentage of CD8 T-cytotoxic cells. In one embodiment, the compositions of the invention are for use in treating or preventing diseases by increasing the number or percentage of CD8 T-cytotoxic cells in cell populations, wherein the increase in number or percentage of CD8 T-cytotoxic cells results in immune stimulation. In one embodiment, compositions of the invention are for use in stimulating the immune response by increasing the number or percentage of CD8 T-cytotoxic cells.

Compositions of the invention may be useful in the treatment of diseases characterised by a decrease in the number or percentage of CD8$^+$ activated cells. In one embodiment, the compositions of the invention are for use in treating or preventing diseases characterised by decrease in the number or percentage of CD8$^+$ activated cells. In one embodiment, the compositions of the invention are for use in treating or preventing diseases by increasing the number or percentage of CD8$^+$ activated cells in cell populations, wherein the increase in number or percentage of CD8$^+$ activated cells results in immune stimulation. In one embodiment, compositions of the invention are for use in stimulating the immune response by increasing the number or percentage of CD8$^+$ activated cells.

The examples show that administration of the compositions of the invention can lead to an increase in expression of pro-inflammatory molecules, such as pro-inflammatory cytokines. Examples of pro-inflammatory molecules that showed an increase in expression levels upon administration of compositions of the invention include IL-8, IL-12p70, IL-23, TNF-α, IL-1β, and IL-6. Since administration of the compositions of the invention were shown to increase the expression of pro-inflammatory molecules, compositions of the invention may be useful in the treatment of diseases characterised by a decrease in expression of pro-inflammatory molecules, such as pro-inflammatory cytokines. In one embodiment, the compositions of the invention are for use in treating or preventing diseases characterised by a decrease in the expression and/or activity of pro-inflammatory molecules, in particular diseases characterised by a decrease in the expression and/or activity of pro-inflammatory cytokines. In a particular embodiment, the compositions of the invention are for use in treating or preventing diseases characterised by a decrease in the expression and/or activity of IL-8, IL-12p70, IL-23, TNF-α, IL-1β,- and/or IL-6. In one embodiment, the compositions of the invention are for use in treating or preventing diseases by increasing the expression and/or activity of IL-23, TNF-α, IL-1β, and/or IL-6. In one embodiment, compositions of the invention are for use in promoting the immune response by increasing the expression and/or activity of IL-8, IL-12p70, IL-23, TNF-α, IL-1β, and/or IL-6.

The examples also show that administration of the compositions of the invention can lead to an increase in expression of IL-1β. IL-1β is a pro-inflammatory cytokine [16]. The production and secretion of IL-1β is regulated by the inflammasome, a protein complex which is associated with activation of the inflammatory response [17]. Since administration of the compositions of the invention were shown to increase the expression of IL-1β, compositions of the invention may be useful in the treatment of diseases characterised by a decrease in expression of IL-1β. In a particular embodiment, the compositions of the invention are for use in treating or preventing diseases characterised by a decrease in the expression and/or activity of IL-1β. In one embodiment, the compositions of the invention are for use in treating or preventing diseases by increasing the expression and/or activity of IL-1β.

The examples also show that administration of the compositions of the invention can lead to an increase in expression of IL-23. IL-23 has been linked to inflammation [18, 19]. The proposed functions of IL-23 in the immune response include promoting the proliferation of CD4$^+$ memory T cells and promoting the secretion of IFN-γ by dendritic cells (DCs) [20]. Since administration of the compositions of the invention were shown to increase the expression of IL-23, compositions of the invention may be useful in the treatment of diseases characterised by a decrease in expression of IL-23. In a particular embodiment, the compositions of the invention are for use in treating or preventing diseases characterised by a decrease in the expression and/or activity of IL-23. In one embodiment, the compositions of the invention are for use in treating or preventing diseases by increasing the expression and/or activity of IL-23. In one embodiment, compositions of the invention are for use in promoting the immune response by increasing the expression and/or activity of IL-23.

The examples show that administration of the compositions of the invention can lead to an increase in expression of Tumour Necrosis Factor alpha (TNF-α). TNF-α is a pro-inflammatory cytokine which is known to be involved in various signalling pathways to promote cell death. TNF-α initiates apoptosis by binding to its cognate receptor, TNFR-1, which leads to a cascade of cleavage events in the apoptotic pathway [21]. TNF-α can also trigger necrosis via a RIP kinase-dependent mechanism [22]. Since administration of the compositions of the invention show an increase in TNF-α expression, compositions of the invention may be useful in the treatment of diseases, in particular for use in treating or preventing diseases characterised by a decrease in expression of by TNF-α. In one embodiment, the compositions of the invention are for use in treating diseases characterised by decreased TNF-α expression. In a particular embodiment, the compositions of the invention are for use in treating or preventing diseases characterised by a decrease in the expression and/or activity of TNF-α. In one embodiment, the compositions of the invention may be useful for treating or preventing diseases by increasing the expression and/or activity of TNF-α. In one embodiment, compositions of the invention are for use in promoting the immune response by increasing the expression and/or activity of TNF-α.

The examples also show that administration of the compositions of the invention can lead to an increase in expression of IL-6. IL-6 a pro-inflammatory cytokine that is produced during inflammation, and promotes the differentiation of naïve CD4$^+$ T cells and the differentiation of CD8$^+$ T cells into cytotoxic T cells [23]. Since administration of the compositions of the invention were shown to increase the expression of IL-6, compositions of the invention may be useful in the treatment of diseases characterised by a decrease in expression of IL-6. In a particular embodiment, the compositions of the invention are for use in treating or preventing diseases characterised by a decrease in the expression and/or activity of IL-6. In one embodiment, the compositions of the invention are for use in treating or preventing diseases by increasing the expression and/or activity of IL-6. In one embodiment, compositions of the invention are for use in promoting the immune response by increasing the expression and/or activity of IL-6.

Bettelli et al. [24] reported that IL-6 inhibits the expansion of Tregs. Since the examples show that compositions of the invention increase the expression of IL-6, compositions of the invention may selectively decrease the number or percentage of Tregs by increasing the expression of IL-6. In one embodiment, compositions of the invention are for use in immunostimulation by increasing the expression of IL-6. In another embodiment, compositions of the invention are for use in immunostimulation by decreasing the number or percentage of Tregs.

In some embodiments, stimulating the immune system according to the present invention comprises TLR5 activation or upregulation of TLR5 activation. In some embodiments, stimulating the immune system according to the present invention comprises TLR9 activation or upregulation of TLR9 activation. In some embodiments, stimulating the immune system according to the present invention comprises activation of TLR5 and TLR9 or upregulation of TLR9 and TLR5 activation. In some embodiments, stimulating the immune system according to the present invention comprises inducing and/or upregulating differentiation of T cells such as, but not limited to, T helper cells and T cytotoxic cells.

TLR signalling pathways culminate in the activation of the transcription factor nuclear factor-kappaB (NF-κB). NF-κB controls the expression of an array of inflammatory cytokine genes, including TNF-α. Immune stimulation causes, for example, the dimerization of TLR5, which subsequently recruits MyD88 and activates protein kinases, including IRAK1, IRAK2, IRAK4 and IRAN-M. The activation of these kinases leads to the nuclear localization of NF-κB, which is a proinflammatory cytokine [25].

As demonstrated in the examples, compositions of the invention lead to an increase in expression of NF-κB. Since administration of the compositions of the invention increase the expression of the proinflammatory cytokine NF-κB, compositions of the invention may be useful in stimulating the immune response. In addition, compositions of the invention may be useful in the treatment of disease, in particular diseases characterised by reduced immune activation and/or diseases treatable by an increased immune response. In one embodiment, the compositions of the invention are for use as an immune stimulant by increasing the level and/or activity of NF-κB. In one embodiment, the compositions of the invention are for use in treating diseases characterised by reduced immune activation by increasing the level and/or activity of NF-κB. In one embodiment, the compositions of the invention are for use in treating diseases treatable by an increased immune response by increasing the level and/or activity of NF-κB.

In particular, compositions of the invention may be useful in the treatment of diseases characterised by a decrease in expression and/or activation of NF-κB. In one embodiment, the compositions of the invention are for use in treating diseases characterised by a decrease in expression and/or activation of NF-κB.

The activation of NF-κB is important for eliciting innate immune responses and the subsequent development of adaptive immune responses. Thus, agonists of TLRs, such as compositions of the invention, are likely to be useful as adjuvants to treat infectious diseases, allergies and tumours by promoting both innate and adaptive immune responses [25]. In one embodiment, the compositions of the invention are for use in treating infectious diseases, allergies and/or tumours. In one embodiment, the compositions of the invention are for use in treating infectious diseases, allergies and/or tumours by increasing the level and/or activity of NF-κB.

The examples also demonstrate that the compositions of the invention promote the differentiation of T-helper cells and cytotoxic T lymphocytes. Therefore, in certain embodiments, the compositions of the invention are for use in stimulating the differentiation of T-helper cells and/or cytotoxic T lymphocytes. In certain embodiments, the disease to be treated by the compositions of the invention is not cancer.

Use as a Vaccine Adjuvant

The examples show that administration of the compositions of the invention can lead to an increase in expression of Tumour Necrosis Factor alpha (TNF-α). TNF-α is known to be important for vaccine responses. For example, TNF-α has been shown to be required for an efficient vaccine response in a flu vaccination of the elderly population [26]. Since administration of the compositions of the invention were shown to increase TNF-α expression, compositions of the invention may be useful as a vaccine adjuvant. In one embodiment, the compositions of the invention are for use as a vaccine adjuvant by increasing the level and/or activity of TNF-α. In one embodiment, the compositions of the invention are for use as a vaccine adjuvant. In one embodiment, the compositions of the invention are for use as a vaccine adjuvant in influenza therapy. In certain embodiments, the compositions of the invention are for use in enhancing an immune response against an antigen. In certain embodiments, the invention provides a composition to be administered in combination with an antigen. In certain embodiments, the compositions of the invention are for administration to a patient shortly prior to or after vaccination.

*Enterococcus gallinarum* and in particular strain MRx0518 is flagellated and flagellins can be TLR5 agonists. TLR agonists are in development as vaccine adjuvants across a range of antigen types, particularly in the elderly population [27]. Also, the data in the examples confirm that MRx0518 flagellin is a TLR5 agonists. Therefore, the compositions of the invention may be useful as vaccine adjuvants, in particular for vaccine administered to elderly patients (e.g. over 40, 50, 60, 70 or 80 years of age), who may have reduced immune system activity. TLR5 signalling also plays a key role in age-associated innate immune responses [28]. In certain embodiments, the compositions are for use in enhancing an innate immune response. Although TLR5 agonists are in development as vaccine adjuvants, these are all known pathogens and/or synthetic. In contrast, the compositions of the invention comprise commensal bacteria.

The examples also show that administration of the compositions of the invention can lead to an increase in expression of IL-6. Increased IL-6 expression has been associated with vaccine responses for many diseases. For example, IL-6 was produced by CD14+CD16− inflammatory monocytes after adults were administered an influenza vaccine [29], and higher levels of IL-6 were associated with achieving a vaccine response to an influenza vaccine [30]. Furthermore, IL-6 was produced after injection of the AS03 adjuvant system [31] and downregulation of IL-6 in mice was shown to reduce the helper T cell response after administration of a tuberculosis vaccine [32]. Since administration of the compositions of the invention were shown to increase IL-6 expression, compositions of the invention may be useful as a vaccine adjuvant. In one embodiment, the compositions of the invention are for use as a vaccine adjuvant by increasing the level and/or activity of IL-6. In one embodiment, the compositions of the invention are for use as a vaccine adjuvant. In one embodiment, the compositions of the invention are for use as a vaccine adjuvant in tuberculosis therapy.

Furthermore, IL-6 and TNF-α expression have been shown to be correlated with the efficacy of a therapeutic HIV vaccine [Huang et al] a tuberculosis vaccine and a *chlamydia* vaccine [33]. Su et al. [34] showed that co-inoculation of IL-6 or TNF-α with the FMDV DNA vaccine resulted in increased IFN-γ expression by $CD4^+$ and $CD8^+$ T cells, higher expression of IL-4 in $CD4^+$ T cells and a higher antigen-specific cytotoxic response. Since administration of the compositions of the invention were shown to increase IL-6 and TNF-α expression, compositions of the invention may be useful as a vaccine adjuvant. In one embodiment, the compositions of the invention may be useful as a vaccine adjuvant by increasing the level and/or activity of TNF-α. In one embodiment, the compositions of the invention may be useful as a vaccine adjuvant by increasing the level and/or activity of IL-6. In a particular embodiment, the compositions of the invention may be useful as a vaccine adjuvant by increasing the level and/or activity of TNF-α and IL-6. In one embodiment, the compositions of the invention are for use as a vaccine adjuvant in HIV therapy. In one embodiment, the compositions of the invention are for use as a vaccine adjuvant in chlamydia therapy.

The examples also show that administration of the compositions of the invention can lead to an increase in expression of IL-1β. Li et al. [35] showed that the adjuvant aluminium hydroxide activated the secretion of IL-1β, and suggested that IL-1β itself can act as an adjuvant. Since administration of the compositions of the invention were shown to increase IL-1β expression, compositions of the invention may be useful as a vaccine adjuvant. The examples show that administration of the compositions of the invention can increase the ratio of $CD8^+$ T cells to Tregs. Adjuvants have been shown to stimulate $CD8^+$ T cells [36] and since administration of the compositions of the invention were shown to increase the ratio of $CD8^+$ T cells to Tregs, compositions of the invention may be useful as a vaccine adjuvant. In one embodiment, compositions of the invention are for use as a vaccine adjuvant. In one embodiment, the compositions of the invention are for use as a vaccine adjuvant by increasing the ratio of $CD8^+$ T cells to Tregs.

The examples also show that administration of the compositions of the invention can lead to an increase in expression or levels of CXCR3 ligands CXCL9 and CXCL10. Known adjuvants such as ASO3, CpG, GLA-SE, αGalCer all increase CXCL9 and 10 [37,38], which suggests the compositions of the invention will be effective as adjuvants. Also, CXCL9 and 10 are associated with IFNγ/Th1 responses and promote antibody responses [39]. In certain embodiments, the compositions of the invention are for use in promoting an antibody response against an antigen, in particular a pathogenic or cancer antigen. Also, CXCL9 is a more sensitive measure than IFN-γ of vaccine induced T-cell responses in volunteers receiving investigated malaria vaccines [40]. In certain embodiments, the compositions of the invention are for use in promoting an T-cell response against an antigen, in particular a pathogenic or cancer antigen. In one embodiment, the compositions of the invention are for use as a vaccine adjuvant by increasing the level and/or activity of CXCL9 and CXCL10. In certain embodiments, the compositions are for use in protecting against malaria.

The examples also show that administration of the compositions of the invention can lead to an increase in expression or levels of IL-12p70. This effect has been associated with vaccine adjuvant efficiency and IL-12 has been proposed as an adjuvant itself [41], which suggests the compositions of the invention will be effective as adjuvants. In one embodiment, the compositions of the invention are for use as a vaccine adjuvant by increasing the level and/or activity of IL-12p70.

In some embodiments, when used as a vaccine adjuvant, the compositions of the invention will be administered on their own to provide an adjuvant effect for an antigen that has been separately administered to the patient. In certain embodiments, the composition of the invention is administered orally, whilst the antigen is injected parenterally.

The compositions of the invention may be used for enhancing an immune response to any useful antigen. Exemplary antigens for use with the invention include: viral antigens, such as viral surface proteins; bacterial antigens, such as protein and/or saccharide antigens; fungal antigens; parasite antigens; and tumour antigens. The invention is particularly useful for vaccines against influenza virus, HIV, hookworm, hepatitis B virus, herpes simplex virus, rabies, respiratory syncytial virus, cytomegalovirus, *Staphylococcus aureus, chlamydia*, SARS coronavirus, varicella zoster virus, *Streptococcus pneumoniae, Neisseria meningitidis,*

*Mycobacterium tuberculosis, Bacillus anthracis*, Epstein Barr virus, human papillomavirus, etc. Further antigens for use with the invention include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol or opiates.

Preferred antigens for use with the invention include pathogen antigens and tumour antigens. An antigen will elicit an immune response specific for the antigen that will be effective for protecting against infection with the pathogen or attacking the tumour. Antigens may be, for example, peptides or polysaccharides.

The invention also provides the use of: (i) an aqueous preparation of an antigen; and (ii) a composition comprising a bacterial strain of the species *Enterococcus gallinarum*, in the manufacture of a medicament for raising an immune response in a patient.

The immune response raised by these methods and uses will generally include an antibody response, preferably a protective antibody response.

In some embodiments, a bacterial strain of the species *Enterococcus gallinarum* is engineered to present an antigen. Presenting an antigen on the bacterial strain of the invention may maximise the immunostimulatory activities and further enhance the protective immune response generated against the antigen. In addition, manufacturing and delivering therapeutics comprising an antigen and a bacteria of the invention may be more efficient and effective this way than when each of the antigen and the composition comprising the bacterial strain are manufactured and administered separately. Therefore, in some embodiments, the invention provides a composition comprising a bacterial strain of the species *Enterococcus gallinarum* that presents an antigen, for example on its cell surface. In some embodiments, the composition comprising the bacterial strain that presents an antigen is for use as a vaccine antigen. In some embodiments, the antigen is derived from HIV, hookworm, hepatitis B virus, herpes simplex virus, rabies, respiratory syncytial virus, cytomegalovirus, *Staphylococcus aureus, chlamydia*, SARS coronavirus, varicella zoster virus, *Streptococcus pneumoniae, Neisseria meningitidis, Mycobacterium tuberculosis, Bacillus anthracis*, Epstein Barr virus or human papillomavirus. In some embodiments, the antigen is a glycoprotein antigen, lipoglycan antigen, archaea antigen, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 or a habit forming substance, such as, alcohol, opiates and the like.

In some embodiments, the bacteria of the invention express one or more antigens. Generally the antigen will be expressed recombinantly and will be heterologous to the bacteria of the invention. Therefore, the invention provides a bacterial strain of the species *Enterococcus gallinarum* that expresses a heterologous antigen. The antigen may be part of a fusion polypeptide expressed with one or more polypeptides homologous to the bacteria. In some embodiments, the bacteria express the antigen as a non-fusion polypeptide. In some embodiments, the invention provides a composition comprising a cell of a bacterial strain of the species *Enterococcus gallinarum*, wherein the cell expresses a heterologous antigen. In some embodiments, the composition is for use as a vaccine. In some embodiments, the invention provides a cell of a bacterial strain of the species *Enterococcus gallinarum*, wherein the cell expresses a heterologous antigen. In some embodiments, the cell is for use as a vaccine.

Exemplary antigens for use with the invention include: viral antigens, such as viral surface proteins; bacterial antigens, such as protein and/or saccharide antigens; fungal antigens; parasite antigens; and tumor antigens. Further antigens for expressing in a bacterial strain of the species *Enterococcus gallinarum* include glycoprotein and lipoglycan antigens, archaea antigens, melanoma antigen E (MAGE), Carcinoembryonic antigen (CEA), MUC-1, HER2, sialyl-Tn (STn), human telomerase reverse transcriptase (hTERT), Wilms tumour gene (WT1), CA-125, prostate-specific antigen (PSA), Epstein-Barr virus antigens, neoantigens, oncoproteins, amyloid-beta, Tau, PCSK9 and habit forming substances, for example nicotine, alcohol, opiates, or the like.

The invention may also be useful for enhancing the response to vaccines against non-communicable diseases such as elevated cholesterol (e.g. via the PCSK9 antigen).

The invention may also be useful for enhancing the response to vaccines against habit forming substances, for example nicotine, alcohol or opiates.

Cell Therapies

Chimeric Antigen Receptor T Cell (CAR-T) Therapy

The examples also show that administration of the compositions of the invention can lead to an increase in expression of IL-6. Increased IL-6 expression has been correlated with response to CD19 CAR-T therapy of chronic lymphocyte leukaemia. An increase in serum IL-6 was associated with CAR-T cell expansion, whereas inhibition of IL-6 was associated with inhibition of CAR-T cell proliferation [42]. Since administration of the compositions of the invention were shown to increase IL-6 expression, compositions of the invention may be useful in cell therapy, in particular CAR-T cell therapy. In one embodiment, the compositions of the invention are for use in cell therapy. In one embodiment, the compositions of the invention are for use in CAR-T cell therapy. In one embodiment, compositions of the invention are for use in the treatment of chronic lymphocyte leukaemia.

Selective depletion of Tregs has been shown to enhance the efficacy of cytotoxic lymphocytes [43]. CAR-T cells are a subset of cytotoxic lymphocytes, and therefore it is thought that selective depletion of Tregs is effective in CAR-T cell therapy. Since administration of the compositions of the invention were shown to deplete Tregs, compositions of the invention may be useful in cell therapy, in particular CAR-T cell therapy.

Therefore, the compositions of the invention may be useful in cell therapy, in particular in enhancing the response to a cell therapy.

Mesenchymalstem Cell (MSC) Therapy

Mesenchymal stem cell (MSC) therapy has been reported to have immunostimulatory properties. When MSCs are treated with LPS, they upregulate pro-inflammatory cytokines IL-6 and IL-8 which causes increased B cell proliferation [44]. Therefore, since compositions of the invention were shown to increase the expression of IL-6, they may be useful in combination with MSC cell therapy.

Stem Cell Transplantation Therapy

It has been reported that, instead of using undifferentiated stem cells in stem cell transplantation therapy, it may be beneficial to differentiate stem cells to some extent prior to transplantation. For example, Heng et al. [45] reported that cardiomyogenic differentiation of stem cells may be beneficial by having a higher engraftment efficiency, enhanced regeneration of myocytes and increased restoration of heart function. Since administration of the compositions of the invention initiated neuronal differentiation in undifferentiated neuroblastoma cells, compositions of the invention may be useful for stem cell differentiation in stem cell transplantation therapy.

Hematopoietic Stem Cell Transplantation

Hematopoietic stem cell transplantation is the transplantation of multipotent hematopoietic stem cells, usually derived from bone marrow, peripheral blood, or umbilical cord blood. Colonisation of the gut with Enterococci (*Enterococcus gallinarum* and *Enterococcus casseliflavus*) prior to allogenic hematopoietic stem cell transplantation has been shown to lead to a significantly improved the 2-year survival of patients after due to decreased nonrelapse mortality [46]. Therefore, the immunomodulatory effect shown in the examples may be useful in hematopoietic stem cell transplantation therapy. In certain embodiments, the compositions of the invention may be useful in improving survival after hematopoietic stem cell transplantation and in particular after allogenic hematopoietic stem cell transplantation.

The compositions of the invention may be useful in combination with allogenic hematopoietic stem cell transplantation. The compositions of the invention may be effective in boosting successful patient response to allogenic hematopoietic stem cell transplantation. In certain embodiments, the compositions of the invention are administered prior to hematopoietic stem cell transplantation. In certain embodiments, the compositions of the invention are for administration to a patient scheduled to receive hematopoietic stem cell transplantation. In certain embodiments, the compositions of the invention are administered following hematopoietic stem cell transplantation. In certain embodiments, the compositions of the invention are for administration to a patient that has received hematopoietic stem cell transplantation.

Immunosenescence

Fulop et al [47] identified that an increase in Treg cell number and a decrease in B cell number are associated with aging in the adaptive immune system. Therefore, compositions of the invention may be used to prevent or delay immunosenescence. In one embodiment, compositions of the invention are for use in preventing immunosenescence. In another embodiment, compositions of the invention are for use in delaying immunosenescence characterised by an increase in Treg cell number. In another embodiment, compositions of the invention are for use in delaying immunosenescence characterised by a decrease in B cell number. In another embodiment, compositions of the invention are for use in delaying immunosenescence characterised by an increase in Treg cell number and a decrease in B cell number. In one embodiment, compositions of the invention are for use in delaying immunosenescence by decreasing Treg cell number. In one embodiment, compositions of the invention are for use in delaying immunosenescence by increasing B cell number. In another embodiment, compositions of the invention are for use in delaying immunosenescence by decreasing Treg cell number and increasing B cell number. In one embodiment, compositions of the invention are for use in treating diseases caused by immunosenescence. In one embodiment, compositions of the invention are for use in treating aging-related diseases by delaying and/or preventing immunosenescence.

Furthermore, it has been proposed that vaccine adjuvants may overcome immunosenescence [48]. Since the compositions of the invention are suitable for use as a vaccine adjuvant, compositions of the invention may be useful for preventing or delaying immunosenescence. In another embodiment, compositions of the invention are for use in delaying and/or preventing immunosenescence as a vaccine adjuvant. In another embodiment, compositions of the invention are for use as a vaccine adjuvant, wherein the compositions delay and/or prevent immunosenescence.

Diseases that are associated with immunosenescence include cardiovascular disease, cancer, diabetes mellitus type 2 [49] and autoimmune disorders [50].

Modes of Administration

Preferably, the compositions of the invention are to be administered to the gastrointestinal tract in order to enable delivery to and/or partial or total colonisation of the intestine with the bacterial strain of the invention. Generally, the compositions of the invention are administered orally (including sublingual), but they may be administered rectally or intranasally.

In certain embodiments, the compositions of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to reduce the likelihood of disease developing in her child in utero and/or after it is born.

The compositions of the invention may be administered to a patient that has been diagnosed with a disease or condition mediated reduced immune activity, or that has been identified as being at risk of a disease or condition mediated by reduced immune activity. The compositions may also be administered as a prophylactic measure to prevent the development of diseases or conditions mediated by reduced immune activity in a healthy patient.

The compositions of the invention may be administered to a patient that has been diagnosed with deficient immune activity, or that has been identified as being at risk of deficient immune activity. For example, the patient may have reduced or absent colonisation by *Enterococcus*, and in particular *Enterococcus gallinarum*.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [51,52].

Alternatively, the composition of the invention may comprise a live, active bacterial culture.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [53] and [54].

The composition may be administered orally and may be in the form of a tablet, capsule or powder. Encapsulated products are preferred because *Enterococcus* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU; in another example from about $1 \times 10^7$ to about $1 \times 10^{11}$ CFU; in another example from about $1 \times 10^8$ to about $1 \times 10^{10}$ CFU; in another example from about $1 \times 10^8$ to about $1 \times 10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1 \times 10^6$ to about $1 \times 10^{11}$ CFU/g, respect to the weight of the composition; for example, from about $1 \times 10^8$ to about $1 \times 10^{10}$ CFU/g. The dose may be, for example, 1 g, 3 g, 5 g, and 10 g.

In certain embodiments, the invention provides the above pharmaceutical composition, wherein the amount of the bacterial strain is from about $1 \times 10^3$ to about $1 \times 10^{11}$ colony forming units per gram with respect to a weight of the composition.

In certain embodiments, the invention provides the above pharmaceutical composition, wherein the composition is administered at a dose of between 500 mg and 1000 mg, between 600 mg and 900 mg, between 700 mg and 800 mg, between 500 mg and 750 mg or between 750 mg and 1000 mg. In certain embodiments, the invention provides the above pharmaceutical composition, wherein the lyophilised bacteria in the pharmaceutical composition is administered at a dose of between 500 mg and 1000 mg, between 600 mg and 900 mg, between 700 mg and 800 mg, between 500 mg and 750 mg or between 750 mg and 1000 mg.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [55]. Acceptable carriers or diluents for therapeutic use are well known in the pharmaceutical art and are described, for example, in reference [56]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism.

The compositions for use in accordance with the invention may or may not require marketing approval.

In some cases, the lyophilised bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition.

In certain embodiments, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by pro-inflammatory cytokines, such as IL-1β, TNF-α, MIP-3α, IL-23 or IL-6. In a preferred embodiment, the invention provides pharmaceutical composition comprising: a bacterial strain of the invention; and a pharmaceutically acceptable excipient, carrier or diluent; wherein the bacterial strain is in an amount sufficient to treat or prevent a disease or condition mediated by TNF-α.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

Culturing Methods

The bacterial strains for use in the present invention can be cultured using standard microbiology techniques as detailed in, for example, references [57,58].

The solid or liquid medium used for culture may be YCFA agar or YCFA medium. YCFA medium may include (per 100 mL, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH$_4$)$_2$SO$_4$ (0.09 g), MgSO$_4$.7H$_2$O (0.009 g), CaCl$_2$ (0.009 g), resazurin (0.1 mg), hemin (1 mg), biotin (1 μg), cobalamin (1 μg), p-aminobenzoic acid (3 μg), folic acid (5 μg), and pyridoxamine (15 μg).

Bacterial Strains for Use in Vaccine Compositions

The inventors have identified that the bacterial strains of the invention are useful for treating or preventing diseases or conditions associated with reduce immune activity. This is likely to be a result of the effect that the bacterial strains of the invention have on the host immune system. Therefore, the compositions of the invention may also be useful for preventing diseases or conditions, when administered as vaccine compositions. In certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [59] and [60,61], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [62]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [63].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Efficacy of Bacterial Inocula in Mouse Models of Cancer

Summary

This study tested the efficacy of compositions comprising bacterial strains according to the invention in four tumor models.

Materials

Test substance—Bacterial strain #MRx0518.

Reference substance—Anti-CTLA-4 antibody (clone: 9H10, catalog: BE0131, isotype: Syrian Hamster IgG1, Bioxcell).

Test and reference substances vehicles—Bacterial culture medium (Yeast extract, Casitone, Fatty Acid medium (YCFA)). Each day of injection to mice, antibody was diluted with PBS (ref: BE14-516F, Lonza, France).

Treatment doses—Bacteria: $2 \times 10^8$ in 200 pt. The anti-CTLA-4 was injected at 10 mg/kg/inj. Anti-CTLA-4 was administered at a dose volume of 10 mL/kg/adm (i.e. for one mouse weighing 20 g, 200 µL of test substance will be administered) according to the most recent body weight of mice.

Routes of administration—Bacterial inoculum was administered by oral gavage (per os, PO) via a cannula. Cannulas were decontaminated every day. Anti-CTLA-4 was injected into the peritoneal cavity of mice (Intraperitoneally, IP).

Culture conditions of bacterial strain—The culture conditions for the bacterial strain were as follows:

Pipette 10 mL of YCFA (from the prepared 10 mL E&O lab bottles) into Hungate tubes Seal the tubes and flush with $CO_2$ using a syringe input and exhaust system Autoclave the Hungate tubes When cooled, inoculate the Hungate tubes with 1 mL of the glycerol stocks Place the tubes in a static 37° C. incubator for about 16 hours.

The following day, take 1 mL of this subculture and inoculate 10 mL of YCFA (pre-warmed flushed Hungate tubes again, all in duplicate)

Place them in a static 37° C. incubator for 5 to 6 h

Cancer Cell Line and Culture Conditions—

The cell lines that were used are detailed in the table below:

| Cell line | Type | Mouse strain | Origin |
|---|---|---|---|
| EMT-6 | Breast carcinoma | BALB/c | ATCC |
| LL/2 (LLC1) | Lung carcinoma | C57BL/6 | ATCC CRL1642 |
| Hepa1-6 | Hepatocellular carcinoma | C57BL/6 | IPSEN INNOVATION |
| RENCA | Renal adenocarcinoma | BALB/c | ATCC |

The EMT-6 cell line was established from a transplantable murine mammary carcinoma that arose in a BALB/cCRGL mouse after implantation of a hyperplastic mammary alveolar nodule [64].

The LL/2 (LLC1) cell line was established from the lung of a C57BL/6 mouse bearing a tumour resulting from an implantation of primary Lewis lung carcinoma [65].

The Hepa 1-6 cell line is a derivative of the BW7756 mouse hepatoma that arose in a C57/L mouse [66].

Cell culture conditions—All cell lines were grown as monolayer at 37° C. in a humidified atmosphere (5% $CO_2$, 95% air). The culture medium and supplement are indicated in the table below:

| Cell line | Culture medium | Supplement |
|---|---|---|
| EMT6 | RPMI 1640 containing 2 mM L-glutamine (ref: BE12-702F, Lonza) | 10% foetal bovine serum (ref: #3302, Lonza) |
| LL/2 (LLC1) | RPMI 1640 containing 2 mM L-glutamine (ref: BE12-702F, Lonza) | 10% foetal bovine serum (ref: #3302, Lonza) |
| Hepa1-6 | DMEM (ref:11960-044, Gibco) | 10% foetal bovine serum (ref: #3302, Lonza) 2 mM L-Glutamine penicillin-streptomycin (Sigma G-6784) |
| RENCA | DMEM | 10% fetal bovine serum, 2 mM L-glutamine, 1 ug/mL puromycin |

For experimental use, adherent tumour cells were detached from the culture flask by a 5 minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability will be assessed by 0.25% trypan blue exclusion assay.

Use of Animals—

Healthy female BALB/C (BALB/cByJ) mice, of matching weight and age, were obtained from CHARLES RIVER for the EMT6 and RENCA model experiments.

Healthy female C57BL/6 (C57BL16J) mice, of matching weight and age, were obtained from CHARLES RIVER (L'Arbresles) for the LL/2(LLC1) and the Hepa1-6 model experiments.

Animals were maintained in SPF health status according to the FELASA guidelines, and animal housing and experimental procedures according to the French and European Regulations and NRC Guide for the Care and Use of Laboratory Animals were followed [67,68]. Animals were maintained in housing rooms under controlled environmental conditions: Temperature: 22±2° C., Humidity 55±10%, Photoperiod (12 h light/12 h dark), HEPA filtered air, 15 air exchanges per hour with no recirculation. Animal enclosures were provided with sterile and adequate space with bedding material, food and water, environmental and social enrichment (group housing) as described: 900 $cm^2$ cages (ref: green, Tecniplast) in ventilated racks, Epicea bedding (SAFE), 10 kGy Irradiated diet (A04-10, SAFE), Complete food for immuno-competent rodents—R/M-H Extrudate, water from water bottles.

Experimental Design and Treatments

Antitumor Activity, EMT6 Model

Treatment schedule—The start of first dosing was considered as D0. On D0, non-engrafted mice were randomized according to their individual body weight into groups of 9/8 using Vivo Manager® software (Biosystemes, Couternon, France). On D0, the mice received vehicle (culture medium) or bacterial strain. On D14, all mice were engrafted with EMT-6 tumor cells as described below. On D24, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 8 | Untreated | — | — | — |
| 2 | 8 | Vehicle (media) | — | PO | Q1Dx42 |
| 3 | 9 | Bacterial strain #1 (MRx0518) | $2 \times 10^8$ bacteria | PO | Q1Dx42 |
| 4 | 8 | Anti-CTLA4 | 10 mg/kg | IP | TWx2 |

The monitoring of animals was performed as described below.

Induction of EMT6 tumours in animals—On D14, tumours were induced by subcutaneous injection of $1 \times 10^6$ EMT-6 cells in 200 µL RPMI 1640 into the right flank of mice.

Euthanasia—Each mouse was euthanized when it reached a humane endpoint as described below, or after a maximum of 6 weeks post start of dosing.

Antitumor Activity, LL/2 (LLC1) Model

Treatment schedule—The start of first dosing was considered as D0. On D0, non-engrafted mice were randomized according to their individual body weight into 7 groups of 9/8 using Vivo Manager® software (Biosystemes, Couternon, France). On D0, the mice received vehicle (culture medium) or bacterial strain. On D14, all mice were engrafted with LL/2 tumor cells as described below. On D27, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 8 | Untreated | — | — | — |
| 2 | 9 | Vehicle (media) | — | PO | Q1Dx42 |
| 3 | 9 | Bacterial strain #1 (MRx0518) | $2 \times 10^8$ bacteria | PO | Q1Dx42 |
| 4 | 8 | Anti-CTLA4 | 10 mg/kg | IP | TWx2 |

The monitoring of animals was performed as described below.

Induction of LL/2 (LLC1) tumors in animals—On D14, tumors were induced by subcutaneous injection of $1 \times 10^6$ LL/2 (LLC1) cells in 200 µL RPMI 1640 into the right flank of mice.

Euthanasia—Each mouse was euthanized when it reached a humane endpoint as described below, or after a maximum of 6 weeks post start of dosing.

Antitumor Activity, Hepa1-6 Model

Treatment schedule—The start of first dosing was considered as D0. On D0, non-engrafted mice were randomized according to their individual body weight into 7 groups of 9 using Vivo Manager® software (Biosystemes, Couternon, France). On D0, the mice received vehicle (culture medium) or bacterial strain. On D14, all mice were engrafted with Hepa 1-6 tumor cells as described below. On D16, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 9 | Untreated | — | — | — |
| 2 | 9 | Vehicle (media) | — | PO | Q1Dx42 |
| 6 | 9 | Bacterial strain #4 (MRx0518) | $2 \times 10^8$ bacteria | PO | Q1Dx42 |
| 7 | 9 | Anti-CTLA4 | 10 mg/kg | IP | TWx2 |

The monitoring of animals was performed as described below.

Orthotopic induction of Hepa 1-6 tumor cells in animals by intrasplenic injection—On D0, one million ($1 \times 10^6$) Hepa 1-6 tumor cells in 50 μL RPMI 1640 medium were transplanted via intra-splenic injection into mice. Briefly, a small left subcostal flank incision was made and the spleen was exteriorized. The spleen was exposed on a sterile gauze pad, and injected under visual control with the cell suspension with a 27-gauge needle. After the cell inoculation, the spleen was excised.

Euthanasia—Each mouse was euthanized when it reached a humane endpoint as described in section below, or after a maximum of 6 weeks post start of dosing.

Evaluation of tumour burden at euthanasia—At the time of termination, livers were collected and weighed.

Antitumor Activity, RENCA Model

Treatment schedule—The start of first dosing was considered as D0. On D0, non-engrafted mice were randomized according to their individual body weight into groups of 12 mice. On D0, the mice received vehicle (culture medium) or bacterial strain ($2 \times 10^8$ in 100 μL, PO). On D14, all mice were engrafted with RENCA tumour cells injected SC into the left hind flank as described below. Treatment with anti-CTLA-4 (clone 9D9, 10 mg/kg, IP) and anti-PDL1 (clone 10F.9G2, 10 mg/kg, IP) was initiated from D17.

The treatment schedule is summarized in the table below:

| Group | No. Animals | Treatment | Dose | Route | Treatment Schedule |
|---|---|---|---|---|---|
| 1 | 12 | Untreated | — | — | — |
| 2 | 12 | Vehicle (media) | — | PO | QD |
| 3 | 12 | Bacterial strain (MRx0518) | $2 \times 10^8$ bacteria | PO | QD |
| 4 | 12 | Paclitaxel | 15 mg/kg | IP | Q4D (every four days) |
| 5 | 12 | Anti-CTLA4 + Anti-PDL1 | 10 mg/kg + 10 mg/kg | IP | BIW (twice weekly) From day 3 |

The monitoring of animals was performed as described below.

On D14 (following 2 weeks of bacterial dosing/pretreatment), $5 \times 10^5$ viable cells in 100 μL of PBS were injected subcutaneously into the left hind flank of each mouse (which was sterilised with surgical spirit), 1 syringe and needle per mouse. The implantation sites were shaved the day prior to cell implantation.

Euthanasia—Each mouse was euthanized when it reached a humane endpoint as described in section below, or after a maximum of 6 weeks post start of dosing.

Evaluation of tumour burden at euthanasia—At the time of termination, tumours were collected and their volume evaluated.

Animal Monitoring

Clinical monitoring—The length and width of the tumour was measured 2-3 times a week with callipers and the volume of the tumour was estimated by this formula [69]:

$$\text{Tumor volume} = \frac{\text{width}^2 \times \text{length}}{2}$$

Humane endpoints [70]: Signs of pain, suffering or distress: pain posture, pain face mask, behaviour; Tumor exceeding 10% of normal body weight, but non-exceeding 2000 mm$^3$; Tumors interfering with ambulation or nutrition; Ulcerated tumour or tissue erosion; 20% body weight loss remaining for 3 consecutive days; Poor body condition, emaciation, cachexia, dehydration; Prolonged absence of voluntary responses to external stimuli; Rapid laboured breathing, anaemia, significant bleeding; Neurologic signs: circling, convulsion, paralysis; Sustained decrease in body temperature; Abdominal distension.

Anaesthesia—Isoflurane gas anesthesia was used for all procedures: surgery or tumour inoculation, i.v. injections, blood collection. Ketamine and Xylazine anesthesia was used for stereotaxia surgical procedure.

Analgesia—Carprofen or multimodal carprofen/buprenorphine analgesia protocol were adapted to the severity of surgical procedure. Non-pharmacological care was provided for all painful procedures. Additionally, pharmacological care not interfering with studies (topic treatment) were provided at the recommendation of the attending veterinarian.

Euthanasia—Euthanasia of animals was performed by gas anesthesia over-dosage (Isoflurane) followed by cervical dislocation or exsanguination.

Results

Antitumor Activity, EMT6 Model

The results are shown in FIG. 1A. Treatment with the bacterial strain of the invention led to a clear reduction in tumour volume relative to both the negative controls. The positive control also led to a reduction in tumour volume, as would be expected.

To further elucidate the mechanisms through which MRx0518 conveys its therapeutic effects in syngeneic tumour models, ex vivo analysis was performed on the syngeneic EMT6 tumour model studies. While tumour volume is the primary measurement in preclinical oncology studies, tumours often consist of actively dividing tumour cells along with a necrotic core. To investigate whether MRx0518 treatment had influence on the degree of necrosis found within EMT6 tumours, paraffin sections from the mid-belly region of the tumours were stained with Haematoxylin and Eosin. MRx0518 treatment of a murine EMT6 breast carcinoma model showed a tendency towards increasing the cross-sectional area of necrosis within the tumour (FIG. 1B, upper panel). To investigate whether MRx0518 treatment had influence on dividing cells within the tumour, paraffin sections from the mid-belly region of the tumours were stained with the proliferation protein Ki67, along with DAPI counter stain, to estimate the percentage of cells dividing within the EMT6 tumour. MRx0518 treatment of a murine EMT6 breast carcinoma model significantly decreased the percentage of dividing cells seen within the tumour (FIG. 1B, lower panel, P=0.019).

Immune Cell Populations

Further investigation of the tumour microenvironment was performed through flow cytometry of the tumour, to investigate the hypothesis that the MRx0518 bacterial strain has the ability to regulate the immune system into inducing an anti-tumour effect. Tumours excised from the different treatment groups were cut into pieces. One piece was subjected to flow cytometry analysis. To assess the relative percentage of T lymphocytes, present within the tumours, the following markers were used: CD45, CD3, CD4, CD8, CD25 and FoxP3.

The preliminary flow cytometry data presented in FIG. 1C (and further supported by the below described data, presented in FIG. 23) shows that the relative percentage of lymphocytes in tumours was slightly decreased in both the MRx0518 and anti-CTLA-4 treated groups, when compared respectively to vehicle or control animals. Likewise, the relative percentage of CD4$^+$ cells appeared to be decreased in MRx0518 and anti-CTLA-4 treated animals, whilst the relative percentage of CD8$^+$ cells followed an opposite trend in both groups, albeit with different magnitude. The relative percentage of CD4$^+$FoxP3$^+$ cells was lower in the anti-CTLA-4 treated group when compared to the slight decrease in MRx0518 treated animals; however, the reduction in the relative percentage of CD4$^+$CD25$^+$ cells was noticeable only in the anti-CTLA-4 treated group. The CD8+/FoxP3+ ratio showed a greater increase in the anti-CTLA-4 treated group than in the MRx0518 animals. These data presented here supports the hypothesis that anti-CTLA-4 antibody targets regulatory T cells (Tregs) by reducing their cell numbers or attenuating their suppressive activity in tumour tissue, whilst suggesting a different mode of action for MRx0518.

Additional investigation of the tumour microenvironment was performed using NanoString analysis of the tumour tissues, to investigate whether the MRx0518 bacterial strain has the ability to regulate the immune system into inducing an anti-tumour effect in the EMT6 model. Tumours excised from vehicle and MRx0518-treated groups were collected. RNA was extracted from tumour tissue using TRIzol reagent (ThermoFisher) followed by a clean-up using the RNeasy Mini kit (Qiagen) including a DNase I treatment (Qiagen). RNA was then used for Nanostring analysis using the PanCancer Mouse 10 360 panel. Genes previously shown to be characteristic of various cell populations were used to measure these populations' abundance:

| Cell type | Marker genes |
| --- | --- |
| NK CD56dim cells | Il21r, Kir3dl1, Kir3dl2 |
| Exhausted CD8 | Cd244, Eomes, Lag3, Ptger4 |
| DC | Ccl2, Cd209e, Hsd11b1 |
| Cytotoxic cells | Ctsw, Gzma, Gzmb, Klrb1, Klrd1, Klrk1, Nkg7, Prf1 |
| Macrophages | Cd163, Cd68, Cd84, Ms4a4a |
| T-cells | Cd3d, Cd3e, Cd3g, Cd6, Sh2d1a, Trat1 |
| Mast cells | Cpa3, Hdc, Ms4a2 |
| Neutrophils | Ceacam3, Csf3r, Fcgr4, Fpr1 |
| B-cells | Blk, Cd19, Fcrlb, Ms4a1, Pnoc, Spib, Tcl1, Tnfrsf17 |
| NK cells | Ncr1, Xcl1 |
| CD45 | Ptprc |

Z-scores for each cell population were calculated using the linear cell type scores provided by the NanoString analysis (FIG. 23, heat map).

The NanoString data shows that the abundance of B cells, CD45, T cells, cytotoxic and NK cells were increased in the tumour tissue of MRx0518-treated group when compared to vehicle-treated animals (FIG. 23). The data presented here supports the hypothesis that MRx0518 has an immunostimulatory effect by increasing leukocytes, in particular NK cells, T cells and cytotoxic cells in the tumour microenvironment.

Cytokine Production

Figure 1D:
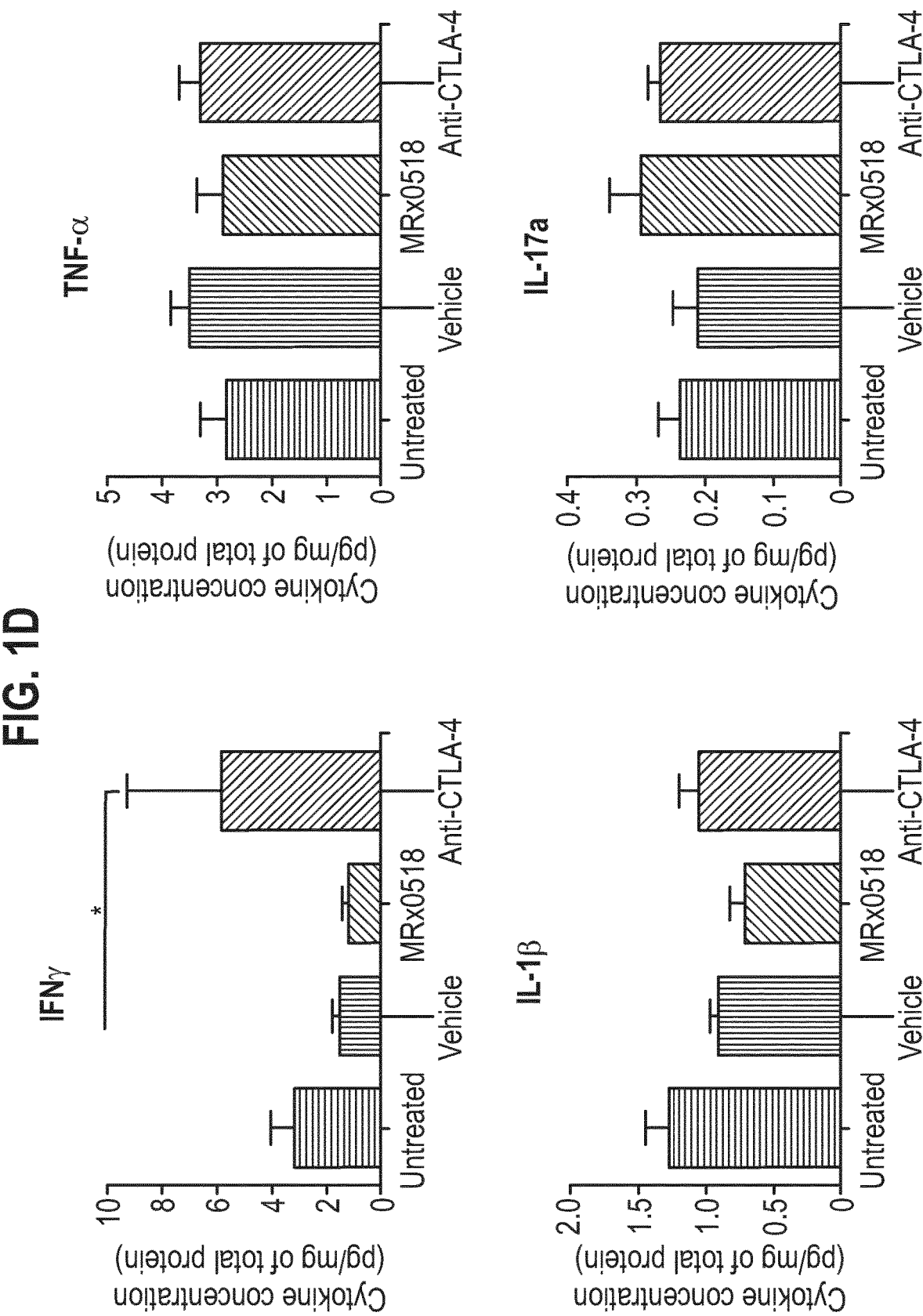
FIG. 1D: Mouse model of breast cancer—Cytokine production in tumour lysates. Columns represent the mean pg/mL of total protein from each treatment group. *p<0.05 between groups using one-way ANOVA followed by Dunnett's multiple comparisons test.

An additional tumour piece was used for total protein extraction and subsequent cytokine analysis, together with plasma samples. Protein levels of IL-10, CXCL1, CXCL2, CXCL10, IL-1β, IL-17A, GM-CSF, TNF-α, IL-12p70 and IFN-γ in the tumour microenvironment were analysed by MagPix technology. While IL-17A and GM-CSF were below levels of detection, all the other markers were expressed at reasonable levels (FIG. 1D). A significance difference was observed between the vehicle and anti-CTLA-4 group for IFN-γ. The production of the IL-10 and IL-12p70 immune markers seemed reduced following MRx0518 treatment compared to the control treatments.

Figure 1E:
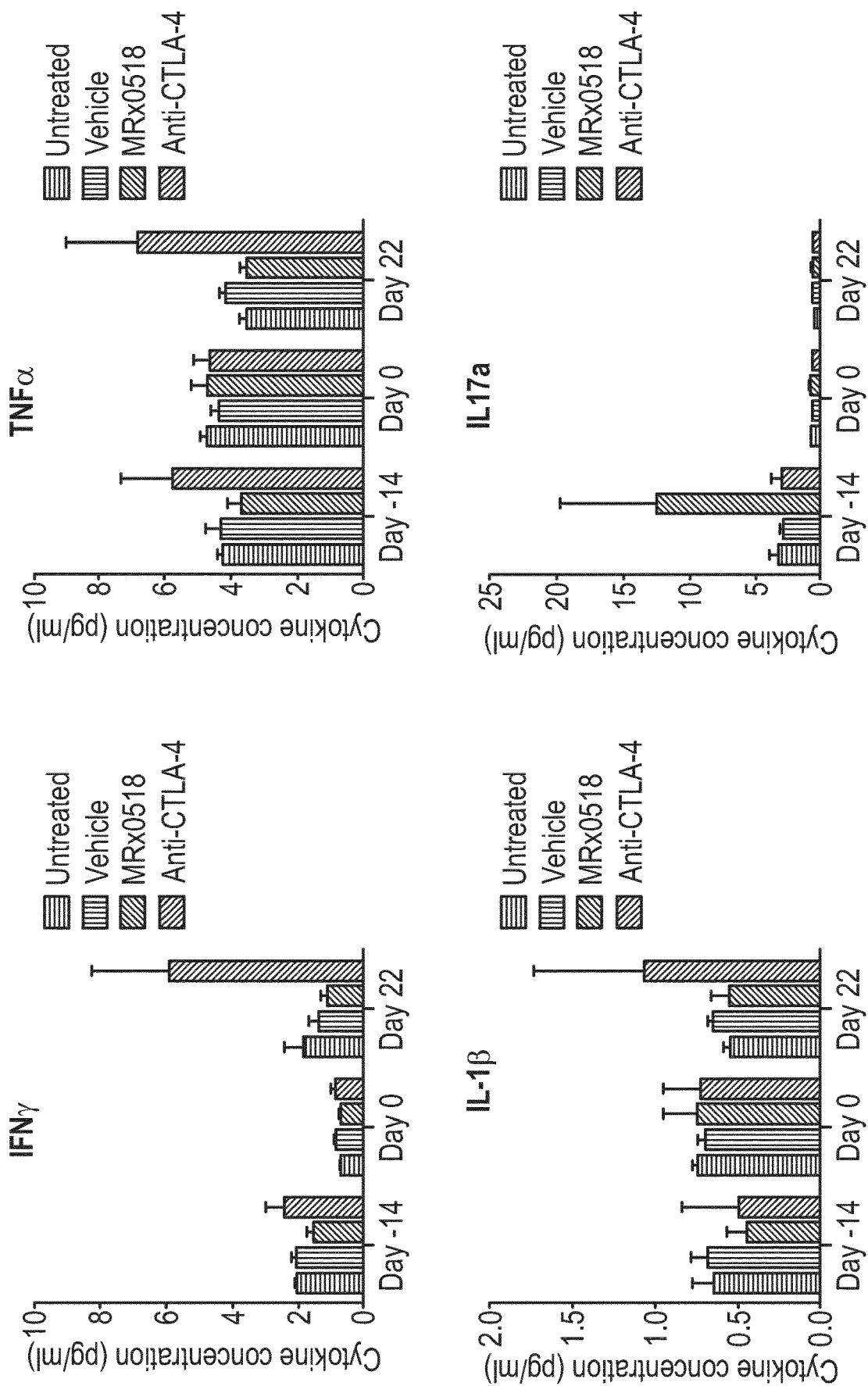
FIG. 1E: Mouse model of breast cancer—Cytokine production in blood plasma. Columns represent the mean pg/mL from each treatment group (+/−SEM).

Cytokine levels were also assessed in blood plasma of the same animals. Protein levels of IL-23, IL-6, IL-10, VEGF, CXCL1, CXCL2, CXCL10, IL-2, IL-1β, IL-17A, GM-CSF, TNF-α, IL-12p70 and IFN-γ were analysed by MagPix technology. Overall, little cytokine production was detected in the blood plasma of animals either before tumour induction or at the end of the study (FIG. 1E). VEGF and CXCL10 were detected at substantial levels, while IL-23, IL-6, IL-10, CXCL1 and CXCL2 were detected at low levels. IL-2, IL-1b, IL-17A, GM-CSF, TNF-α, IL-12p70 and IFN-γ were not detected in the samples. MRx0518 significantly increased production of IL-6 at Day 0. MRx0518 also seemed to increase IL-23 production. VEGF and CXCL10 were significantly downregulated in the anti-CLTA-4 group at Day 22. Similarly to the results shown for the immune cell populations, the differences in cytokine production in the tumour and plasma, between MRx0518 and ant-CTLA-4 suggests that each of them acts on a distinct and potentially complementary mechanism.

Localisation of CD8a Positive Cells in the Ileum

10 μm cryo-sections of ileum were cut in cryostat (CM 1950 Leica), picked up onto poly-L Lysine slides. The sections were then air-dried for 1 hour, fixed for 10 minutes in ice-cold methanol, washed in PBS, blocked in 10% BSA in PBS pH 7.2 before being incubated overnight with the primary antibody (rat-anti-mouse-CD8α antibody, Sigma-Aldrich, Millipore).

Figure 1F:
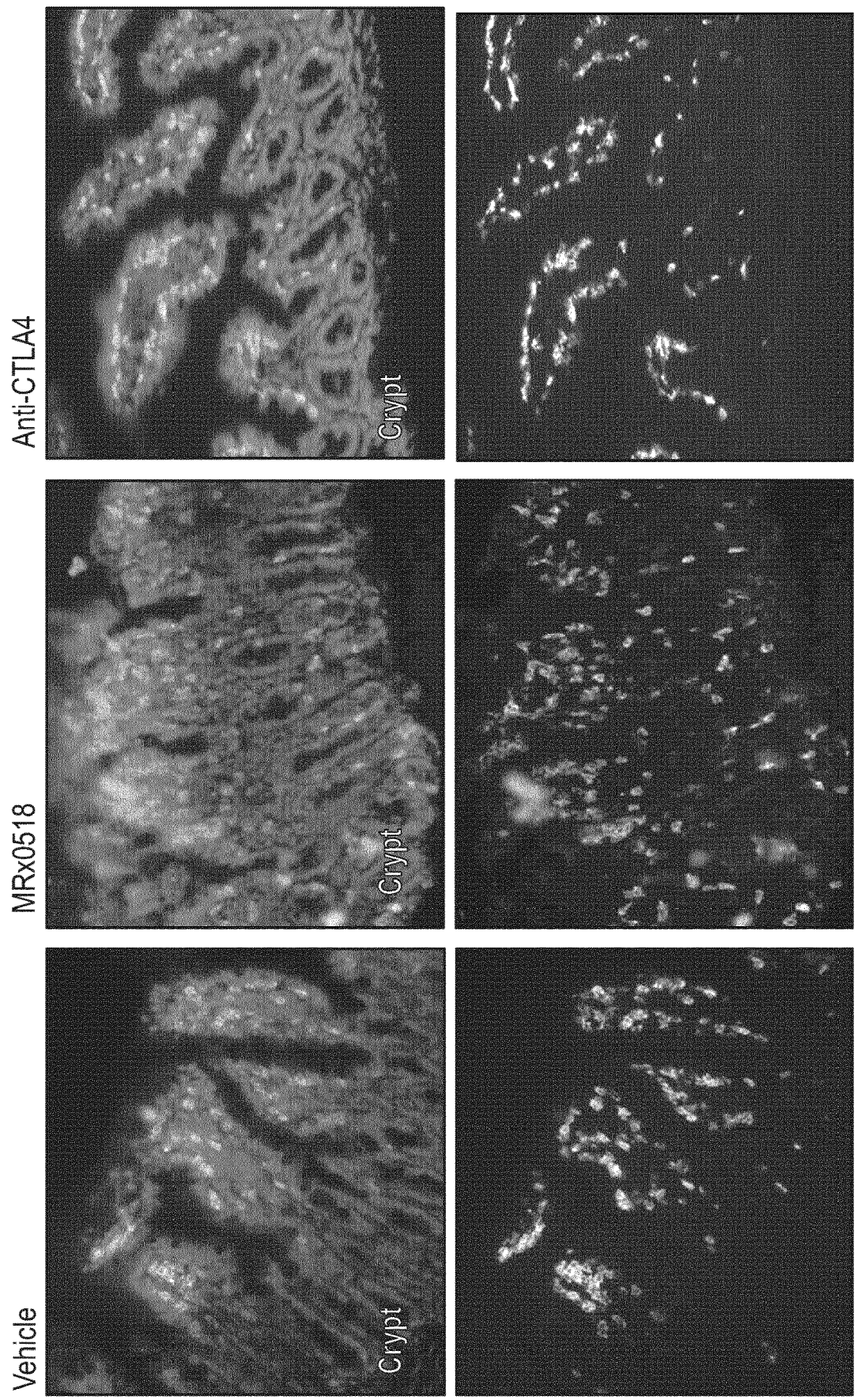
FIG. 1F: Representative images of ileum cryosections from vehicle, MRx0518 and anti-CTLA-4-treated mice immuno-labelled with antibodies against CD8a (lower panels) and counter-stained with DAPI (upper panels).

The next morning the slides were washed in PBS and stained with a secondary antibody: goat-anti-rat-antibody-Alexa488 (Molecular Probe, Invitrogen) for 1 hour at room temperature. After another washing step, the slides were counterstained with 4',6-diamidino-2-phenylindole dihydrochloride (DAPI) (Sigma-Aldrich, Millipore) and mounted in Vectashield (Vector Laboratories). The slides were viewed and imaged using a Zeiss Axioscope Microscope equipped with a mercury vapour lamp, appropriate filters and a ×20 apochromatic objective. Examples of images obtained from slides from the vehicle, MRx0518, and anti-CTLA4 animals are shown (FIG. 1F—upper panels: DAPI staining, lower panels: CD8α staining).

Fields of view were examined from 20 animals and imaged using manual exposure time. The number of animals and fields analysed are shown in the following table:

| Group | Number of fields analysed | Number of mice |
|---|---|---|
| Vehicle | 53 | 5 |
| MRx0518 | 70 | 7 |
| Anti-CTLA4 | 71 | 8 |

Figure 1G:
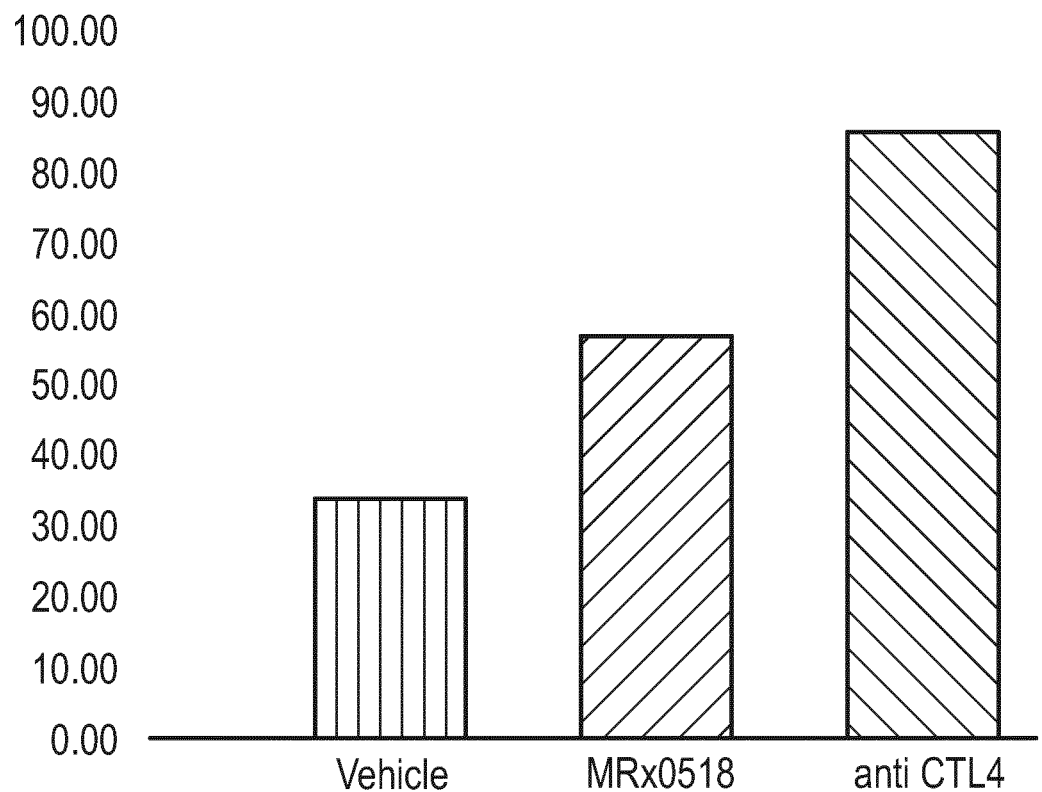
FIG. 1G: Plot quantifying animal study subsets with more than 3 CD8α+ cells per field taken from the ileum crypt region of mice treated with vehicle, MRx0518 or anti-CTLA-4.

The images were scored as follow: fields with ≤3 positive cells were scored as 0, whilst fields with more ≥3 cells were scored as 1. The results of this analysis are shown (FIG. 1G).

Ileum cryosections stained with anti-CD8α showed a higher number of CD8α positive cells localized in the crypt region tissues from animals treated with MRx0518 and anti-CTLA-4 compared to the vehicle group.

This observation is in line with CD8$^+$ T cells being present in the intestine in case of infection or inflammatory microenvironment, as part of the immune response.

Antitumor Activity, LL/2 (LLC1) Model

The results are shown in FIG. 2. Treatment with the bacterial strain of the invention led to a clear reduction in tumour volume relative to both the negative controls.

Antitumor Activity, Hepa1-6 Model

The results are shown in FIG. 3A. The untreated negative control does not appear as would be expected, because liver weight was lower in this group than the other groups. However, the vehicle negative control and the positive control groups both appear as would be expected, because mice treated with vehicle alone had larger livers than mice treated with anti-CTLA4 antibodies, reflecting a greater tumour burden in the vehicle negative control group. Treatment with the bacterial strain of the invention led to a clear reduction in liver weight (and therefore tumour burden) relative to the mice in the vehicle negative control group.

Antitumor Activity, RENCA Model

The results are shown in FIG. 3B. Treatment with MRx0518 monotherapy reduced tumour volume with Test/Control of 51% (day 18) compared with the vehicle-treated groups. Paclitaxel and anti-CTLA-4+ anti-PDL-1 showed an (almost) complete reduction in tumour size at D18 and D22 compared to both the untreated and vehicle groups.

These data indicate that strain MRx0518 may be useful for treating or preventing other diseases associated with reduced immune system activity.

Example 2—PCR Gene Analysis

A pure culture of bacteria MRx0518 was studied in a PCR gene analysis. There were two arms to the experiment: 1) MRx0518 was co-cultured with human colonic cells (CaCo2) to investigate the effects of the bacteria on the host, and 2) MRx0518 was co-cultured on CaCo2 cells that were stimulated with IL1 to mimic the effect of the bacteria in an inflammatory environment. The effects in both scenarios were evaluated through gene expression analysis. The results are shown below:

| Gene | Fold change | Function |
|---|---|---|
| CXCL3 | 28412.73 | CXCR2 ligand, |
| CXCL2 | 135.42 | CXCR2 ligand, 90% homology with CXCL1. |
| CXCL9 | 34.76 | CXCR3 ligand, primarily thought of as Th1 cell chemoattractant (inducible by IFN-g) |
| IL8 | 31.81 | Cytokine, chemoattractant (especially neutrophils), many receptors including CXCR1 and CXCR2/ |
| CXCL1 | 16.48 | CXCR2 ligand, stimulates cell proliferation as well as migration, overexpression is neuroprotective in EAE. |
| CD40 | 14.33 | Co-stimulatory molecule, route of T cell dependent DC activation. |
| TNF | 13.50 | Major proinflammatory cytokine |
| IL17C | 12.18 | Promotes antibacterial response from epthielium, synergistic with IL-22, |
| CXCL10 | 10.66 | Close homology with CXCL9, think also CXCR3 ligand? |
| HSPA1B | 10.19 | Heat shock protein |
| NFKBIA | 8.87 | NFκB signalling; PI3K |
| JUN | 7.61 | Antibacterial response; GPCR signalling. |
| TNFAIP3 | 6.63 | TNF signalling |
| DUSP1 | 6.36 | Anti-inflammatory phosphatase, inactivates MAPKs |
| JUNB | 5.36 | Transcription factor, JAK-STAT signalling |
| BIRC3 | 4.86 | Adherens junctions, tight junctions |
| DUSP2 | 4.59 | Anti-inflammatory, inactivates MAPK. |
| IL32 | 4.29 | Proinflammatory cytokine, induced by IFN-g, IL-18 |
| DUSP5 | 3.12 | Anti-inflammatory, inactivates MAPK |
| FOS | 3.03 | Transcription factors, TLR signalling, forms part of AP-1 |
| GADD45B | 2.89 | Cell growth and proliferation |
| CLDN4 | 2.61 | Tight junctions |
| ADM | 2.57 | NFκB signalling |
| KLF10 | 2.49 | Cell arrest, TGF-b signaling. |
| DEFB4A | -2.34 | Antimicrobial peptide |
| APBA1 | -2.53 | Signalling |
| IGFBP1 | -2.72 | Signalling pathway |
| IL28B | -2.73 | IFN-lambda, antiviral immune defence, |
| IL10 | -3.38 | Anti-inflammatory cytokine |
| NR4A1 | -5.57 | Nuclear receptor, anti-inflammatory, regulator of T cell proliferation. T helper cell differentiation |
| NOD2 | -14.98 | PRR, inflammasome activator, promotes autophagy |
| INOS | -26.88 | Proinflammatory, generator of nitric oxide |

These data appear to show two gene expression signatures—CXCR1/2 ligands (CXCL3, CXCL2, CXCL1, IL-8), which is associated with pro-inflammatory cell migration, and CXCR3 ligands (CXCL9, CXCL10), which is more specifically indicative of IFN-γ-type responses, also supported by IL-32, which is IFN-γ-inducible. These data suggest that the compositions of the invention are useful for stimulating the immune system.

Example 3—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 4—Cytokine Production in Immature Dendritic Cells Induced by MRx0518 Compared to MRx0518+LPS

Summary

This study tested the effect of the bacterial strain MRx0518 alone and in combination with lipopolysaccharide (LPS) on cytokine production in immature dendritic cells.

A monocyte population was isolated from peripheral blood mononuclear cells (PBMCs). The monocyte cells were subsequently differentiated into immature dendritic cells. The immature dendritic cells were plated out at 200,000 cells/well and incubated with MRx0518 at a final concentration of $10^7$/mL, with the optional addition of LPS at a final concentration of 100 ng/mL. The negative control involved incubating the cells with RPMI media alone and positive controls incubated the cells with LPS at a final concentration of 100 ng/mL. The cytokine content of the cells was then analysed.

Results

Figure 4A:
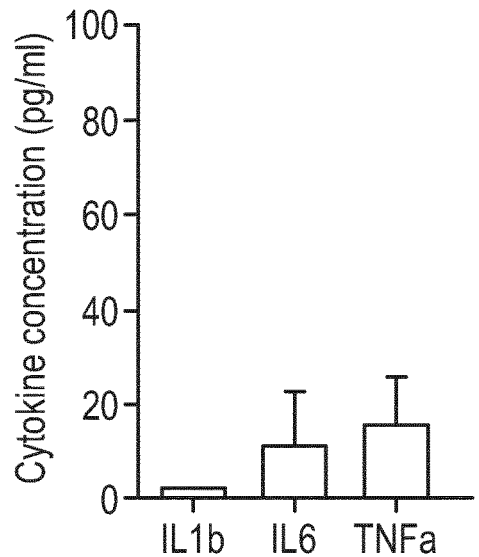
FIG. 4A: Cytokine levels (pg/mLmL) in immature dendritic cells (No bacteria).
Figure 4B:
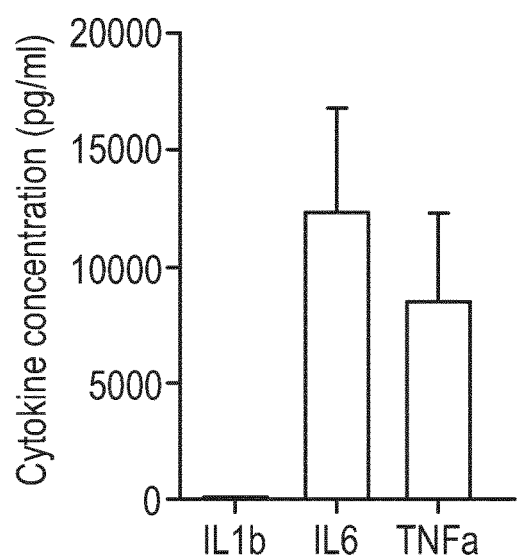
FIG. 4B: Cytokine levels (pg/mLmL) in immature dendritic cells after the addition of LPS.
Figure 4C:
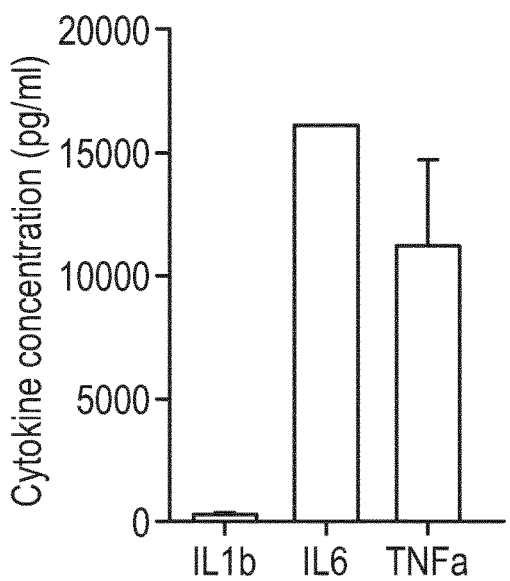
FIG. 4C: Cytokine levels (pg/mLmL) in immature dendritic cells after the addition of MRx0518.
Figure 4D:
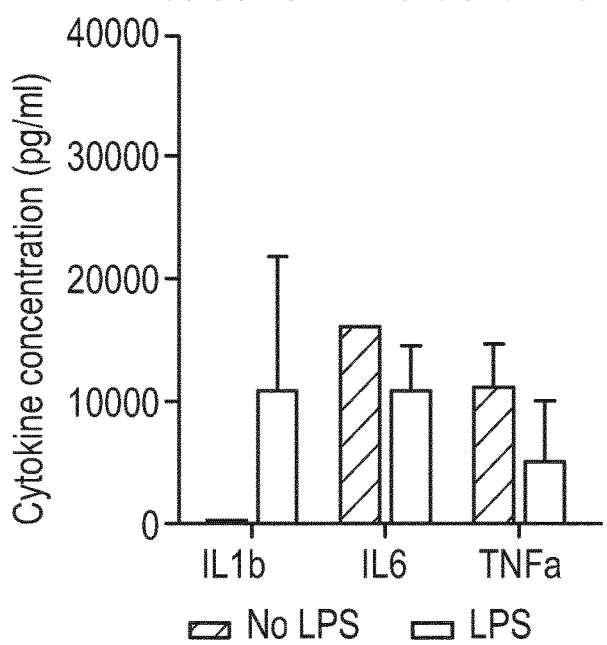
FIG. 4D: Cytokine levels (pg/mLmL) in immature dendritic cells after the addition of MRx0518 and LPS.
Figure 9:
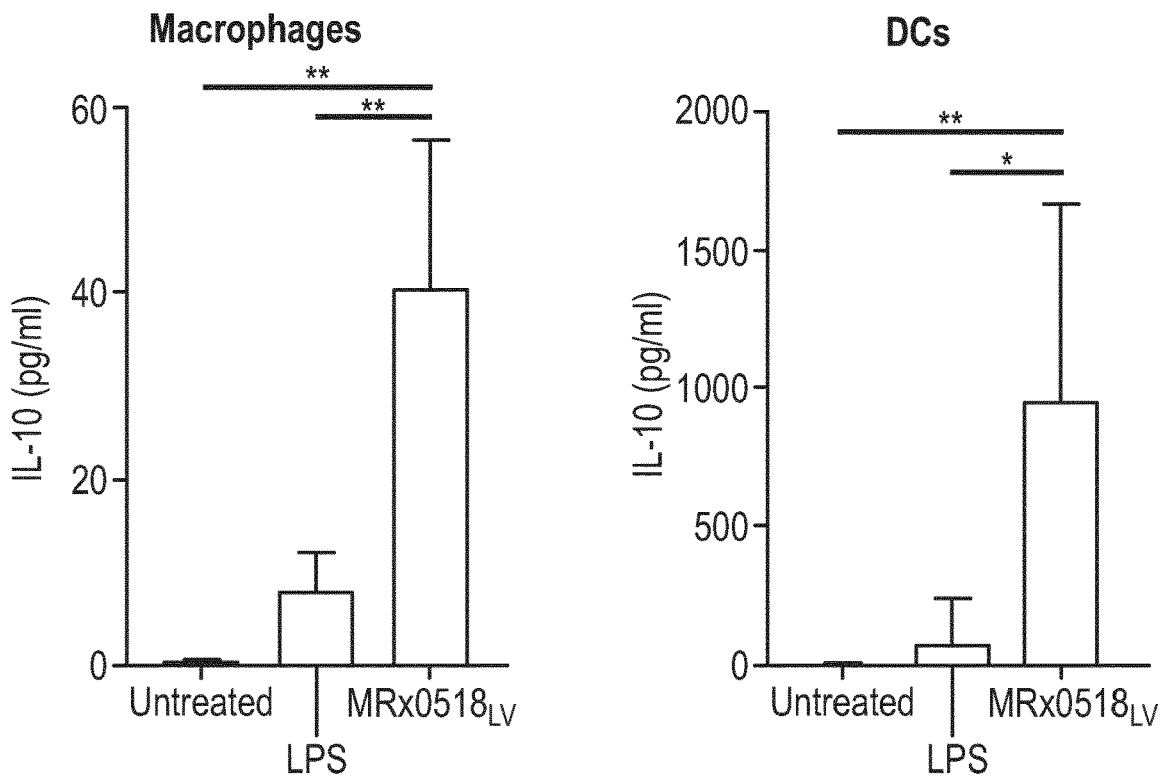
FIG. 9: Immunomodulatory response—IL-10
Figure 10:
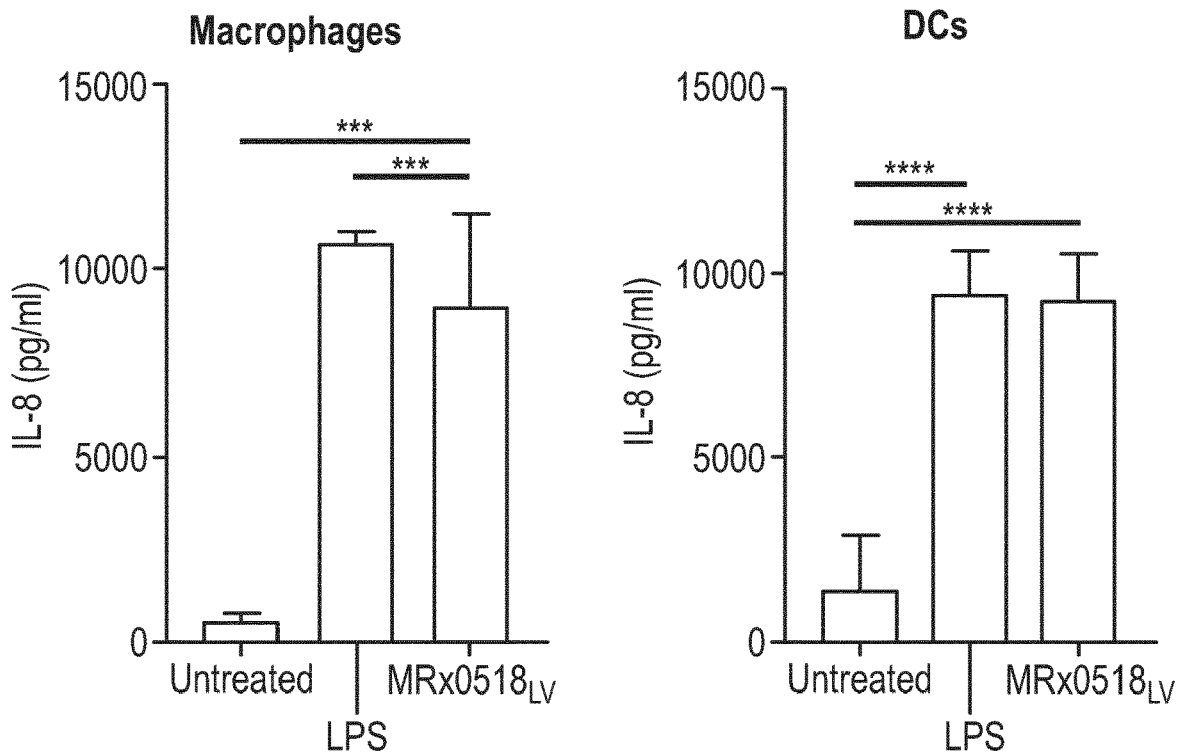
FIG. 10: Immunostimulatory response—IL-8
Figure 11:
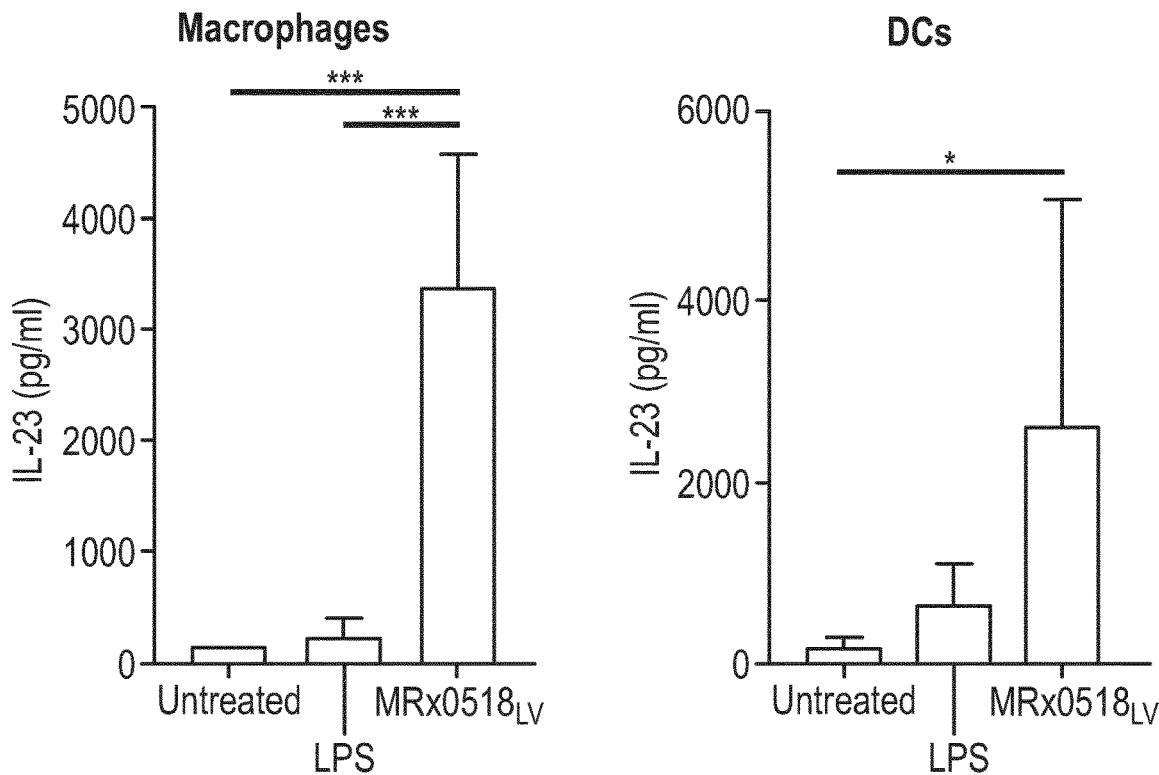
FIG. 11: Immunostimulatory response—IL-23
Figure 12:
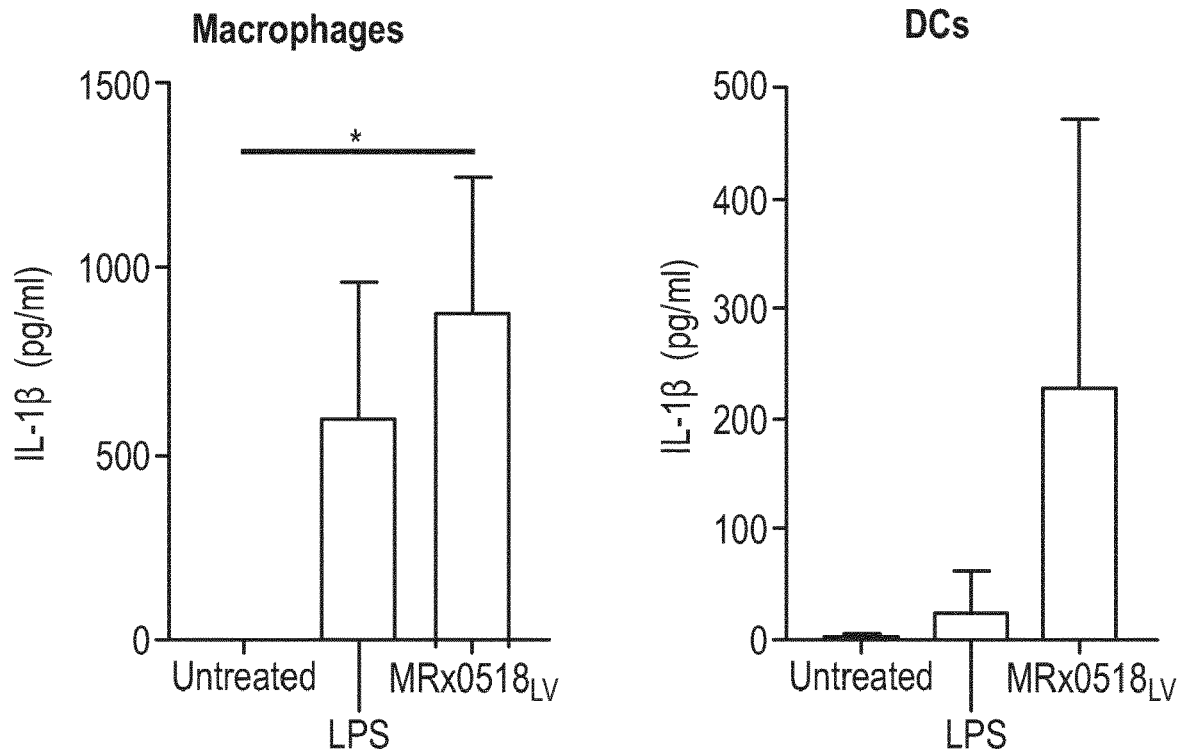
FIG. 12: Immunostimulatory response—IL-1β
Figure 13:
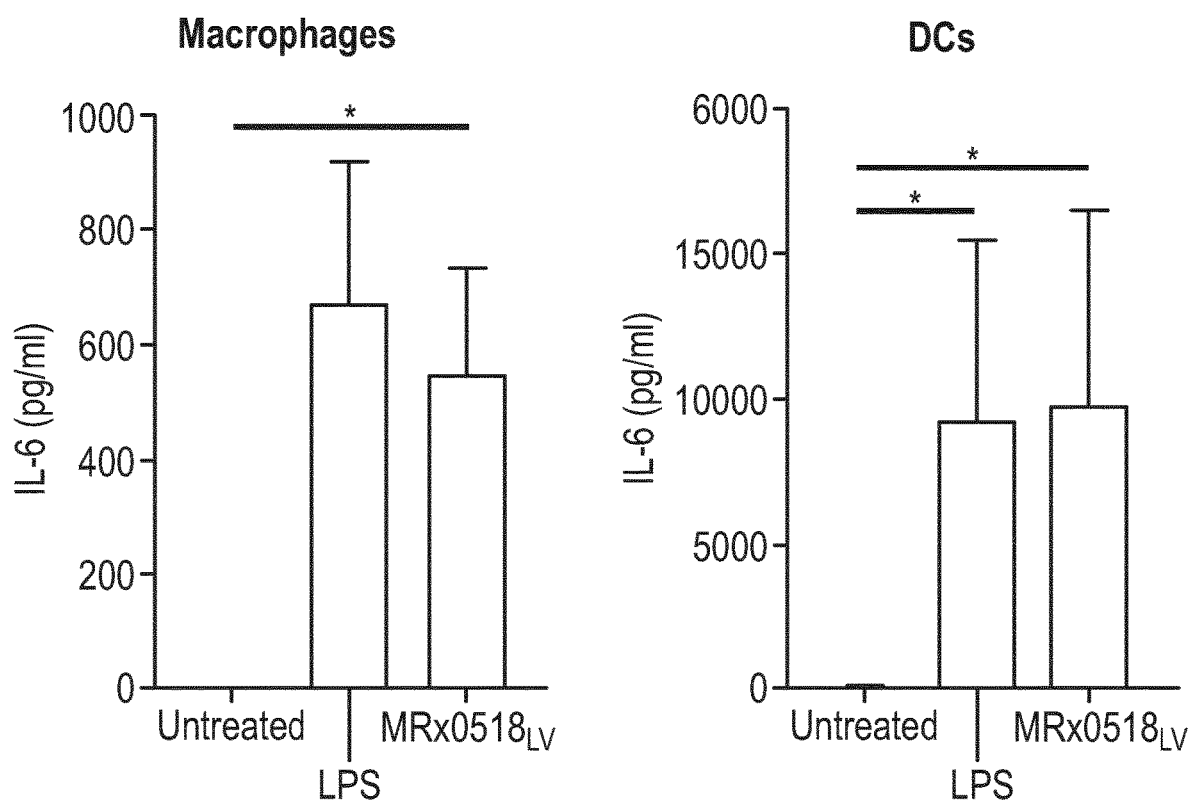
FIG. 13: Immunostimulatory response—IL-6

The results of these experiments can be seen in FIGS. 4a-d. The addition of MRx0518 alone leads to a substantial increase in the level of cytokines IL-6 and TNF-α compared to the negative control (FIGS. 4a and c). The addition of LPS (positive control) leads to an increase in the level of IL-6 and TNF-α compared to the negative control but not IL-1β (FIG. 4b). A combination of MRx0518 and LPS led to a synergistic increase in the level of IL-1β produced (FIG. 4d).

Conclusion

MRx0518 has the ability to induce higher IL-6 and TNF-α cytokine production in immature dendritic cells. The combination LPS and MRx0518 can increase the levels of cytokines IL-1β in immature dendritic cells. These data indicate that MRx0518 alone or in combination with LPS can increase inflammatory cytokines IL-1β, IL-6 and TNF-α, which promotes inflammation.

Example 5—Cytokine Production in THP-1 Cells Induced by MRx0518 Compared to MRx0518+LPS

Summary

This study tested the effect of bacterial strain MRx0518 alone and in combination with LPS on cytokine production in THP-1 cells, a model cell line for monocytes and macrophages.

THF-1 cells were differentiated into MO medium for 48 h with 5 ng/mL phorbol-12-myristate-13-acetate (PMA). These cells were subsequently incubated with MRx0518 at a final concentration of $10^8$/mL, with or without the addition of LPS at a final concentration of 100 ng/mL. The bacteria were then washed off and the cells allowed to incubate under normal growing conditions for 24 h. The cells were then spun down and the resulting supernatant was analysed for cytokine content.

Results

The results of these experiments can be seen in FIGS. 5a-c. The addition of MRx0518 without LPS leads to an increase in the cytokine levels of IL-1β, IL-6 and TNF-α compared to the no bacterial and the bacterial sediment controls. The addition of LPS and MRx0518 leads to a synergistic increase in the production of cytokines.

Conclusion

MRx0518 has the ability to induce cytokine production in THP-1 cells, which can be synergistically increased with the addition of LPS. These data indicate that MRx0518 alone or in combination with LPS can increase inflammatory cytokines IL-1β, IL-6 and TNF-α, which promotes inflammation.

Example 6—Cytokine Analysis

Introduction

The inventors sought to further analyse the immunostimulatory effect of compositions of the invention. The inventors analysed the expression of particular cytokines from THP-1 macrophages and dendritic cells derived from monocytes upon treatment with MRx0518. Macrophages and dendritic cells are key components of the innate immune system, act as messengers between the innate and adaptive immune systems and are resent in the gut where they release a variety of cytokines to modulate the immune response.

Cytokines involved in the innate immune response (TNF-α, IL-12 and IL-10) were analysed and also cytokines involved in the recruitment and activation of adaptive immune cells (IL-8, IL-23, IL-1β and IL-6).

Method

Bacterial Strains

MRx0518

LPS used as positive control

Results

The results are shown in FIGS. 6-13. MRx0518 induces a strong and characteristic immuno-stimulatory profile in THP-1-derived macrophages and DCs derived from monocytes. Cytokines involved in the innate immune response (TNF-α, IL-12 and IL-10) are significantly induced by MRx0518 in both DCs and macrophages. MRx0518 induces a very strong and significant induction of IL-8 in both macrophages and DCs. MRX0581 induces a strong and significant induction of IL-23 and IL-6. MRx0518 also induced IL-1β.

Discussion

These data shows that MRx0518 has immunostimulatory properties, and may be an effective composition for immunostimulation.

Example 7—Mechanism of Action

Figure 14:
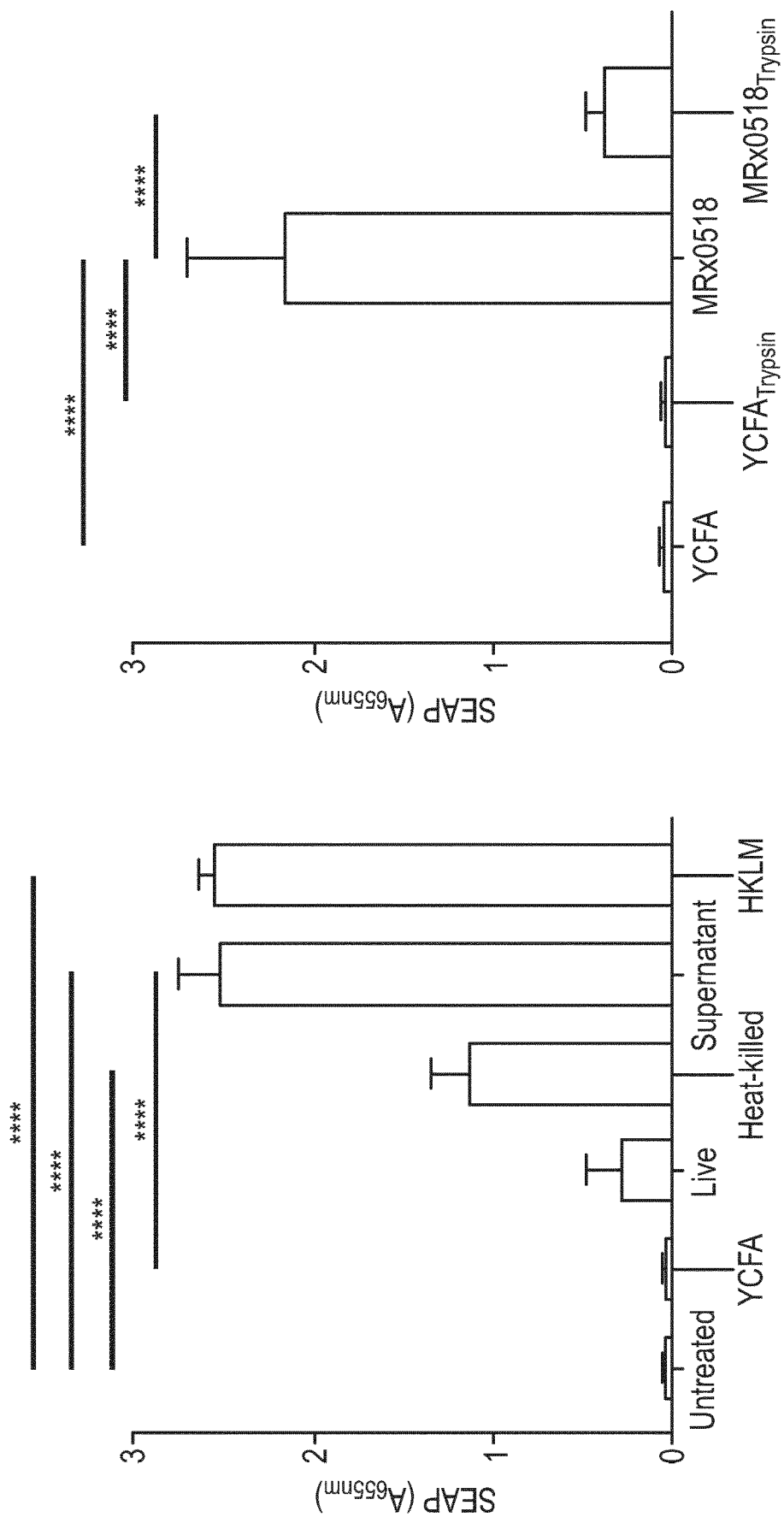
FIG. 14: Mechanism of action—activation of NFκB

Further experiments were performed to characterise the mechanism of action by which MRx0518 stimulates the immune system. A TLR5 signalling reporter assay was selected and the data are presented in FIGS. 14 and 15. MRx0518 supernatant was the most potent activator of TLR5 and NF-κB. Also, the supernatant was treated with various lytic enzymes and trypsin was found to abrogate the majority of activity.

Example 8—Adjuvant Immunostimulatory Activity of MRx0518 in a Therapeutic Combination with a CTLA-4 Inhibitor Summary This study compared the anti-tumour activity of MRx0518, a CTLA-4 inhibitor and therapeutic combinations of MRx0518 with the CTLA-4 inhibitor in mice bearing EMT-6 tumour cells.

Materials

Test and reference substances—Bacterial strain #MRx0518; Anti-CTLA4 antibody (ref: BE0131, Bioxcell; clone: 9H10; reactivity: mouse; isotype: Hamster IgG1; storage conditions: +4° C.).

Test and reference substances vehicles—The MRx0518 bacteria were grown in a bacterial culture medium (Yeast extract, Casitone, Fatty Acid medium (YCFA)) and kept as a glycerol stock at −80° C. The animals were dosed with the bacteria according to the study protocol. The anti-CTLA-4 antibodies were diluted with PBS (ref: BE14-516F, Lonza, France) on each day of injection to mice.

Treatment doses—Bacteria: $2 \times 10^8$ in 200 μL. The anti CTLA4 antibodies were administered at 10 mg/kg body weight according to the most recent body weight of mice.

Routes of administration—The bacterial composition was administered by oral gavage (per os, PO) via a gavage tube at a volume of 200 μL/inj. The anti CTLA-4 antibodies were injected into the peritoneal cavity of mice (Intraperitoneally, IP) at a volume of 10 mL/kg adjusted to the most recent individual body weight of mice.

Cancer cell line and culture conditions—The cell line that was used in this study is the EMT-6 cell line that was obtained from the ATCC (American Type Culture Collection, Manassas, Va., USA). The EMT-6 cell line was established from a transplantable murine mammary carcinoma that arose in a BALB/cCRGL mouse after implantation of a hyperplastic mammary alveolar nodule.

Tumor cells were grown as monolayer at 37° C. in a humidified atmosphere (5% CO2, 95% air). The culture medium was RPMI 1640 containing 2 mM L-glutamine (ref: BE12-702F, Lonza, Verviers, Belgium) supplemented with 10% fetal bovine serum (ref: 3302, Lonza). EMT-6 tumor cells are adherent to plastic flasks. For experimental use, tumor cells were detached from the culture flask by a 5-minute treatment with trypsin-versene (ref: BE02-007E, Lonza), in Hanks' medium without calcium or magnesium (ref: BE10-543F, Lonza) and neutralized by addition of complete culture medium. The cells were counted and their viability was assessed by 0.25% trypan blue exclusion assay.

Use of animals—Healthy female BALB/C (BALB/cByJ) mice, 5-7 weeks old, were obtained from CHARLES RIVER (L'Arbresles) and maintained in SPF health status according to the FELASA guidelines. Animal housing and experimental procedures were realized according to the French and European Regulations and NRC Guide for the Care and Use of Laboratory Animals. Animals were maintained 3-4 per cage in housing rooms under controlled environmental conditions: Temperature: 22±2° C., Humidity 55±10%, Photoperiod (12 h light/12 h dark), HEPA filtered air, 15 air exchanges per hour with no recirculation. Animal enclosures were provided with sterile and adequate space with bedding material, food and water, environmental and social enrichment (group housing) as described: Top filter polycarbonate Eurostandard Type III or IV cages, Corn cob bedding (ref: LAB COB 12, SERLAB, France), 25 kGy Irradiated diet (Ssniff® Soest, Germany), Complete food for immunocompetent rodents—R/M-H Extrudate, Sterile, filtrated at 0.2 μm water and Environmental enrichment (SIZZLE-dri kraft-D20004 SERLAB, France). Animals are individually identified with RFID transponder and each cage was ladled with a specific code. Treatment of the animals started after one week of acclimation for batches 2 and 3, or after three weeks of acclimation for batch 1.

Experimental Design and Treatments

On day −14 (D-14), non-engrafted mice were randomized according to their individual body weight into 3 groups of 30 animals and 2 groups of 10 animals using Vivo Manager® software (Biosystemes, Couternon, France). The mice were separated into 3 batches of 10 animals per treatment group (batch 1: 10 animals of groups 1, 2 and 3; batch 2: 10 animals of groups 1, 2 and 3 and batch 3: 10 animals of groups 1 to 5) with different termination points from the start of the study: D-14 or D0.

Figure 16A:
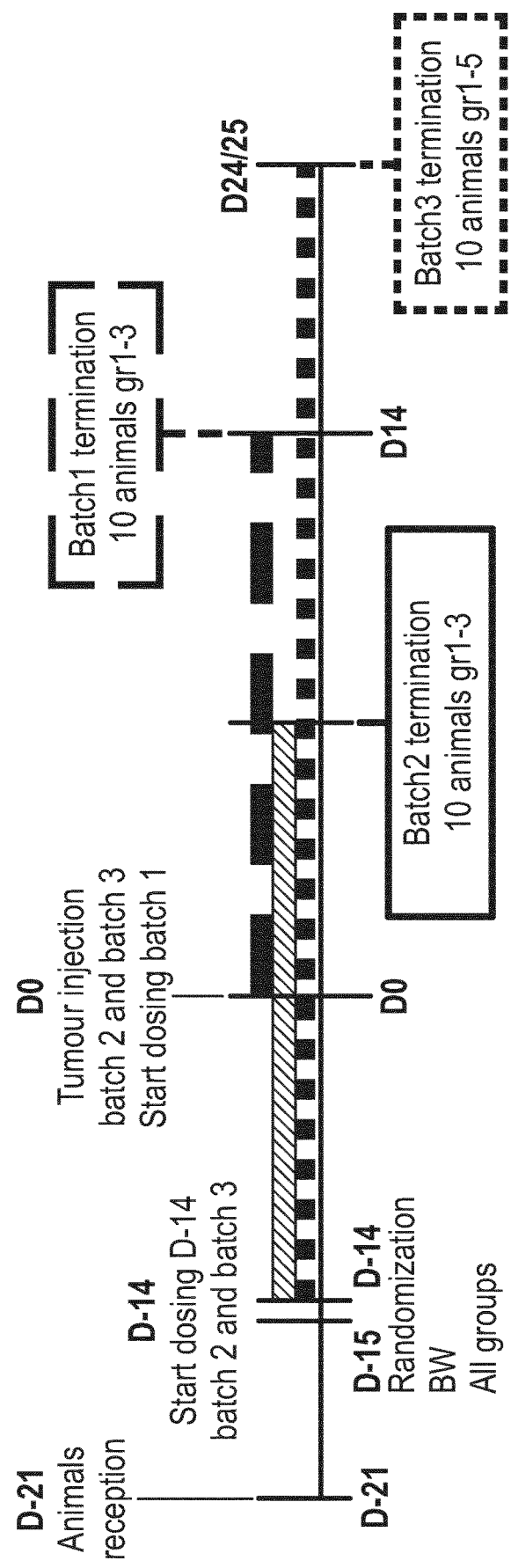
FIG. 16A: A schematic representation of the treatment schedule of the different groups used in Example 8 described herein below.

At termination, batch 3 was split into 2 cohorts, due to termination and FACS analyses schedules; these were staggered over 1 day: D24/D25. Therefore, every cohort of animals had 5 animals per treatment group (4 animals from cage one and one animal from cage 2). Based on the ethical criteria, if the tumor volume were higher than 1500 mm³, the selection of the animals to be sacrifice on D24 and D25 is based on tumor volume instead of the cage. The experimental design is depicted in FIG. 16A and summarized below:

1) Batch 1 (groups 1, 2 and 3) started treatment on D0 and was culled at D14 (10 animals form groups 1 to 3). These did not receive tumor cells and constituted the baseline group.

2) Batch 2 (group 1, 2 and 3) started treatment on D-14 and was culled at D7 (10 animals form groups 1 to 3).

3) Batch 3 (groups 1 to 5) started treatment on D-14 and was culled at D24/25 (10 animals form groups 1 to 5). The treatment of Anti CTLA-4 started on D10.

On day 0 (D0) all mice of batches 2 and 3 (termination at day 7 and 24/25, respectively) were engrafted with EMT-6 tumour cells by a subcutaneous injection of $1 \times 10^6$ EMT-6 cells in 200 μL RPMI 1640 into the right flank (the 30 mice from batch 1, that were sacrificed on D14, did not receive the tumour injection). The mice were treated according to the following treatment schedule groups (TW×2=twice a week):

| Group | No. Animals | Treatment | Dose | Route | Treatment Schedule |
|---|---|---|---|---|---|
| 1 | 30 = 10 batch 1 10 batch 2 10 batch 3 | Untreated (+ Tumour) | — | — | — |
| 2 | 30 = 10 batch 1 10 batch 2 10 batch 3 | Vehicle (YCFA) | — | PO | Daily-14 to D0 Daily-14 to D7 Daily-14 to D24/25 |
| 3 | 30 = 10 batch 1 10 batch 2 10 batch 3 | MRx0518 | $2 \times 10^8$ | PO | Daily-14 to D0 Daily-14 to D7 Daily-14 to D24/25 |
| 4 | 10 batch 3 | Anti-CTLA-4 + YCFA | 10 mg/kg | IP + PO | TWx2 from D10 YCFA Daily-14 to D24/25 |
| 5 | 10 batch 3 | Anti-CTLA-4 + MRx0518 | 10 mg/kg + $2 \times 10^8$ bacteria | IP + PO | TWx2 from D10 Bacteria Daily-14 to D24/25 |

Animal Monitoring

The viability and behaviour of the animals was recorded every day. Body weights were measured twice a week. The length and width of the tumour was measured twice a week with callipers and the volume of the tumour was estimated by the following formula:

$$\text{Tumour volume} = \frac{\text{Width}^2 \times \text{Length}}{2}$$

Figure 16B:
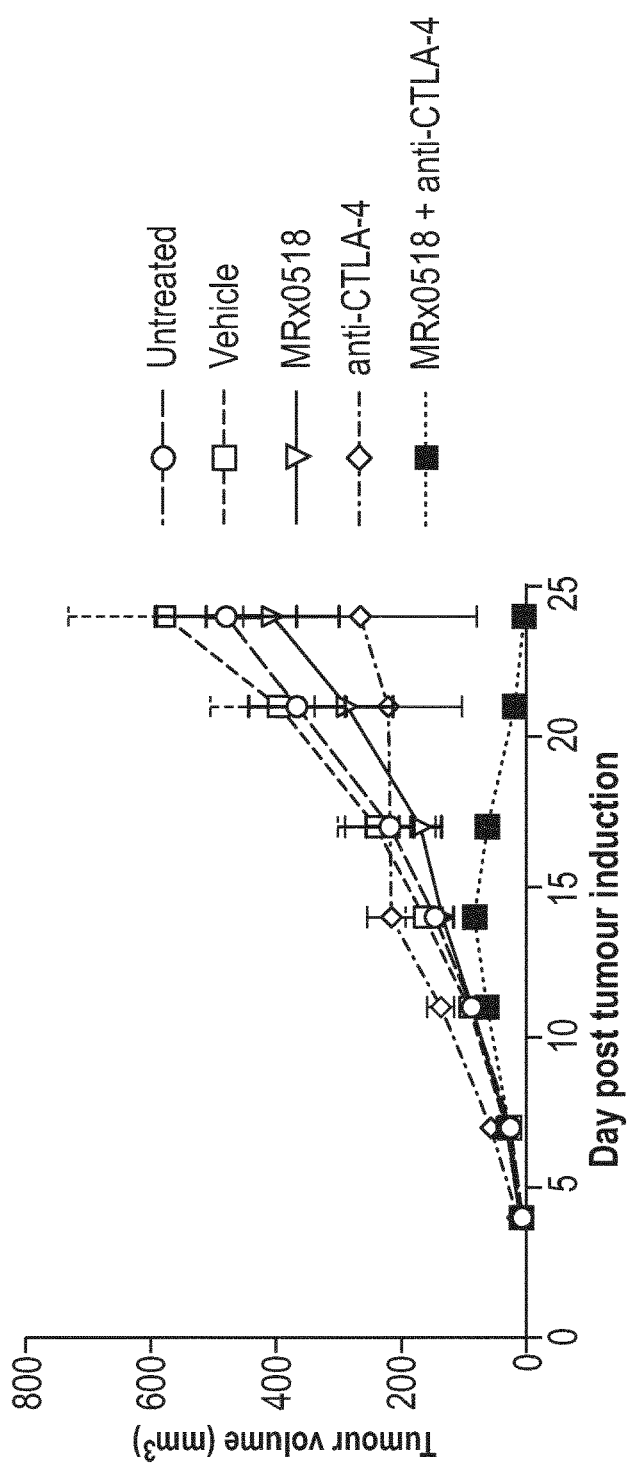
FIG. 16B: Mean tumour volume in mice bearing a tumour formed by EMT-6 cells. The mice were either untreated or treated with a YCFA vehicle (Vehicle), MRx0518 bacteria in YCFA medium (MRx0518), an anti-CTLA-4 antibody and YCFA medium (Anti-CTLA-4) or a combination of MRx0518 and the anti-CTLA-4 antibody. The provided table indicates the statistical significance between each two treatments at each time point.

The treatment efficacy was assessed in terms of the effects of the test substance on the tumour volumes of treated animals relative to control animals. The following evaluation criteria of antitumor efficacy were determined using Vivo Manager® software (Biosystemes, Couternon, France). Mean tumour volumes of groups 1 to 5 are depicted in FIG. 16B. Throughout the course of the study, a progression in tumour growth was observed in all groups, with the exception of the MRx0518+Anti-CTLA-4-treated group where a regression of tumour growth occurred from Day 14 post tumour induction. MRx0518+Anti-CTLA-4 treatment significantly reduced tumour growth compared to the Vehicle-treated group on Day 21 and Day 24 post tumour induction. The combination treatment of MRx0518 with Anti-CTLA-4 was the most efficacious for reducing tumour growth in BALB/c mice bearing subcutaneously grafted EMT6 tumours. These data demonstrate that MRx0518 has an immunostimulatory effect.

Example 9—Efficacy of Bacterial Inocula in Mouse Models of Cancer

Summary

This study tested the efficacy of compositions comprising bacterial strain according to the invention in a tumor model.
Materials
    Test substance—Bacterial strain #MRx0554.
    Reference substance—Anti-CTLA-4 antibody (clone: 9H10, catalog: BE0131, isotype: Syrian Hamster IgG1, Bioxcell).
    Test and reference substances vehicles—Bacterial culture medium (Yeast extract, Casitone, Fatty Acid medium (YCFA)). Each day of injection to mice, antibody was diluted with PBS (ref: BE14-516F, Lonza, France).
    Treatment doses—Bacteria: $2 \times 10^8$ in 200 µL YCFA. The anti-CTLA-4 was injected at 10 mg/kg/inj. Anti-CTLA-4 was administered at a dose volume of 10 mL/kg/adm (i.e. for one mouse weighing 20 g, 200 µL of test substance will be administered) according to the most recent body weight of mice.
    Routes of administration—Bacterial inoculum was administered by oral gavage (per os, PO) via a cannula. Cannulas were decontaminated every day. Anti-CTLA-4 was injected into the peritoneal cavity of mice (Intraperitoneally, IP).
    Culture conditions of bacterial strain—The culture conditions for the bacterial strain were as follows:
        Pipette 10 mL of YCFA (from the prepared 10 mL E&O lab bottles) into Hungate tubes
        Seal the tubes and flush with CO2 using a syringe input and exhaust system
        Autoclave the Hungate tubes
        When cooled, inoculate the Hungate tubes with 1 mL of the glycerol stocks
        Place the tubes in a static 37° C. incubator for about 16 hours.
        The following day, take 1 mL of this subculture and inoculate 10 mL of YCFA (pre-warmed flushed Hungate tubes again, all in duplicate)
        Place them in a static 37° C. incubator for 5 to 6 h
Cancer Cell Line and Culture Conditions—
    The cell lines that were used are detailed in the table below:

| Cell line | Type | Mouse strain | Origin |
| --- | --- | --- | --- |
| EMT-6 | Breast carcinoma | BALB/c | ATCC |

The EMT-6 cell line was established from a transplantable murine mammary carcinoma that arose in a BALB/cCRGL mouse after implantation of a hyperplastic mammary alveolar nodule [71].

Cell culture conditions—All cell lines were grown as monolayer at 37° C. in a humidified atmosphere (5% $CO_2$, 95% air). The culture medium and supplement are indicated in the table below:

| Cell line | Culture medium | Supplement |
| --- | --- | --- |
| EMT6 | RPMI 1640 containing 2 mM L-glutamine (ref: BE12-702F, Lonza) | 10% fetal bovine serum (ref: #3302, Lonza) |

For experimental use, adherent tumor cells were detached from the culture flask by a 5 minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability will be assessed by 0.25% trypan blue exclusion assay.
Use of Animals—
    Healthy female BALB/C (BALB/cByJ) mice, of matching weight and age, were obtained from CHARLES RIVER (L'Arbresles) for the EMT6 model experiments.
    Animals were maintained in SPF health status according to the FELASA guidelines, and animal housing and experimental procedures according to the French and European Regulations and NRC Guide for the Care and Use of Laboratory Animals were followed [72,73]. Animals were maintained in housing rooms under controlled environmental conditions: Temperature: 22±2° C., Humidity 55±10%, Photoperiod (12 h light/12 h dark), HEPA filtered air, 15 air exchanges per hour with no recirculation. Animal enclosures were provided with sterile and adequate space with bedding material, food and water, environmental and social enrichment (group housing) as described: 900 $cm^2$ cages (ref: green, Tecniplast) in ventilated racks, Epicea bedding (SAFE), 10 kGy Irradiated diet (A04-10, SAFE), Complete food for immuno-competent rodents—R/M-H Extrudate, water from water bottles.

Experimental Design and Treatments

Antitumor Activity, EMT6 Model
    Treatment schedule—The start of first dosing was considered as D0. On D0, non-engrafted mice were randomized according to their individual body weight into groups of 8-9 using Vivo Manager® software (Biosystemes, Couternon, France). On D0, the mice received vehicle (culture medium) or bacterial strain. On D14, all mice were engrafted with EMT-6 tumor cells as described below. On D24, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 8 | Untreated | — | — | — |
| 2 | 8 | Vehicle (media) | — | PO | 38 days EMT6 |
| 3 | 8 | MRx0554 | 2 × 10$^8$ bacteria | PO | 38 days EMT6 |
| 4 | 8 | Anti-CTLA4 | 10 mg/kg | IP | TWx2, D10, D13, D17 and D20 for EMT6 |

The monitoring of animals was performed as described below.

Induction of EMT6 tumours in animals—On D14, tumors were induced by subcutaneous injection of 1×10$^6$ EMT-6 cells in 200 µL RPMI 1640 into the right flank of mice.

Euthanasia—Each mouse was euthanized when it reached a humane endpoint as described below, or after a maximum of 6 weeks post start of dosing.

Animal Monitoring

Clinical monitoring—The length and width of the tumor was measured twice a week with callipers and the volume of the tumor was estimated by this formula [74]:

$$\text{Tumor volume} = \frac{\text{width}^2 \times \text{length}}{2}$$

Humane endpoints [75]: Signs of pain, suffering or distress: pain posture, pain face mask, behaviour; Tumor exceeding 10% of normal body weight, but non-exceeding 2000 mm$^3$; Tumors interfering with ambulation or nutrition; Ulcerated tumor or tissue erosion; 20% body weight loss remaining for 3 consecutive days; Poor body condition, emaciation, cachexia, dehydration; Prolonged absence of voluntary responses to external stimuli; Rapid laboured breathing, anaemia, significant bleeding; Neurologic signs: circling, convulsion, paralysis; Sustained decrease in body temperature; Abdominal distension.

Anaesthesia—Isoflurane gas anesthesia was used for all procedures: surgery or tumor inoculation, i.v. injections, blood collection. Ketamine and Xylazine anesthesia was used for stereotaxia surgical procedure.

Analgesia—Carprofen or multimodal carprofen/buprenorphine analgesia protocol were adapted to the severity of surgical procedure. Non-pharmacological care was provided for all painful procedures. Additionally, pharmacological care not interfering with studies (topic treatment) were provided at the recommendation of the attending veterinarian.

Euthanasia—Euthanasia of animals was performed by gas anesthesia over-dosage (Isoflurane) followed by cervical dislocation or exsanguination.

Results

Antitumor Activity, EMT6 Model

The results are shown in FIG. 17. Treatment with the bacterial strain of the invention led to a clear reduction in tumour volume relative to both the negative controls. The positive control also led to a reduction in tumour volume, as would be expected.

These data indicate that strain MRx0554 may be useful for treating or preventing other diseases associated with reduced immune system activity.

Example 10—Analysis of Carbohydrate Metabolism—API 50 CHL Analysis of MRx0554

The Analytical Profile Index (API) test system consists of strips which contain miniaturised biochemical tests which assay for enzymatic activity in bacterial species. These tests are routinely used in the characterisation of novel strains. API 50 CHL testing was carried out to examine carbohydrate metabolism in MRx0554. As per manufacturer's instructions, bacteria were cultured in 10 mL YCFA broth for 16-18 hours at 37° C. in an anaerobic workstation. This culture was diluted in 10 mL API CHL Medium so as to achieve a density roughly equivalent to McFarland standard No. 2, and 110 µl of this mixture was used to inoculate each cupule on a set of API 50 CH test strips. Test strips were incubated in a humidified incubation box at 37° C. in an anaerobic workstation for 48 hours, following which the colour of each cupule was recorded and assigned a value of negative, intermediate positive, positive or doubtful.

Figure 18:
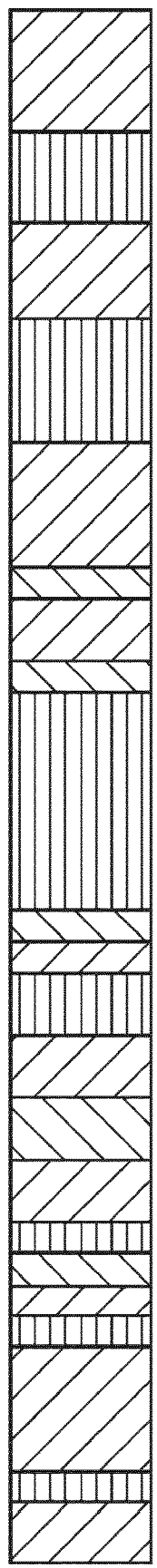
FIG. 18: API 50 CHL profile of MRx0554.

Using API 50 CHL analysis, MRx0554 tested positive for fermentation of L-arabinose, D-ribose, D-xylose, D-galactose, D-glucose, D-fructose, D-mannose, N-acetylglucosamine, amygdalin, arbutin, esculin, salicin, D-cellobiose, D-maltose, D-saccharose (sucrose), D-trehalose, gentiobiose, D-tagatose, and potassium gluconate (FIG. 18). Intermediate reactions were observed for D-mannitol, methyl α-D-glucopyranoside, D-lactose, D-raffinose, amidon (starch), and D-turanose.

Example 11—TLR9 Activation

To further elucidate the mechanism by which MRx0518 stimulates the immune system, HEK-Blue™ human TLR9 reporter cells (InvivoGen, San Diego, Calif., USA) were used to test the effect of MRx0518 on TLR9 activation.

Maintenance of Cell Lines and Bacterial Strains

HEK-Blue™ human TLR9 reporter cells (InvivoGen, San Diego, Calif., USA) were grown in DMEM supplemented with 10% (v/v) foetal bovine serum (FBS), 4 mM L-glutamine, 4.5 mg/mL glucose, 100 U/mL penicillin, 100 µg/mL streptomycin, 100 µg/mL Normocin™ (InvivoGen), 10 µg/mL blastocidin (InvivoGen) and 100 µg/mL zeocin (InvivoGen) to 90% density. Cells were maintained at 37° C. and 5% CO2. For assays, cells were washed once with phosphate-buffered saline (PBS) (Sigma-Aldrich, Gillingham, England, UK) and resuspended in antibiotic-free growth media at a density of 450,000 cells/mL. All reagents were supplied by Sigma Aldrich unless otherwise stated. *E. gallinarum* MRx0518 was routinely cultured in Yeast extract, Casitone, Fatty Acid media (YCFA, E&O Laboratories, Bonnybridge, Scotland, UK) at 37° C. in an anaerobic cabinet (Don Whitley Scientific, Shipley, England, UK).

TLR9 Reporter Assays

The following compositions were examined for their ability to induce TLR9 activation:

1. Live fraction of MRx0518 (MRx0518LV)—Late log phase bacterial cultures were centrifuged at 5,000×g for 5 min at room temperature to generate bacterial fractions. Pelleted bacteria were washed once in PBS and re-suspended in antibiotic-free cell culture media to the appropriate dilution.
2. MRx0518 supernatant fraction (MRx05185N)—Culture supernatants were harvested and filtered through a 0.22 μm pore size filter and diluted in water.
3. Heat-killed fraction of MRx0518 (MRx0518HK)—Bacterial cultures were heat-inactivated for 40 min at 80° C. and prepared as described above for the live fraction. MRx0518LV and MRx0518HK were used at a multiplicity of infection (MOI) of 100:1. A 100:1 MOI equivalent volume was used for MRx0518SN. The synthetic CpG oligonucleotide ODN2006 (InvivoGen) was used as an assay positive control at a concentration of 5 μM. YCFA was used as a negative control. Viable cells counts were determined by plating.

HEK-Blue™ human TLR9 reporter cells were incubated with the above treatments for 22 hours at 37° C. in a 5% $CO_2$ atmosphere. Assays were developed using QUANTI-Blue™ (InvivoGen) as per manufacturer's recommendations for 2 h. The results depicted in FIG. 19 are an average from at least three independent experiments. Statistical significance was determined using the ordinary one-way ANOVA and Tukey's multiple comparisons tests.

The results demonstrate that the living and supernatant fractions were able to activate TLR9.

Example 12—T Cell Differentiation

The ability of MRx0518 to induce T-cell differentiation was explored in vitro on peripheral blood mononuclear cells (PBMCs, Stemcell, Cat:70025). Briefly, PBMCs were plated in 96-well plates plated with anti-CD3 (Ebioscience, anti-CD3 monoclonal antibody (OKT3 clone), functional grade, cat. No. 16-0037-81) at 400,000/well in 50 μl cRPMI medium per well (cRPMI contains RPMI 1640 (+L-Glut, 21875-034) 2 mM final conc. Stock 200 mM.; 10% HI FBS (Gibco life technologies, 10082-147); 50 μm mercaptoethanol (Gibco life technologies, 21985-023); and 1% pen/strep (P4333, 10 mg/mL). Heat-killed MRx0518 (prepared by incubation at 80° C. for 30 minutes, after which the cultures were washed with PBS and resuspended in appropriate cell culture medium and viable counts were confirmed by plating) was then added to each well, 4,000,000 in 100 μl/well.

Following 3 days in a 37° C. incubator, the cells were removed and re-suspended in a medium containing PMA-(Sigma, Cat no. P8139), Ionomycin (Sigma, Cat no. 13909) and GolgiSTOP (BD, Cat no 554724) for 5 hours. PMA stock was 1 mg/mL in DMSO which was further diluted in 100 ug/mL (each sample required 50 ng/mL in cRPMI), Ionomycin stock was 1 mM in DMSO (1 μM in cRPMI was used) and GolgiStop concentration was used at 4 μl/6 mL. Supernatants were passed through a 0.22 μm filter and diluted appropriately in co-culture medium.

The cells were then subjected to a flow cytometry staining:

After washing, the cells were incubated with viability dye (Viobility 405/520 Fixable Dye from Miltenyi biotec 1 μl/sample)+human Fc block, cat. 564219 (1 μl/sample) in PBS for 10 mins in the dark at room temperature. The surface antibodies (2 μl of each) were then added directly to the wells for 10 mins in the dark at room temperature—CD3-APC-Vio 770 (Miltenyi, cat. No. 130-113-136), CD4-VioBlue (Miltenyi, cat. No. 130-114-534) and CD25-Vio-Bright FITC (Miltenyi, cat. No. 130-113-283). The cells were then washed twice in PBS and spun down at 300 g/5 min/RT.

The eBioscience FoxP3 transcription factor staining buffer was then used to fix and permeabilise the cells (cat. No. 00-5523). Following the eBioscience protocol, a perm/fix buffer was prepared using 1 part of concentrate solution and 3 parts of diluent. The cells were fixed for 1 h at RT and then washed 2× in 1×Perm wash and spun down at 300 g/5 min/RT. The following intracellular staining or transcription factor antibodies were added to the samples in perm wash (1×) for 45 min/in the dark/at room temperature or in the fridge overnight (up to 18 h), followed by washing the antibodies 2× using Perm wash (300 μl) and re-suspension in PBS (250 μl) to acquire on the cytometer:

| Intracellular markers | Transcription factors |
|---|---|
| 2 ul anti-IL10-PE | 5.5 ul anti-FoxP3-PE-Cy7 |
| 2 ul anti-IFNγ-PE Vio770 | 5 ul anti-Tbet-APC |
| 10 ul anti-IL17a-APC | 9 ul anti-RoRyt-PE |

Anti IFNγ-PE Vio770 human antibodies (Miltenyi, cat. No. 130-114-025)
Anti IL10-PE human antibodies (Miltenyi, cat. No. 130-112-728)
Anti IL17a-APC human antibodies (Miltenyi, cat. No. 130-099-202)
Anti RORyt-PE human antibodies (Miltenyi, cat. No. 130-103-837)
Anti Tbet-APC human antibodies (Miltenyi, cat. No. 130-098-655
Anti-Foxp3 monoclonal antibody (236A/E7), PE-Cy7 (ebioscience) cat. No. 25-4777-41

As can be seen in FIG. 20A-B, both supernatant of MRx0518 (SP 518) and heat-killed MRx0518 (HK 518) were able to induce differentiation of T helper cells and cytotoxic T cells, respectively, even in the absence of cytokines to induce differentiation (no cyto)

Example 13—MRx0518 Induced Cytokine Signature

Figure 21A:
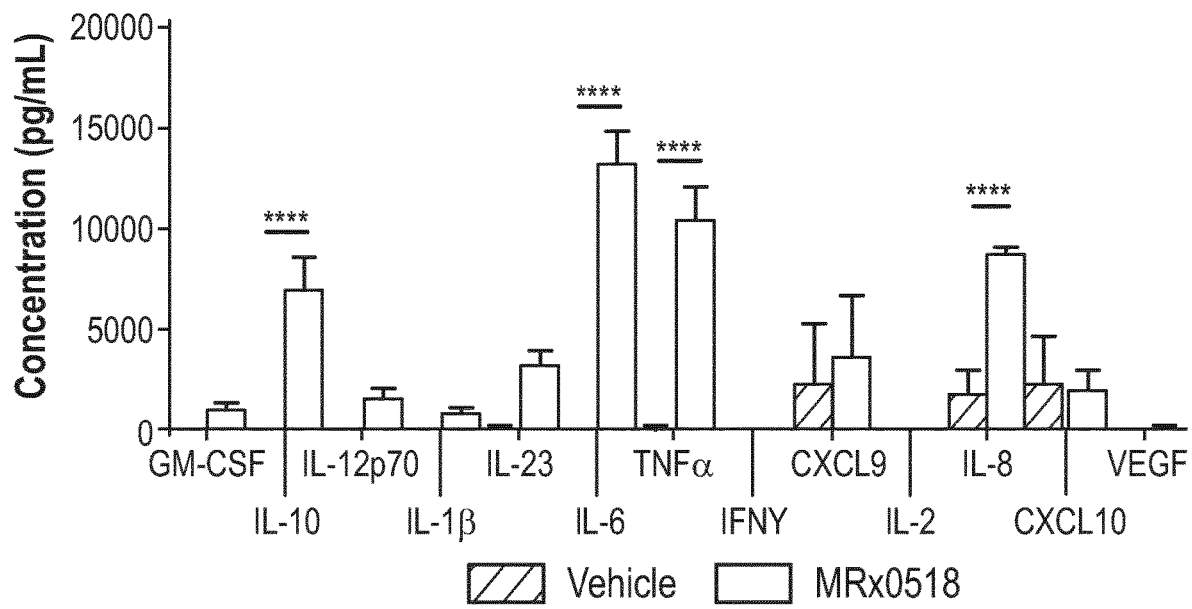
FIGS. 21A-21D: In-vitro cytokine production by (FIG. 21A) PBMC cells.
Figure 21B:
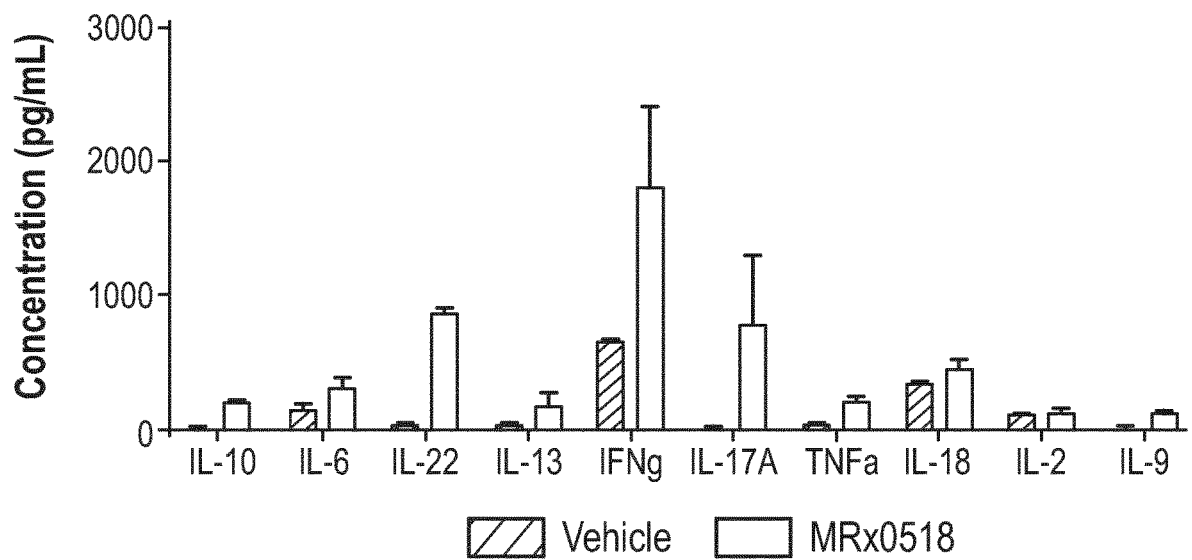
Figure 21C:
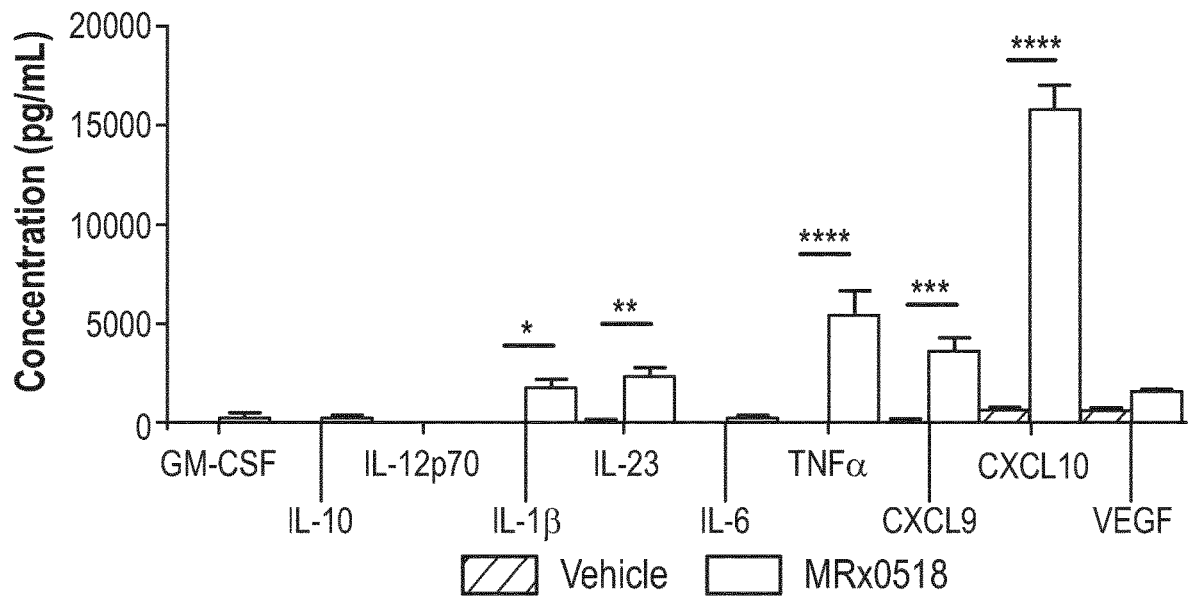
Figure 21D:
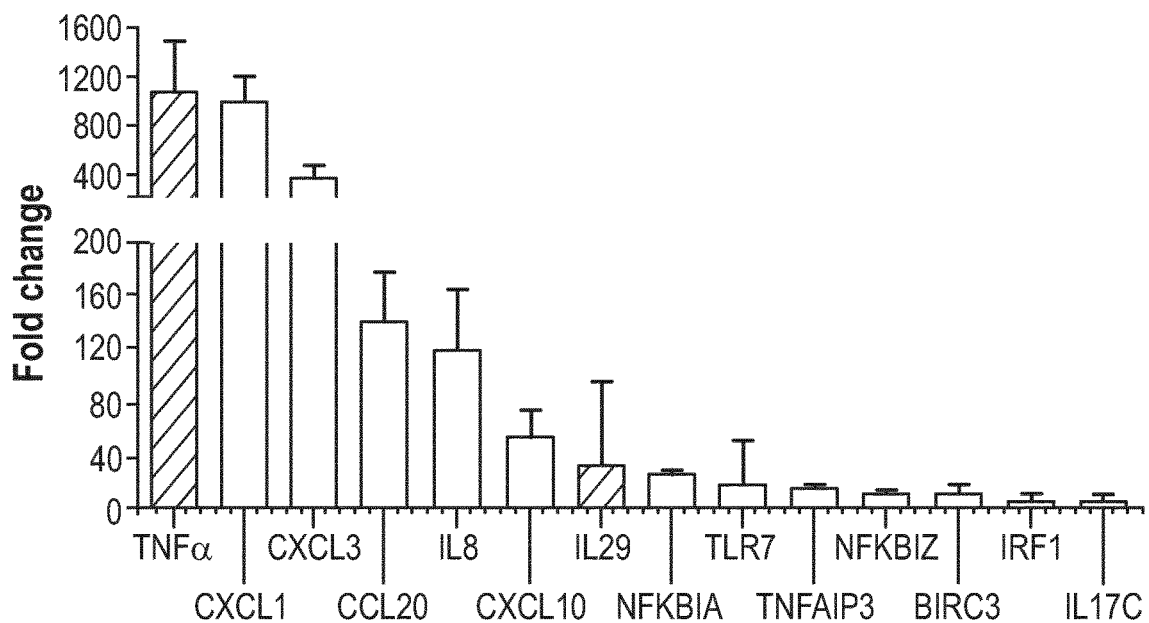
Figure 21E:
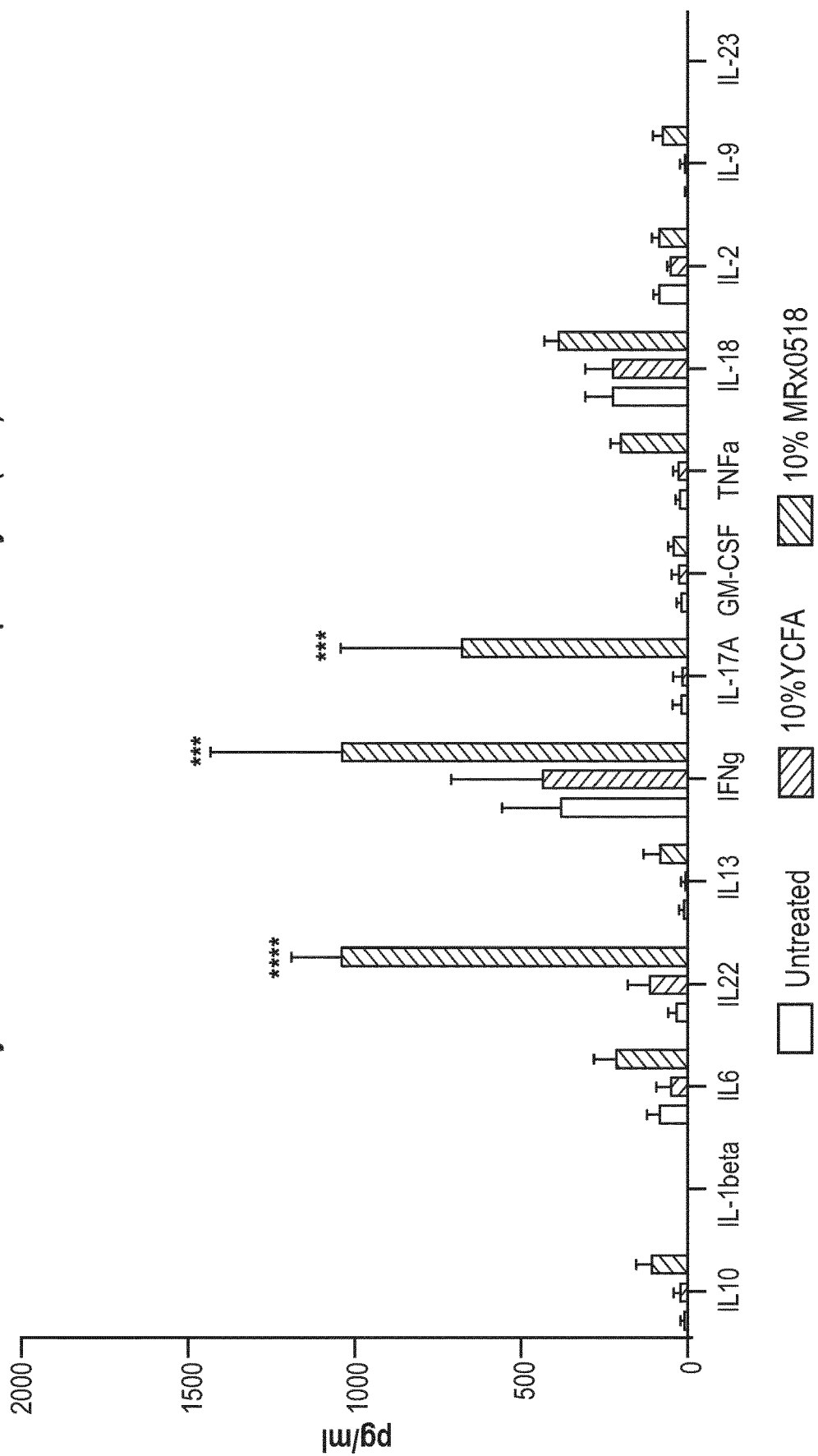
FIG. 21E: In-vitro cytokine production by splenocytes (N=3), from cells that were either untreated ("Untreated"), treated with YCFA blank media ("10% YCFA") or treated with MRx0518 cell-free bacterial supernatant ("10% MRx0518").
Figure 21F:
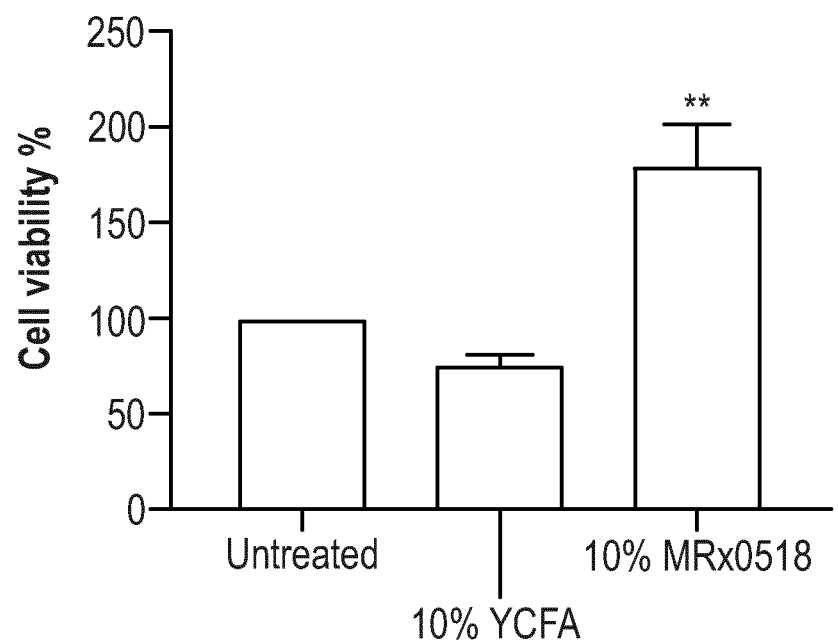
FIG. 21F: Viability of splenocytes extracted from mice (N=4) as measure by an MTT assay. Cells were either untreated ("Untreated"), treated with YCFA blank media ("10% YCFA") or treated with MRx0518 cell-free bacterial supernatant ("10% MRx0518").
Figure 22A:
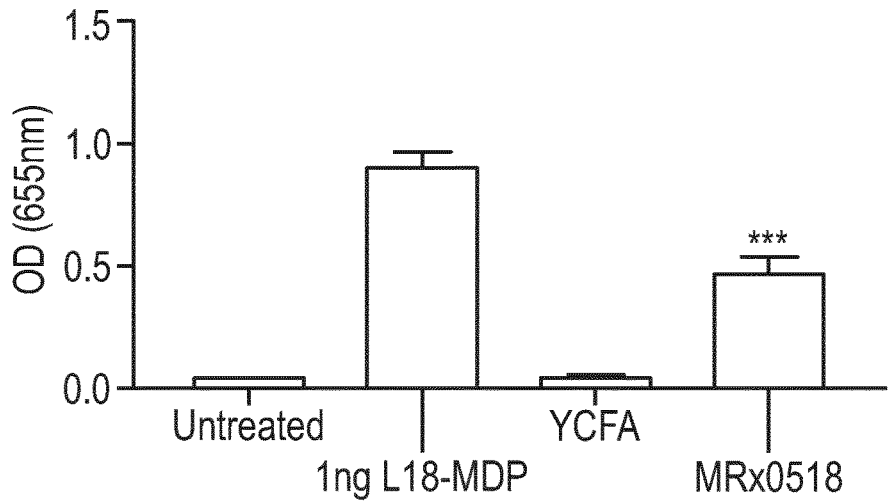
FIGS. 22A-22D: NF-κB promoter activation in (FIG. 22A) HEK-Blue™-hNOD2 cells.
Figure 22B:
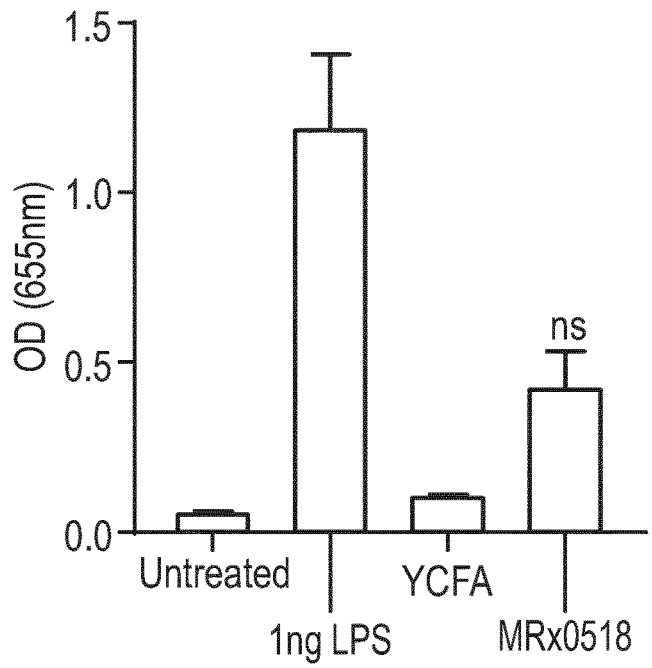
Figure 22C:
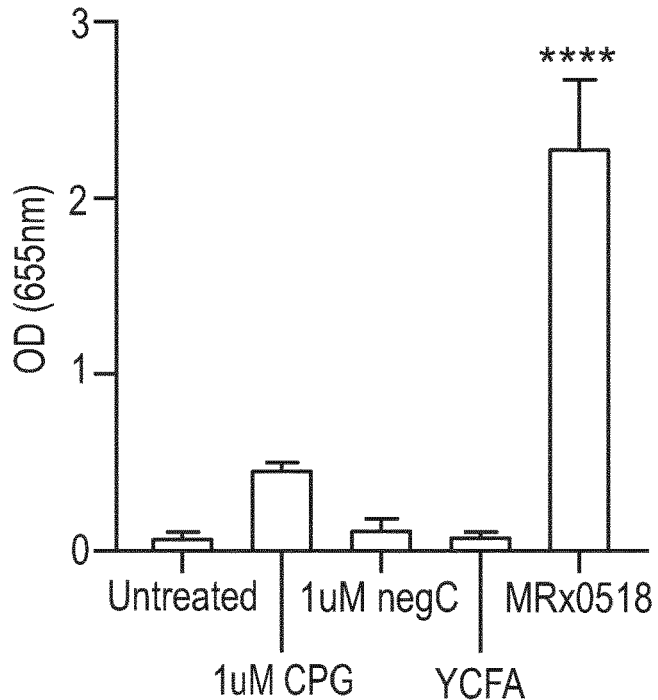
Figure 22D:
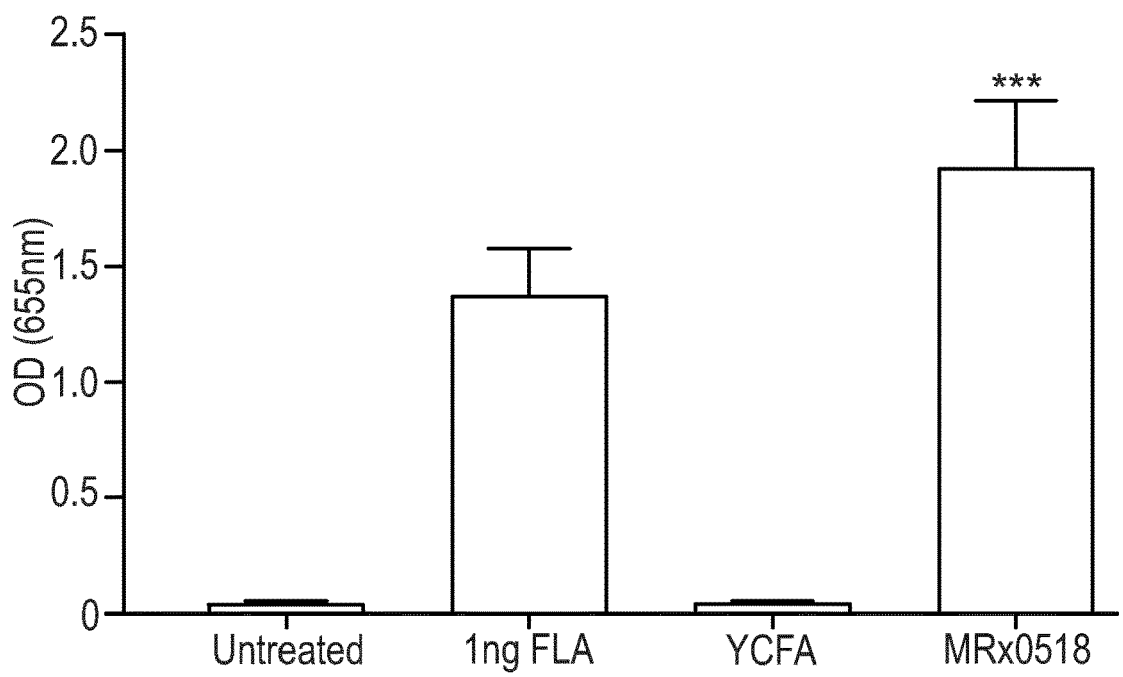

Splenocytes were isolated from C57BL/6 mice and plated in 96 well plates at a density of 900,000 cells/well in RPMI1640 supplemented with 10% FBS, 2 mM L-glutamine, 100 U/mL Pen/Strep (Sigma-Aldrich) and 55 μM β-mercaptoethanol (Gibco). Cells were treated with different concentrations of blank media (YCFA⁺) or bacteria supernatant from stationary phase for 72 hrs. Cell free supernatants were collected after each time point and stored at −80° C. for cytokine analysis. Cytokines were measured using multiplex procartaplex MO Th1/Th2/Th9/Th17/Th22/Treg 17plex kit (Invitrogen). Cell proliferation of untreated splenocytes or splenocytes treated by 10% YCFA medium or 10% MRx0518 bacteria supernatant was measured using MTT assay (Millipore), as depicted in FIG. 21F.

Live, growing MRx0518 bacteria were incubated for up to 2 h with the human intestinal epithelial cell line CaCo-2 and with the human monocyte/macrophage cell line THP-1. The host response was analysed immediately (CaCo-2) or after a further 24 h incubation (THP-1).

Frozen healthy human PBMCs were purchased from Stem Cells Technologies (Cambridge UK). The cells were thawed and left to rest overnight in full growth media (RPMI 1640 with 10% FBS, 55 μM β-mercaptoethanol, 2 mM L. Glutamine and 100 U/mL penicillin, 100 μg/mL streptomycin) in $CO_2$ incubator at 37° C. For the experiment, cells were plated at a density of 750,000 cells/well in 48 well plates and treated in full growth media with 10% bacteria supernatants in the presence or absence of 1 ng/mL LPS. Cell culture media was added to untreated wells. Cells were left to rest for 72 h, thereafter cell free supernatants were collected and spun down for 3 minutes at 10,000 g at 4° C. Samples were stored at −80° C. for cytokine analysis. Cytokine quantification was conducted using a ProcartaPlex multiplex immunoassay following the manufacturers recommendations (Thermo Fischer Scientific). Briefly, 50 µl of cell-free co-culture supernatants were used for cytokine quantification using a MAGPIX® MILLIPLEX® system (Merck) with the xPONENT software (Luminex, Austin, Tex., USA). Data was analysed using the MILLIPLEX® analyst software (Merck) using a 5-parameter logistic curve and background subtraction to convert mean fluorescence intensity to pg/mL values.

Data are expressed in FIGS. 21A-D as an average of two technical replicates of 10 biological replicates (PBMC) or three biological replicates (splenocytes) and show production of cytokines in (A) PBMCs; (B) Splenocytes; (C) THP-1 cells; and (D) Caco-2 cells, following treatment with YCFA blank media ("Vehicle") or MRx0518 bacteria/MRx0518 cell-free bacterial supernatant ("MRx0518"). FIG. 21E depicts additional data relating to cytokine secretion from splenocytes (N=3), from cells that were either untreated ("Untreated"), treated with YCFA blank media ("10% YCFA") or treated with MRx0518 cell-free bacterial supernatant ("10% MRx0518").

As can be seen in FIGS. 21A-D, treatment of different cells with a supernatant of MRx0518 bacteria resulted in immunostimulation as evident by an increase in cytokine production.

Example 14—NF-κB Activation

The activation of the NF-κB promoter was tested in HEK293 cells co-expressing an NF-κB inducible secreted embryonic alkaline phosphatase (SEAP) reporter gene with either the human NOD2 gene, TLR4, TLR9 or TLR5 genes (HEK-Blue™-hNOD2, HEK-Blue™-hTLR5, HEK-Blue™-hTLR9 and FMK-Blue™-hTLR4 cells, respectively, by InvivoGen, San Diego, Calif., USA).

Briefly, HEK-TLR4 cells were maintained in DMEM 4.5 g/L D-glucose supplemented with 10% (v/v) heat-inactivated FBS, 4 mM L-Glutamine, 100 U/ml penicillin, 100 mg/ml streptomycin, 100 mg/ml normocin, 1×HEK-Blue selection media; for HEK-TLR5 and HEK-TLR9 same media was used with the exception of the use of 2 mM L-Glutamine. HEK-TLR5 and HEK-TLR9 were selected using 30 mg/ml and 10 mg/ml blasticidin respectively and 100 µg/ml zeocin media for both cell lines into the culture.

For the experiment, cells were washed with PBS, dissociated in PBS and collected in growth media. Cells were plated in 96-well plates at a density of 25,000 cells/well for HEK-TLR4 and HEK-TLR5, 80,000 cells/well for HEK-TLR9 and 50,000 cells/well for HEK-NOD2.

To evaluate the responsiveness of the cells to their ligands, the cells were treated with 1 ng/ml LPS (HEK-TLR4), 1 ng/µµl ultra-pure flagellin from *Salmonella typhimurium* (HEK-TLR5), 1 µM ODN2006 CPG (HEK-TLR9 positive control) or 1 µM ODN2006 GPC (HEK-TLR9 negative control), 1 ng/ml of L18-MDP and incubated in a $CO_2$ incubator at 37° C. Treatments proceeded for 22 h at 37° C. and 5% $CO_2$, after which the detection of Secreted embryonic alkaline phosphatase (SEAP) activity from cell culture supernatant was performed using QUANTI-blue solution according to manufacturer's instructions. Briefly, 20 µl of cell culture media was collected and analysed for the presence of SEAP by mixing with 200 µl of QUANTI-Blue detection media. After 2 h (HEK-TLR4 and HEK-TLR5) or 4 h (HEK-TLR9 and HEK-NOD2) incubation at 37° C., optical density was measured at 655 nm on a microplate reader (iMark microplate, Bio-Rad).

As can be seen in FIGS. 22A-D (showing results from averaged technical replicates for three independent experiments), NF-κB promoter activation was measured in cells which were either untreated ("Untreated"), treated with YCFA+ medium ("YCFA") or treated with MRx0518 ("MRx0518"). The following positive controls (ing) were used—L18-MDP (for HEK-Blue™-hNOD2 cells, FIG. 22A), Lipopolysaccharide, LPS (for HEK-Blue™-hTLR4, FIG. 22B), CPG or negC (for HEK-Blue™-hTLR9, FIG. 22C) or recombinant flagellin from *S. typhimurium*, FLA (for HEK-Blue™-hTLR5, FIG. 22D). The cells were incubated with the various treatment at 37° C. in a 5% $CO_2$ atmosphere for 22 h. To measure NF-κB promoter activation (N=3), QUANTI-Blue™ (InvivoGen) was mixed with cell supernatants, the plates were incubated for 2 h and optical density was measured at 655 nm.

Sequences

```
(Enterococcus gallinarum 16S rRNA gene-AF039900)
                                                            SEQ ID NO: 1
  1 taatacatgc aagtcgaacg cttttctttt caccggagct tgctccaccg aaagaaaaag 61 agtggcgaac gggtgagtaa cacgtgggta acctgcccat cagaagggga taacacttgg 121 aaacaggtgc taataccgta taacactatt ttccgcatgg aagaaagttg aaaggcgctt 181 ttgcgtcact gatggatgga cccgcggtgc attagctagt tggtgaggta acggctcacc 241 aaggccacga tgcatagccg acctgagagg gtgatcggcc acactgggac tgagacacgg 301 cccagactcc tacgggaggc agcagtaggg aatcttcggc aatggacgaa agtctgaccg 361 agcaacgccg cgtgagtgaa gaaggttttc ggatcgtaaa actctgttgt tagagaagaa 421 caaggatgag agtagaacgt tcatcccttg acggtatcta accagaaagc cacggctaac 481 tacgtgccag cagccgcggt aatacgtagg tggcaagcgt tgtccggatt tattgggcgt 541 aaagcgagcg caggcggttt cttaagtctg atgtgaaagc ccccggctca accggggagg 601 gtcattggaa actgggagac ttgagtgcag aagaggagag tggaattcca tgtgtagcgg
```

-continued

```
 661 tgaaatgcgt agatatatgg aggaacacca gtggcgaagg cggctctctg gtctgtaact
 721 gacgctgagg ctcgaaagcg tggggagcga acaggattag atacctggt agtccacgcc
 781 gtaaacgatg agtgctaagt gttggagggt ttccgccctt cagtgctgca gcaaacgcat
 841 taagcactcc gcctggggag tacgaccgca aggttgaaac tcaaaggaat tgacggggc
 901 ccgcacaagc ggtggagcat gtggtttaat tcgaagcaac gcgaagaacc ttaccaggtc
 961 ttgacatcct tgaccactc tagagataga gcttccccctt cggggcaaa gtgacaggtg
1021 gtgcatggtt gtcgtcagct cgtgtcgtga gatgttgggt taagtcccgc aacgagcgca
1081 acccttattg ttagttgcca tcatttagtt gggcactcta gcgagactgc cggtgacaaa
1141 ccggaggaag gtggggatga cgtcaaatca tcatgcccct tatgacctgg gctacacacg
1201 tgctacaatg gaagtacaa cgagttgcga agtcgcgagg ctaagctaat ctcttaaagc
1261 ttctctcagt tcggattgta ggctgcaact cgcctacatg aagccggaat cgctagtaat
1321 cgcggatcag cacgccgcgg tgaatacgtt cccgggcctt gtacacaccg cccgtcacac
1381 cacgagagtt tgtaacaccc gaagtcggtg aggtaacctt tttggagcca gccgcctaag
1441 gtgggataga tgattggggt gaagtcgtaa caaggtagcc gtatcggaag gtgcggctgg
1501 atcacc
```

(consensus 16S rRNA sequence for *Enterococcus gallinarum* strain MRx0518)

SEQ ID NO: 2

TGCTATACATGCAGTCGAACGCTTTTTCTTTCACCGGAGCTTGCTCCACCGAAAGAAAAAGAGTGGCGAACGGGTGAGTA
ACACGTGGGTAACCTGCCCATCAGAAGGGGATAACACTTGGAAACAGGTGCTAATACCGTATAACACTATTTTCCGCATG
GAAGAAAGTTGAAAGGCGCTTTTGCGTCACTGATGGATGGACCCGCGGTGCATTAGCTAGTTGGTGAGGTAACGGCTCAC
CAAGGCCACGATGCATAGCCGACCTGAGAGGGTGATCGGCCACACTGGGACTGAGACACGGCCCAGACTCCTACGGGAGG
CAGCAGTAGGGAATCTTCGGCAATGGACGAAAGTCTGACCGAGCAACGCCGCGTGAGTGAAGAAGGTTTTCGGATCGTAA
AACTCTGTTGTTAGAGAAGAACAAGGATGAGAGTAGAACGTTCATCCCTTGACGGTATCTAACCAGAAAGCCACGGCTAA
CTACGTGCCAGCAGCCGCGGTAATACGTAGGTGGCAAGCGTTGTCCGGATTTATTGGGCGTAAAGCGAGCGCAGGCGGTT
TCTTAAGTCTGATGTGAAAGCCCCCGGCTCAACCGGGGAGGGTCATTGGAAACTGGGAGACTTGAGTGCAGAAGAGGAGA
GTGGAATTCCATGTGTAGCGGTGAAATGCGTAGATATATGGAGGAACACCAGTGGCGAAGGCGGCTCTCTGGTCTGTAAC
TGACGCTGAGGCTCGAAAGCGTGGGGAGCGAACAGGATTAGATACCCTGGTAGTCCACGCCGTAAACGATGAGTGCTAAG
TGTTGGAGGGTTTCCGCCCTTCAGTGCTGCAGCAAACGCATTAAGCACTCCGCCTGGGGAGTACGACCGCAAGGTTGAAA
CTCAAAGGAATTGACGGGGCCCGCACAAGCGGTGGAGCATGTGGTTTAATTCGAAGCAACGCGAAGAACCTTACCAGGT
CTTGACATCCTTTGACCACTCTAGAGATAGAGCTTCCCCTTCGGGGGCAAAGTGACAGGTGGTGCATGGTTGTCGTCAGC
TCGTGTCGTGAGATGTTGGGTTAAGTCCCGCAACGAGCGCAACCCTTATTGTTAGTTGCCATCATTTAGTTGGGCACTCT
AGCGAGACTGCCGGTGACAAACCGGAGGAAGGTGGGGATGACGTCAAATCATCATGCCCCTTATGACCTGGGCTACACAC
GTGCTACAATGGGAAGTACAACGAGTTGCGAAGTCGCGAGGCTAAGCTAATCTCTTAAAGCTTCTCTCAGTTCGGATTGT
AGGCTGCAACTCGCCTACATGAAGCCGGAATCGCTAGTAATCGCGGATCAGCACGCCGCGGTGAATACGTTCCCGGGCCT
TGTACACACCGCCCGTCACACCACGAGAGTTTGTAACACCCGAAGTCGGTGAGGTAACCTTTTTGGAGCCAGCCGCCTAA
GGTG (16S rRNA gene for *Enterococcus gallinarum* strain MRx0554)

SEQ ID NO: 3

```
  1 taatacatgc aagtcgaacg cttttctttt caccggagct tgctccaccg aaagaaaaag
 61 agtggcgaac gggtgagtaa cacgtgggta acctgcccat cagaagggga taacacttgg
121 aaacaggtgc taataccgta taacactatt ttccgcatgg aagaaagttg aaaggcgctt
181 ttgcgtcact gatggatgga cccgcggtgc attagctagt tggtgaggta acggctcacc
```

-continued

```
 241 aaggccacga tgcatagccg acctgagagg gtgatcggcc acactgggac tgagacacgg 301 cccagactcc tacgggaggc agcagtaggg aatcttcggc aatggacgaa agtctgaccg 361 agcaacgccg cgtgagtgaa gaaggttttc ggatcgtaaa actctgttgt tagagaagaa 421 caaggatgag agtagaacgt tcatcccttg acggtatcta accagaaagc cacggctaac 481 tacgtgccag cagccgcggt aatacgtagg tggcaagcgt tgtccggatt tattgggcgt 541 aaagcgagcg caggcggttt cttaagtctg atgtgaaagc ccccggctca accggggagg 601 gtcattggaa actgggagac ttgagtgcag aagaggagag tggaattcca tgtgtagcgg 661 tgaaatgcgt agatatatgg aggaacacca gtggcgaagg cggctctctg gtctgtaact 721 gacgctgagg ctcgaaagcg tggggagcga acaggattag ataccctggt agtccacgcc 781 gtaaacgatg agtgctaagt gttggagggt ttccgccctt cagtgctgca gcaaacgcat 841 taagcactcc gcctggggag tacgaccgca aggttgaaac tcaaaggaat tgacggggc 901 ccgcacaagc ggtggagcat gtggtttaat tcgaagcaac gcgaagaacc ttaccaggtc 961 ttgacatcct ttgaccactc tagagataga gcttcccctt cggggggcaaa gtgacaggtg 1021 gtgcatggtt gtcgtcagct cgtgtcgtga gatgttgggt taagtcccgc aacgagcgca 1081 acccttattg ttagttgcca tcatttagtt gggcactcta gcgagactgc cggtgacaaa 1141 ccggaggaag gtggggatga cgtcaaatca tcatgcccct tatgacctgg gctacacacg 1201 tgctacaatg gaagtacaa cgagttgcga agtcgcgagg ctaagctaat ctcttaaagc 1261 ttctctcagt tcggattgta ggctgcaact cgcctacatg aagccggaat cgctagtaat 1321 cgcggatcag cacgccgcgg tgaatacgtt cccgggcctt gtacacaccg cccgtcacac 1381 cacgagagtt tgtaacaccc gaagtcggtg aggtaacctt tttggagcca gccgcctaag 1441 gtgggataga tgattggggt gaagtcgtaa caaggtagcc gtatcggaag gtgcggctgg 1501 atcacc
```

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12):1021-35
[4] Mazmanian et al. (2005) *Cell* 15; 122(1):107-18.
[5] Frank et al. (2007) *PNAS* 104(34):13780-5.
[6] Machiels et al. (2013) *Gut.* 63(8):1275-83.
[7] WO 2013/050792
[8] WO 2014/167338
[9] Goldin and Gorbach (2008) *Clin Infect Dis.* 46 Suppl 2:S96-100.
[10] Azad et al. (2013) *BMJ* 347:f6471.
[11] Collins et al. (1984) *Int J Syst Evol Microbiol.* 34: 220-223.
[12] Masco et al. (2003) *Systematic and Applied Microbiology,* 26:557-563.
[13] Srůtková et al. (2011) *J. Microbiol. Methods,* 87(1):10-6.
[14] Masco et al. (2003) *Systematic and Applied Microbiology,* 26:557-563.
[15] Srůtková et al. (2011) *J Microbiol. Methods,* 87(1):10-6.
[16] Ren and Torres (2009) *Brain Res Rev.;*60(1):57-64
[17] Martinon et al. (2002) *Mol Cell.;*10(2):417-26.
[18] Murphy et al. (2003) *J Exp Med.* 2003; 198(12): 1951-1957.
[19] Chan et al. (2006) *J Exp Med.;* 203(12): 2577-2587.
[20] *The Immune Response Basic and Clinical Principles,* 1st Edition (2006)
[21] Gaur and Aggarwal (2003). *Biochem Pharmacol.;*66 (8):1403-8.
[22] Wang and Lin (2008) *Acta Pharmacol Sin.;* 29(11): 1275-1288.
[23] Tanaka et al. (2014) *Cold Spring Harb Perspect Biol.;* 6(10): a016295.
[24] Bettelli et al. (2006) *Nature* 441:235-238
[25] Kawai and Akira (2007) *Trends in Molecular Medicine* 13, 11, 460-469
[26] Bloch et al. (2016) *Eur Cytokine Netw.;*27(3):63-67
[27] Weinberger (2018) *Curr Opin Pharmacol,* 41, 34-41.
[28] Lim (2015) *Aging Cell* 14, 907-915
[29] Mohanty et al. (2015) *J Infect Dis,* 211(7) 1174-1184.
[30] Fernandez-Ruiz et al., (2015) *Vaccine* 2015 33(51)
[31] Morel et al., (2011) *Vaccine,* 29(13) 2461-2473.
[32] Leal et al., (2001) *Immunol* 103(3) 375-381
[33] Knudsen et al. (2016), *Sci Reps,* 6 (19570).
[34] Su et al., (2008) *Vaccine* 26(40), 5111-22
[35] Li et al, (2007) *J Immunol,* 178(8), 5271-5276
[36] Coffman et al., (2012) *Immunity* 33(4) 492-503
[37] Olafsdottir et al., *Vaccine* 33(40) 5302-5307
[38] Didierlaurent et al., *J Immunol* 2014, 193(4) 1920-1930
[39] Park et al., (2002) *J Immunol,* 169(3), 1433-1443
[40] Berthoud et al. (2009) *J Immunol Methods* 340(1) 33-41
[41] Mori et al. (2012), *Eur J Immunol* 42, 2709-2719
[42] Fraietta, et al. (2018) *Nat Med.* 24(5):563-571
[43] Zhou, et al. (2010) *Blood* 116(14):2484-93.
[44] Glenn and Whartenby (2014) *World J Stem Cells.;* 6(5): 526-539.

[45] Heng et al. (2004) *Cardiovasc Res.* 2004 Apr. 1; 62(1):34-42.
[46] Rashidi et al. (2018) *Biol Blood Marrow Transplant* 24, 1260-1263
[47] Fulop et al (2013) *Crit Rev Oncog.* 2013; 18(6):489-513.
[48] Bektas et al. (2017) *J Leukoc Biol.;*102(4):977-988.
[49] Fulop et al (2016) *Rev Invest Clin.;*68(2):84-91.
[50] Fulop et al. (2018) *Front Immunol.;* 8:1960.
[51] Miyamoto-Shinohara et al. (2008) *J. Gen. Appl. Microbiol.,* 54, 9-24.
[52] Leslie et al. (1995) *Appl. Environ. Microbiol.* 61, 3592-3597.
[53] Mitropoulou et al. (2013) *J Nufr Metab.* (2013) 716861.
[54] Kailasapathy et al. (2002) *Curr Issues Intest Microbiol.* 3(2):39-48.
[55] Handbook of Pharmaceutical Excipients, 2nd Edition, (1994), Edited by A Wade and P J Weller
[56] Remington's Pharmaceutical Sciences, Mack Publishing Co. (A. R. Gennaro edit. 1985)
[57] *Handbook of Microbiological Media, Fourth Edition* (2010) Ronald Atlas, CRC Press.
[58] Strobel (2009) *Methods Mol Biol.* 581:247-61.
[59] Gennaro (2000) *Remington: The Science and Practice of Pharmacy.* 20th edition, ISBN: 0683306472.
[60] *Molecular Biology Techniques: An Intensive Laboratory Course,* (Ream et al., eds., 1998, Academic Press).
[61] *PCR (Introduction to Biotechniques Series),* 2nd ed. (Newton & Graham eds., 1997, Springer Verlag)
[62] *Current Protocols in Molecular Biology* (F. M. Ausubel et al., eds., 1987) Supplement 30
[63] Smith & Waterman (1981) *Adv. Appl. Math.* 2: 482-489
[64] Rockwell et al., (1972) *J Natl Cancer Inst.* 49:735-49.
[65] Bertram and Janik (1980) *Cancer Lett.* 11:63-73.
[66] Darlington (1987) *Meth Enzymol.* 151:19-38.
[67] Principe d'éthique de l'expérimentation animate, Directive n° 2010/63 CEE 22 Sep. 2010, Décrêt n° 2013-118 1 Feb. 2013.
[68] Guide for the Care and Use of Laboratory Animals. Eighth Edition. The National Academies Press; 2011
[69] Simpson-Herren and Lloyd (1970) *Cancer Chemother Rep.* 54:143-74.
[70] Workman et al. (2010) *Br. J. Cancer.* 102:1555-77.
[54] WO 2017/085520
[71] Rockwell et al., (1972) *J Natl Cancer Inst.* 49:735-49.
[72] Principe d'éthique de l'expérimentation animate, Directive n° 2010/63 CEE 22 Sep. 2010, Décrêt n° 2013-118 1 Feb. 2013.
[73] Guide for the Care and Use of Laboratory Animals: Eighth Edition. The National Academies Press; 2011
[74] Simpson-Herren and Lloyd (1970) *Cancer Chemother Rep.* 54:143-74.
[75] Workman et al. (2010) *Br. J. Cancer.* 102:1555-77.
[88] Van den Bogert et al. (2014), *PLOS One;* 9(12): 1-20.

The invention claimed is:

1. A method of increasing differentiation of cytotoxic T cells in a subject in need thereof, comprising
administering to the subject a pharmaceutical composition that comprises a bacteria strain of the genus *Enterococcus*, wherein the bacteria strain comprises a 16S rRNA gene sequence that has at least 95% sequence identity to the polynucleotide sequence of SEQ ID NO: 2, as determined by a Smith-Waterman homology search algorithm using an affine gap search with a gap open penalty of 12 and a gap extension penalty of 2,
wherein the subject has been diagnosed with deficient immune activity, and
wherein the administering is sufficient to increase differentiation of cytotoxic T cells in the subject, relative to a level of differentiation of cytotoxic T cells in the subject prior to the administering.

2. The method of claim 1, wherein the cytotoxic T cells are CD8 cells, and wherein the administering is sufficient to increase a level of CD8 cells in a serum of the subject, relative to a level of CD8 cells in the serum of the subject prior to the administering.

3. The method of claim 1, wherein the administering increases differentiation of T helper cells, relative to a level of differentiation of T helper cells in the subject prior to the administering.

4. The method of claim 1, wherein the administering activates a toll-like receptor (TLR) signaling pathway in the subject.

5. The method of claim 4, wherein the TLR is TLR5 or TLR9.

6. The method of claim 1, wherein the administering increases a level of a cytokine in a serum of the subject, relative to a level of the cytokine in the serum of the subject prior to the administering.

7. The method of claim 6, wherein the cytokine is IL-6 or IL-23.

8. The method of claim 1, wherein the administering increases a level of NFκBIA in the subject, relative to a level of NFκBIA in the subject prior to the administering.

9. The method of claim 1, wherein the administering comprises oral, rectal, nasal, buccal, sublingual, or subcutaneous administration.

10. The method of claim 1, wherein the bacterial strain is dried.

11. The method of claim 1, wherein the pharmaceutical composition comprises from about $1\times10^3$ to about $1\times10^{11}$ colony forming units (CFU)/g of the bacteria strain with respect to the total weight of the pharmaceutical composition.

12. The method of claim 1, wherein the bacteria strain at least partially colonizes an intestine of the subject.

13. The method of claim 1, wherein the pharmaceutical composition is formulated for delivery to an intestine of the subject.

14. The method of claim 1, wherein the bacteria strain comprises a 16S rRNA gene sequence that has at least 99% sequence identity to the polynucleotide sequence of SEQ ID NO: 2, as determined by a Smith-Waterman homology search algorithm using an affine gap search with a gap open penalty of 12 and a gap extension penalty of 2.

15. The method of claim 1, wherein the bacteria strain comprises a 16S rRNA gene sequence that is the polynucleotide sequence of SEQ ID NO: 2 or SEQ ID NO: 3.

16. The method of claim 1, wherein the bacterial strain is of the species *Enterococcus gallinarum*.

17. The method of claim 1, wherein the bacterial strain is the strain deposited under accession number NCIMB 42488 or the strain deposited under accession number NCIMB 42761.

18. The method of claim 1, wherein the pharmaceutical composition further comprises one or more pharmaceutically acceptable excipients, carriers, or diluents.

19. The method of claim 1, further comprising administering a cell therapy to the subject.

20. The method of claim 19, the cell therapy is chimeric antigen receptor T cell (CAR-T) therapy, mesenchymal stem cell (MSC) therapy, stem cell transplantation therapy, or hematopoietic stem cell transplantation.

* * * * *